(12) United States Patent
Sjogren et al.

US010287303B2

(10) Patent No.: US 10,287,303 B2
(45) Date of Patent: May 14, 2019

(54) COMPOSITIONS AND METHODS FOR INHIBITING ARGINASE ACTIVITY

(71) Applicant: CALITHERA BIOSCIENCES, INC., South San Francisco, CA (US)

(72) Inventors: Eric B. Sjogren, Mountain View, CA (US); Jim Li, San Francisco, CA (US); Lijing Chen, Cupertino, CA (US); Roland J. Billedeau, Santa Clara, CA (US); Timothy F. Stanton, Daly City, CA (US); Michael Van Zandt, Guilford, CT (US); Darren Whitehouse, Westbrook, CT (US); Gunnar E. Jagdmann, Jr., Branford, CT (US); Lene Raunkjær Petersen, Værløse (DK)

(73) Assignee: Calithera Biosciences, Inc., South San Francisco, CA (US)

( * ) Notice: Subject to any disclaimer, the term of this patent is extended or adjusted under 35 U.S.C. 154(b) by 0 days.

(21) Appl. No.: 15/853,310

(22) Filed: Dec. 22, 2017

(65) Prior Publication Data

US 2018/0222926 A1 Aug. 9, 2018

Related U.S. Application Data

(60) Provisional application No. 62/438,092, filed on Dec. 22, 2016, provisional application No. 62/439,614, filed on Dec. 28, 2016.

(51) Int. Cl.
| | |
|---|---|
| *C07F 5/02* | (2006.01) |
| *A61K 31/69* | (2006.01) |
| *A61K 45/06* | (2006.01) |
| *A61P 35/00* | (2006.01) |
| *A61P 35/02* | (2006.01) |
| *A61K 39/395* | (2006.01) |
| *A61K 31/4245* | (2006.01) |
| *C07K 16/28* | (2006.01) |
| *A61K 39/00* | (2006.01) |

(52) U.S. Cl.
CPC .......... *C07F 5/025* (2013.01); *A61K 31/4245* (2013.01); *A61K 31/69* (2013.01); *A61K 39/3955* (2013.01); *A61K 39/39558* (2013.01); *A61K 45/06* (2013.01); *A61P 35/00* (2018.01); *A61P 35/02* (2018.01); *C07K 16/2818* (2013.01); *A61K 2039/507* (2013.01); *A61K 2300/00* (2013.01)

(58) Field of Classification Search
CPC ............ A61K 2300/00; A61K 31/4245; A61K 31/69; A61K 39/3955; A61K 39/39558; A61K 45/06; A61P 35/00; A61P 35/02; C07F 5/025
See application file for complete search history.

(56) References Cited

U.S. PATENT DOCUMENTS

| | | |
|---|---|---|
| 8,894,970 B2 | 11/2014 | Tomczuk et al. |
| 9,200,011 B2 | 12/2015 | Van Zandt et al. |
| 9,233,985 B2 | 1/2016 | Van Zandt et al. |
| 9,266,908 B2 | 2/2016 | Van Zandt et al. |
| 9,440,995 B2 | 9/2016 | Van Zandt et al. |
| 2002/0081626 A1 | 6/2002 | Kaddurah-Daouk et al. |
| 2004/0063666 A1 | 1/2004 | Christianson et al. |
| 2010/0189644 A1 | 7/2010 | Christianson et al. |
| 2012/0083469 A1 | 4/2012 | Van Zandt et al. |
| 2012/0129806 A1 | 5/2012 | Van Zandt et al. |
| 2014/0371175 A1 | 12/2014 | Van Zandt et al. |
| 2015/0080341 A1 | 3/2015 | Van Zandt et al. |
| 2015/0191492 A1 | 7/2015 | Van Zandt et al. |
| 2016/0375044 A1 | 12/2016 | Gross et al. |

FOREIGN PATENT DOCUMENTS

| | | | |
|---|---|---|---|
| CA | 2431080 A1 | 12/2004 | |
| CN | 103068830 A | 4/2013 | |
| CN | 103402549 A | 11/2013 | |
| CN | 105879030 A | 8/2016 | |
| WO | WO-1999019295 A1 | 4/1999 | |
| WO | WO-2007005620 A2 | 1/2007 | |
| WO | WO-2010085797 A2 | 7/2010 | |
| WO | WO-2011133653 A1 | 10/2011 | |
| WO | WO-2012058065 A1 | 5/2012 | |
| WO | WO-2012091757 A1 | 7/2012 | |
| WO | WO 2013/059587 | * 4/2013 | .......... A61K 31/535 |
| WO | WO-2013059437 A1 | 4/2013 | |
| WO | WO-2013059587 A1 | 4/2013 | |
| WO | WO-2013158262 A1 | 10/2013 | |
| WO | WO-2015061752 A1 | 4/2015 | |
| WO | WO-2016153078 A1 | 9/2016 | |
| WO | WO-2016210106 A1 | 12/2016 | |

OTHER PUBLICATIONS

Ajinomoto Amino Acids Link News Aug. 2005 vol. 11: 3-4.
Arina, A. et al. 2014 "Adoptively Transferred Immune T Cells Eradicate Established Tumors despite Cancer-Induced Immune Suppression," *J. Immunol* 192: 1286-1293.
Baggio et al. 1997 "Inhibition of Mn2+ 2-Arginase by Borate Leads to the Design of a Transition State Analogue Inhibitor, 2(S)-Amino-6-boronohexanoic Acid," *J Am Chem Soc* 119(34): 8107-8108.
Barbul, A. 1990 "Arginine and Immune Function," Nutrition 6(1) 53-58.
Bartolucci et al. 2012 "Direct, Regioselective and Chemoselective Preparation of Novel Boronated Tryptophans by Friedel-Crafts Alkylation" *Organic Letters* 14(2): 600-603.
Busnel et al. 2005 "Synthesis and evaluation of new co-borono-a-amino acids as rat liver arginase inhibitors," *Bioorg Med Chem* 13(7): 2373-2379.
Calithera Biosciences, Inc. Poster, SITC Conference; Nov. 9-13, 2016; National Harbor, MD.

(Continued)

*Primary Examiner* — Erich A Leeser
(74) *Attorney, Agent, or Firm* — Dechert LLP; Carl A. Morales; Seth E. Snyder

(57) ABSTRACT

The disclosure relates to a novel class of compounds that exhibit activity inhibitory activity toward arginase, and pharmaceutical compositions comprising the compounds of the disclosure. Also provided herein are methods of treating cancer with the arginase inhibitors of the disclosure.

26 Claims, 6 Drawing Sheets

(56) References Cited

OTHER PUBLICATIONS

Calithera Biosciences, Inc. Poster, EORTC-NCI-AACR; Nov. 29-Dec. 2, 2016; Munich, Germany.
CAS Registry No. 1374395-07-9. CA Index Name: "3-Pyrrolidinecarboxylic acid, 3-amino-4-(3-boronopropyl)-14(5,7-dichloro-1,2,3,4-tetrahydro-3-isoquinolinyl)carbonyll-, (3R,4S)-rel-". STN Entry Date: May 24, 2012 (Last update: May 28, 2012).
Colleluori et al. 2001 "Classical and Slow-Binding Inhibitors of Human Type II Argmase," *Biochem*, 40(31): 9356-9362.
Curtis, B. et al. 2013 "Secondary amines containing one aromatic nitro group: preparation, nitrosation, sustained nitric oxide release, and the synergistic effects of released nitric oxide and an arginase inhibitor on vascular smooth muscle cell proliferation," *Bioorganic & medicinal chemistry* 21(5) 1123-1135. Retrieved from: <https://www.ncbi.nlm.nih.gov/pmc/articles/PMC3574223/pdf/nihms434525.pdf>.
Ellyard et al. 2010 "Alternatively Activated Macrophage Possess Antitumor Cytotoxicity That Is Induced by IL-4 and Mediated by Arginase-1," *J Immunother* 33: 443-452.
Geiger, Roger et al. 2016 "L-Arginine Modulates T Cell Metabolism and Enhances Survival and Anti-tumor Activity," *Cell, Cell Press* 167(3): 829ff.
Gritli-Linde, A. et al. 1998 "Opposing effects of suramin and DL-alpha-difluoromethylornithine on polyamine metabolism contribute to a synergistic action on B16 melanoma cell growth in vitro," *Anticancer Research* 18(2A) 863-870.
Hörig et al. 2004 "From bench to clinic and back: Perspective on the 1st IQPC Translational Research conference," *J Translational Med*, 2:44 doi:10.1186/1479-5876-2-44.
Ilies et al. 2011 "Binding of alpha,alpha-Disubstituted Amino Acids to Arginase Suggests New Avenues for Inhibitor Design," *J Med Chem* 54(15): 5432-5443.
International Search Report and Written Opinion for International Application No. PCT/US2017/068307 dated Mar. 26, 2018.
Ivanenkov et al. 2014 "Small-molecule arginase inhibitors," *Pharm Pat Anal* 3(1): 65-85.
Kabalka et al. 2008 "Synthesis of a series of boronated unnatural cyclic amino acids as potential boron neutron capture therapy agents," *Appl Organomet Chem*, 22(9): 516-522.
Koziara et al. 2004 "Paclitaxel nanoparticles for the potential treatment of brain tumors," *J Controlled Release* 99: 259-269.
Lei et al. 2009 "Progress of Boronic Acids as Enzyme Inhibitors" *Chinese J Pharm* 40(3): 213-219 (English Abstract only).
Li, L. et al. "An Engineered Arginase FC Protein Inhibits Tumor Growth In Vitro and In Vivo," *Evidence-Based Complementary and Alternative Medicine* vol. 2013, Article ID 243129: 1-9.
Lorvik, Kristina Berg et al. 2016 "Adoptive Transfer of Tumor-Specific Th2Cells Eradicates Tumors by Triggering an in Situ Inflammatory Immune Response," *Cancer Research* 76(23): 6864-6876.
Raber, P. et al. 2012 Metabolism of L-Arginine by Myeloid-Derived Suppressor Cells in Cancer: Mechanisms of T cell suppression and Therapeutic Perspectives *Immunol Invest* 41(6-7): 614-634.
Raber, P. et al. 2016 "T cells conditioned with MDSC show an increased anti-tumor activity after adoptive T cell base immunotherapy," *Oncotarget* 7(14): 17565-17578.
Rodriguez, P. et al. 2003 "L-Arginine Consumption by Macrophages Modulates the Expression of CD3x Chain in T Lymphocytes," *J Immunol* 17: 1232-1239.
Rodriguez, P. et al. 2004 "Arginase I Production in the Tumor Microenvironment by Mature Myeloid Cells Inhibits T-Cell Receptor Expression and Antigen-Specific T-Cell Responses," *Cancer Research* 64: 5839-5849.
Rodriguez, P. et al. 2008 "Arginine regulation by myeloid derived suppressor cells and tolerance in cancer: mechanisms and therapeutic perspectives," *Immunol Rev* 222: 180-191.
Rossnagl, Stephanie et al. 2016, "EDA-Fibronectin Originating from Osteoblasts Inhibits the Immune Response against Cancer," *PLoS Biology* 14(9): e1002562.
Sandgren, S. and Belting, M. 2003 "Suramin Selectively inhibits carcinoma cell growth that is dependent on extracellular polyamines," *Anticancer Research* 23(2B): 1223-1228.
Schafer, et al. 2008 "Failure is an option: learning from unsuccessful proof-of-concept trials," *Drug Discov Today*, 13(21): 913-916.
Scheit, K. and Bauer, G. 2014 "Synergistic effects between catalase inhibitors and modulators of nitric oxide metabolism on tumor cell apoptosis," *Anticancer Research* 34(10): 5337-5350. Retrieved from: <https://ar.iiarj ournals.org/content/34/10/5337.full.pdf+html>.
Segal et al. 2012 "Chronic Oral Administration of the Arginase Inhibitors 2(S)-amino-6-boronohexanoic Acid (ABH) Improves Erectile Function in Aged Rates," *J Androl*, 33(6): 11691175.
Selamnia, M. et al. 1998 "α-Difluoromethylornithine (DFMO) as a potent arginase activity inhibitor in human colon carcinoma cells," *Biochemical pharmacology* 55(8): 1241-1245.
Singh, S. et al. 2000 "Arginase Activity in Human Breast Cancer Cell Lines: $N^{\omega}$-Hydroxy-L-arginine Selectively Inhibits Cell Proliferation and Induces Apoptosis in MDA-MB-468 Cells" *Cancer Research* 60: 3305-3312.
Steggerda, SusanneM et al. 2016 "Abstract B045: Arginase inhibitor CB-1158 elicits immune-mediated antitumor responses as a single agent and in combination with other immunotherapies," Second CRI-CIMT-EATI-AACR International Cancer Immunotherapy Conference: Translating Science into Survival; Sep. 25-28, 2016; New York, NY.
Steggerda, SusanneM. et al. 2017, "Inhibition of arginase by CB-1158 blocks myeloid cell-mediated immune suppression in the tumor microenvironment," *Journal for ImmunoTherapy of Cancer* 5(1): 1-18.
Steppan et al. 2013 "Development of novel arginase inhibitors for therapy of endothelial dysfunction," *Front Immunol* 51(4): 5905-5908.
Tate et al. 2008 "Effect of arginase II on L-arginine depletion and cell growth in murine cell lines of renal cell carcinoma," *J Hematol Oncol* 1(14): 1-10.
Vissers, Y. et al. 2005 "Plasma arginine concentrations are reduced in cancer patients: evidence for arginine deficiency?" *Am J Clin Nutr* 81: 1142-1146.

\* cited by examiner

COMPOSITIONS AND METHODS FOR INHIBITING ARGINASE ACTIVITY

BACKGROUND

Cancer is characterized by the uncontrolled growth of cells in the body, leading to the invasion of essential organs and often death. Initially, the pharmacological treatment of cancer utilized non-specific cytotoxic agents that targeted all rapidly dividing cells, including normal cells. These non-specific cytotoxic agents have anti-tumor effects but their use is often limited by severe toxicities. As the understanding of the proteins and pathways that enable cancer cells to thrive has evolved, newer more targeted agents have been developed that block specific proteins that are activated in cancer cells.

An emerging field for the development of therapeutics that addresses the challenges presented in treating cancers is immuno-oncology, also referred to as tumor immunology. Certain tumor types have developed mechanisms to escape destruction by the body's immune system. Tumor immunology is a therapeutic area focused on activating the body's own immune system to attack and kill tumors. The naturally occurring amino acid arginine is implicated in tumor immunology, as it is important for the activation, growth, and survival of a body's cancer-fighting cytotoxic T-cells. However, levels of arginine are depleted in the tumor microenvironment by arginase, an enzyme produced and secreted by neutrophils and myeloid derived suppressor cells (MDSCs) that accumulate in cancer patients of multiple histotypes. In fact, elevated levels of arginase enzyme have been observed in the plasma of renal cell carcinoma, breast cancer, chronic myelogenous leukemia, esophageal cancer, prostate cancer, non-small cell lung cancer, glioblastoma, and acute myeloid leukemia patients. Therefore, there is a need to develop inhibitors of arginase that restore arginine levels in the tumor microenvironment, thus promoting the tumor-killing activity of cytotoxic T-cells.

SUMMARY OF DISCLOSURE

In certain embodiments, the disclosure provides a series compounds useful for the inhibition of arginase. The compounds of the disclosure have a structure of formula (I):

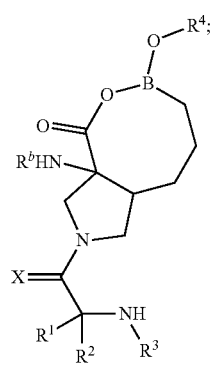

(I)

or a pharmaceutically acceptable salt thereof;

wherein $R^b$, X, $R^1$, $R^2$, $R^3$ and $R^4$ are defined as set forth in the detailed discussion of the disclosure section, below.

In certain embodiments, the

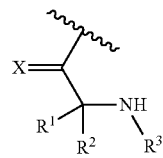

structure in the compounds of formula (I) represents an alpha-amino acid residue, wherein X=O and the terminal amine is optionally substituted with $R^3$. In such embodiments, $R^1$ group is an alpha-amino acid side chain. Suitable amino acid side chains include those of naturally and non-naturally occurring amino acids. For instance, in some embodiments $R^1$ is an amino acid side chain of Arg, His, Lys, Asp, Glu, Ser, Thr, Asn, Gln, Cys, Sec, Gly, Ala, Val, Ile, Leu, Met, Phe, Tyr, or Trp, in particular of Gly, Ser, or Ala. In certain embodiments, $R^1$ is an amino acid side chain of Gly, Ala, or Ser. In such embodiments, $R^1$ may take the R- or S-configuration.

In certain embodiments, the disclosure also provides pharmaceutical compositions comprising a compound of the disclosure and a pharmaceutically acceptable carrier.

In certain embodiments, the disclosure provides methods of treating or preventing cancer, comprising administering to a subject in need thereof a therapeutically effective amount of a compound or pharmaceutical composition of the disclosure.

The disclosure further provides methods for treating or preventing cancer, comprising conjointly administering to a subject in need thereof an arginase inhibitor of the disclosure and one or more additional chemotherapeutic agents.

In particular embodiments, the disclosure provides methods for treating or preventing cancer, comprising conjointly administering to a subject in need thereof an arginase inhibitor of the disclosure and an inhibitor of indoleamine 2,3-dioxygenase (IDO). The IDO inhibitor may be a compound disclosed in, or a compound having a structure of any one of the formulas disclosed herein. In particular embodiments, the IDO inhibitor is epacadostat.

(100 mg/kg PO BID); anti-CTLA-4 (5 mg/kg IP on Days 2, 5, 8) plus anti-PD-1 (5 mg/kg IP on days 3, 6, and 9); or the combination of Compound 10 with anti-CTLA-4 and anti-PD-1 (N=10 per group; *P<0.05; *P<0.001, ** P<0.0001 vs vehicle).

Figure 7:
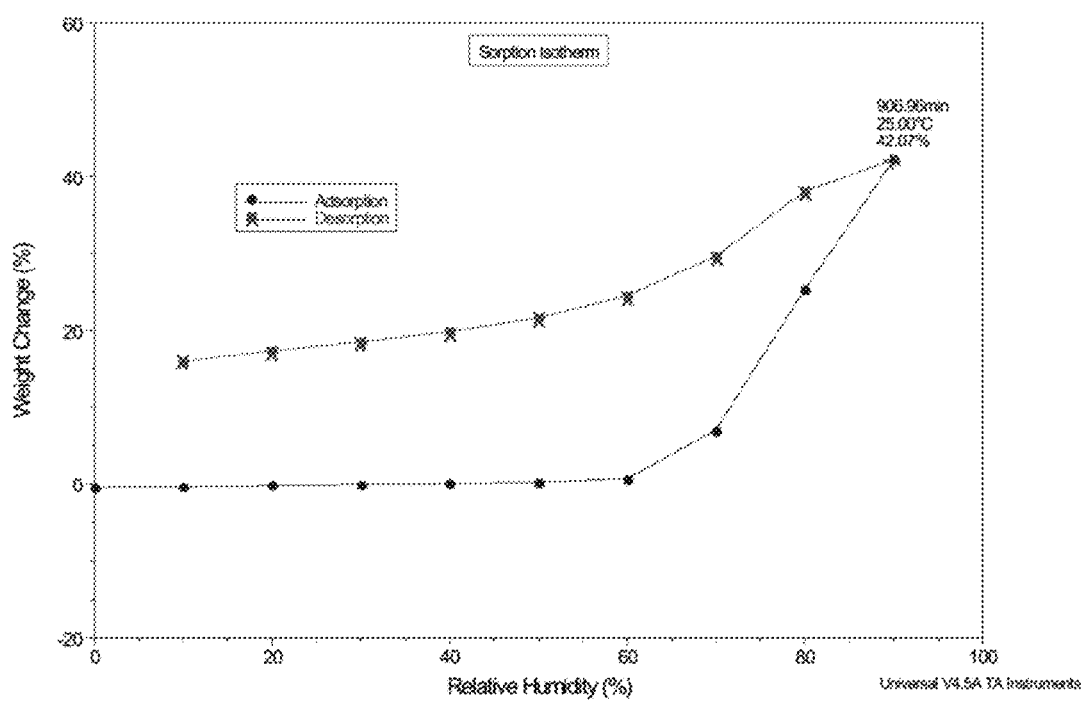

FIG. 7 is a graph of the sorption isotherm of compound 10e.

DETAILED DESCRIPTION OF THE DISCLOSURE

The present disclosure relates to compounds and compositions useful for the inhibition of arginase, as well as to various therapeutic applications thereof. The inventors' previous studies focused on a class of small molecules having (i) amino acid and (ii) boronic acid-type moieties, such as the compounds generically represented by Formula A, below. Compounds of Formula A were determined to be useful in the inhibition of arginase.

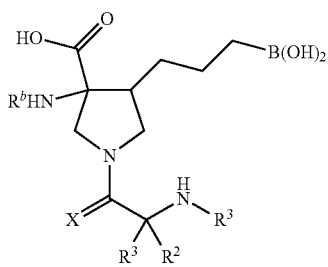

(Formula A)

Suprisingly, the inventors discovered that when a free base of compound of Formula A was treated with an anhydrous alcohol, a cyclic alkoxylated compound of formula (I) could be isolated. Unlike many prodrugs, such cyclic alkoxylated compounds of formula (I) do not require an enzymatic process to reveal the underlying arginase inhibitor compounds; rather, exposure of a compound of formula (I) to water or an aqueous environment (e.g., upon oral dosing) will generate the "underlying" arginase inhibitor, e.g., the compound of formula (A). Typically, these cyclic alkoxylated compounds of formula (I) exhibit improved processing and handling properties, higher purity, and better stability as compared to their uncyclized counterparts.

Compounds of the Disclosure

Accordingly, the disclosure provides a compound having a structure of formula (I):

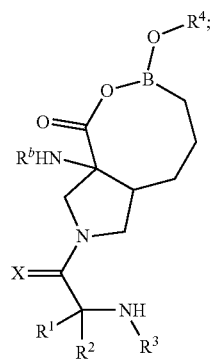

(I)

or a pharmaceutically acceptable salt thereof;
wherein the definitions of $R^b$, X, $R^1$, $R^2$, $R^3$ and $R^4$ are defined below In certain embodiments, the disclosure provides a compound having a structure of formula (I'):

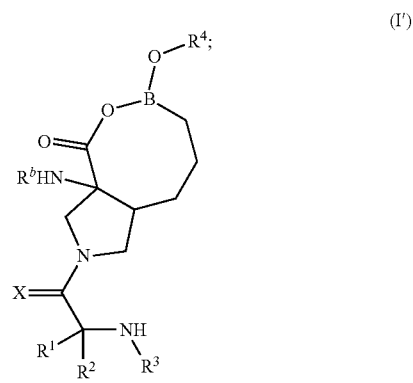

(I')

or a pharmaceutically acceptable salt thereof;
wherein:
$R^b$ is selected from H, alkyl, alkenyl, alkynyl, acyl, —C(O)O(alkyl), and —C(O)O(aryl);
X is O or S;
$R^1$ and $R^2$ are each independently selected from H, alkyl, —CH$_2$OH, alkenyl, alkynyl, cycloalkyl, (cycloalkyl)alkyl, heterocycloalkyl, (heterocycloalkyl)alkyl, aryl, heteroaryl, aralkyl, and heteroaralkyl; or
$R^1$ and $R^2$ are taken together with the intervening atoms to form a 3- to 7-membered ring; and
$R^3$ is H or alkyl;
or $R^1$ and $R^3$ are taken together with the intervening atoms to form a 5- to 7-membered ring; and
$R^4$ is H or $(C_1-C_6)$alkyl.

In certain embodiments of the compound of formula I', $R^2$ is H.

In certain embodiments of the compound of formula I', $R^b$ is H or alkyl. In particular embodiments, $R^b$ is H.

In certain embodiments of the compound of formula I', X is O.

In certain embodiments of the compound of formula I', if $R^1$ is H, then $R^3$ is not benzyl.

In certain embodiments of the compound of formula I', $R^1$ is H. In some such embodiments $R^2$ is H.

In certain embodiments of the compound of formula I', if $R^1$ is benzyl, then $R^3$ is not methyl.

In certain embodiments of the compound of formula I', $R^1$ is aralkyl, heteroaralkyl, (cycloalkyl)alkyl, or (heterocycloalkyl)alkyl.

In certain embodiments of the compound of formula I', $R^1$ is aralkyl or heteroaralkyl.

In certain embodiments of the compound of formula I', $R^1$ is benzyl.

In certain embodiments of the compound of formula I', $R^1$ is not benzyl substituted by —CF$_3$.

In certain embodiments of the compound of formula I', $R^1$ is heteroaralkyl. In particular embodiments $R^1$ is —CH$_2$-(1H-imidazol-4-yl).

In certain embodiments of the compound of formula I', $R^1$ is alkyl, alkenyl, or alkynyl.

In certain embodiments of the compound of formula I', $R^1$ is $(C_1-C_4)$alkyl. In some such embodiments, $R^2$ is H.

In certain embodiments of the compound of formula I', R¹ is methyl. In some such embodiments, R² is H.

In certain embodiments of the compound of formula I', R¹ is selected from cycloalkyl, heterocycloalkyl, aryl, and heteroaryl.

In certain embodiments of the compound of formula I', R¹ is —CH₂OH. In some such embodiments, R² is H.

In certain embodiments, both R¹ and R² are hydrogen.

In certain embodiments of the compound of formula I', R¹ and R² are taken together with the intervening atoms to form a 5- to 7-membered ring.

In certain embodiments of the compound of formula I', R³ is H.

In certain embodiments of the compound of formula I', R¹ and R³ are taken together with the intervening atoms to form a 5-membered ring.

In certain embodiments of the compound of formula I', R¹ and R³ taken together with the intervening atoms do not form a 5-membered ring.

In certain embodiments of the compound of formula I', R¹ and R³ are taken together with the intervening atoms to form a 6- or 7-membered ring.

In certain embodiments of the compound of formula I', R¹ and R³, taken together with the intervening atoms, do not form a tetrahydroisoquinolinyl ring, e.g.,

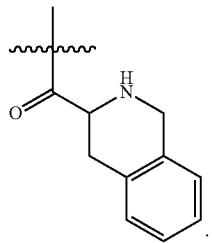 [SMILES: *C(=O)C1Cc2ccccc2CN1]

In certain embodiments of the compound of formula I', R⁴ is (C₁-C₄)alkyl. In particular embodiments the lower alkyl group is selected from methyl, ethyl, propyl, isopropyl and isobutyl. In particular embodiments, R⁴ is ethyl. In other particular embodiments, R⁴ is isopropyl.

In certain embodiments, the disclosure provides a compound having a structure of formula (I''):

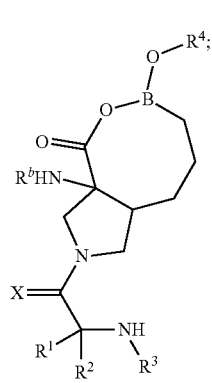

or a pharmaceutically acceptable salt thereof;
wherein:
R^b is H or is selected from optionally substituted alkyl, alkenyl, alkynyl, acyl, —C(O)O(alkyl), and —C(O)O(aryl);

X is O or S;
R¹ and R² are each independently selected from H and optionally substituted alkyl, alkenyl, alkynyl, cycloalkyl, (cycloalkyl)alkyl, heterocycloalkyl, (heterocycloalkyl)alkyl, aryl, heteroaryl, aralkyl, and heteroaralkyl;
or R¹ and R² are taken together with the intervening atoms to form an optionally substituted 3- to 7-membered ring; and
R³ is H or optionally substituted alkyl;
or R¹ and R³ are taken together with the intervening atoms to form an optionally substituted 5- to 7-membered ring; and
R⁴ is H or (C₁-C₆)alkyl.

In certain embodiments, the disclosure provides a compound having a structure of formula (I'''):

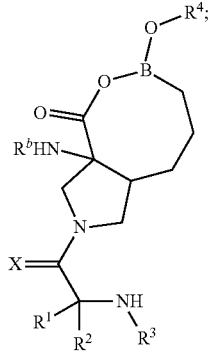

or a pharmaceutically acceptable salt thereof;
wherein:
R^b is H or is a group selected from alkyl, alkenyl, alkynyl, acyl, —C(O)O(alkyl), and —C(O)O(aryl), wherein said group is optionally substituted by one or more substituents selected from hydroxy, halo, haloalkyl, alkoxy, —SH, —S-(alkyl), —SeH, —Se-(alkyl), aryl, heteroaryl, cycloalkyl, heterocycloalkyl, amino, carboxylic acid, ester, guanidino, and amido;
X is O or S;
R¹ and R² are each independently selected from H or a group selected from alkyl, alkenyl, alkynyl, cycloalkyl, (cycloalkyl)alkyl, heterocycloalkyl, (heterocycloalkyl)alkyl, aryl, heteroaryl, aralkyl, and heteroaralkyl, wherein said group is optionally substituted by one or more substituents selected from hydroxy, halo, haloalkyl, alkoxy, —SH, —S-(alkyl), —SeH, —Se-(alkyl), aryl, heteroaryl, cycloalkyl, heterocycloalkyl, amino, carboxylic acid, ester, guanidino, and amido; or
R¹ and R² are taken together with the intervening atoms to form a 3- to 7-membered ring, wherein the 3- to 7-membered ring is optionally substituted with one or more substituents selected from hydroxy, halo, haloalkyl, alkoxy, —SH, —S-(alkyl), —SeH, —Se-(alkyl), aryl, heteroaryl, cycloalkyl, heterocycloalkyl, amino, carboxylic acid, ester, guanidino, and amido; and
R³ is H or alkyl optionally substituted with one or more substituents selected from hydroxy, halo, haloalkyl, alkoxy, —SH, —S-(alkyl), —SeH, —Se-(alkyl), aryl, heteroaryl, cycloalkyl, heterocycloalkyl, amino, carboxylic acid, ester, guanidino, and amido;

or R¹ and R³ are taken together with the intervening atoms to form a 5- to 7-membered ring, wherein the 5- to 7-membered ring is optionally substituted with one or more substituents selected from hydroxy, halo, haloalkyl, alkoxy, —SH, —S-(alkyl), —SeH, —Se-(alkyl), aryl, heteroaryl, cycloalkyl, heterocycloalkyl, amino, carboxylic acid, ester, guanidino, and amido; and R⁴ is H or (C₁-C₆)alkyl.

In certain embodiments of the compound of formula I''', R² is H.

In certain embodiments of the compound of formula I''', $R^b$ is H or alkyl. In particular embodiments, $R^b$ is H.

In certain embodiments of the compound of formula I''', X is O.

In certain embodiments of the compound of formula I''', if R¹ is H, then R³ is not benzyl.

In certain embodiments of the compound of formula I''', R¹ is H. In some such embodiments R² is H.

In certain embodiments of the compound of formula I''', if R¹ is benzyl, then R³ is not methyl.

In certain embodiments of the compound of formula I''', R¹ is aralkyl, heteroaralkyl, (cycloalkyl)alkyl, or (heterocycloalkyl)alkyl.

In certain embodiments of the compound of formula I''', R¹ is aralkyl or heteroaralkyl.

In certain embodiments of the compound of formula I''', R¹ is benzyl.

In certain embodiments of the compound of formula I''', R¹ is not benzyl substituted by —CF₃.

In certain embodiments of the compound of formula I''', R¹ is heteroaralkyl. In particular embodiments R¹ is —CH₂-(1H-imidazol-4-yl).

In certain embodiments of the compound of formula I''', R¹ is alkyl, alkenyl, or alkynyl.

In certain embodiments of the compound of formula I''' R¹ is alkyl optionally substituted by one or more substituents independently selected from hydroxy, alkoxy, haloalkyl, and —S-(alkyl).

In certain embodiments of the compound of formula I''', R¹ is (C₁-C₄)alkyl. In some such embodiments, R² is H.

In certain embodiments of the compound of formula I''', R¹ is methyl. In some such embodiments, R² is H.

In certain embodiments of the compound of formula I''', R¹ is —CH₂OH. In some such embodiments, R² is H.

In certain embodiments of the compound of formula I''', R¹ is selected from cycloalkyl, heterocycloalkyl, aryl, and heteroaryl. In some such embodiments, the cycloalkyl, heterocycloalkyl, aryl, or heteroaryl group is optionally substituted with one or more groups selected from hydroxy, halo, haloalkyl, alkoxy, —SH, and —S-(alkyl).

In certain embodiments of the compound of formula I''', R¹ is —CH₂OH. In some such embodiments, R² is H.

In certain embodiments the compound of formula I''', R¹ is an amino acid side chain of Arg, His, Lys, Asp, Glu, Ser, Thr, Asn, Gln, Cys, Sec, Gly, Ala, Val, Ile, Leu, Met, Phe, Tyr, or Trp.

In certain embodiments of the compound of formula I''', R¹ and R² are taken together with the intervening atoms to form a 5- to 7-membered ring.

In certain embodiments of the compound of formula I''', R³ is H.

In certain embodiments of the compound of formula I''', R¹ and R³ are taken together with the intervening atoms to form a 5-membered ring.

In certain embodiments of the compound of formula I''', R¹ and R³ taken together with the intervening atoms do not form a 5-membered ring.

In certain embodiments of the compound of formula I''', R¹ and R³ are taken together with the intervening atoms to form a 6- or 7-membered ring.

In certain embodiments of the compound of formula I''', R¹ and R³, taken together with the intervening atoms, do not form a tetrahydroisoquinolinyl ring, e.g.,

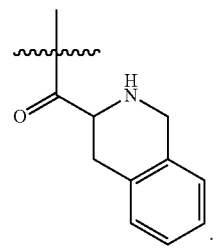 [SMILES: *C(=O)C1Cc2ccccc2CN1]

In certain embodiments of the compound of formula I''', R⁴ is (C₁-C₄)alkyl. In particular embodiments the lower alkyl group is selected from methyl, ethyl, propyl, isopropyl and isobutyl. In particular embodiments, R⁴ is ethyl. In other particular embodiments, R⁴ is isopropyl.

In certain embodiments, the disclosure provides a compound having a structure of formula (I*):

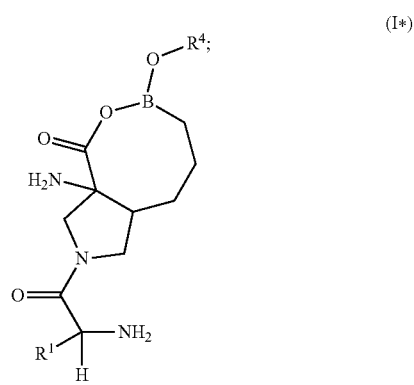

(I*)

or a pharmaceutically acceptable salt thereof;
wherein:
R¹ is selected from H or a group selected from alkyl, alkenyl, alkynyl, cycloalkyl, (cycloalkyl)alkyl, heterocycloalkyl, (heterocycloalkyl)alkyl, aryl, heteroaryl, aralkyl, and heteroaralkyl, wherein said group is optionally substituted by one or more substituents selected from hydroxy, halo, haloalkyl, alkoxy, —SH, —S-(alkyl), —SeH, —Se-(alkyl), aryl, heteroaryl, cycloalkyl, heterocycloalkyl, amino, carboxylic acid, ester, guanidino, and amido; and R⁴ is H or (C₁-C₆)alkyl.

In certain embodiments of the compound of formula I*, R¹ is aralkyl, heteroaralkyl, (cycloalkyl)alkyl, or (heterocycloalkyl)alkyl.

In certain embodiments of the compound of formula I*, R¹ is aralkyl or heteroaralkyl.

In certain embodiments of the compound of formula I*, R¹ is benzyl.

In certain embodiments of the compound of formula I*, R¹ is not benzyl substituted by —CF₃.

In certain embodiments of the compound of formula I*, $R^1$ is heteroaralkyl. In particular embodiments $R^1$ is —CH$_2$-(1H-imidazol-4-yl).

In certain embodiments of the compound of formula I*, $R^1$ is alkyl, alkenyl, or alkynyl.

In certain embodiments of the compound of formula I*, $R^1$ is alkyl optionally substituted by one or more substituents independently selected from hydroxy, alkoxy, haloalkyl, and —S-(alkyl).

In certain embodiments of the compound of formula I*, $R^1$ is (C$_1$-C$_4$)alkyl. In certain embodiments of the compound of formula I*, $R^1$ is methyl.

In certain embodiments of the compound of formula I*, $R^1$ is selected from cycloalkyl, heterocycloalkyl, aryl, and heteroaryl. In some such embodiments, the cycloalkyl, heterocycloalkyl, aryl, or heteroaryl group is optionally substituted with one or more groups selected from hydroxy, halo, haloalkyl, alkoxy, —SH, and —S-(alkyl).

In certain embodiments of the compound of formula I*, $R^1$ is —CH$_2$OH.

In certain embodiments the compound of formula I*, $R^1$ is an amino acid side chain of Arg, His, Lys, Asp, Glu, Ser, Thr, Asn, Gln, Cys, Sec, Gly, Ala, Val, Ile, Leu, Met, Phe, Tyr, or Trp.

In certain embodiments of the compound of formula I*, $R^4$ is (C$_1$-C$_4$)alkyl. In particular embodiments the lower alkyl group is selected from methyl, ethyl, propyl, isopropyl and isobutyl. In particular embodiments, $R^4$ is ethyl. In other particular embodiments, $R^4$ is isopropyl.

In a particular embodiment, the compound of formula I* has the following structure:

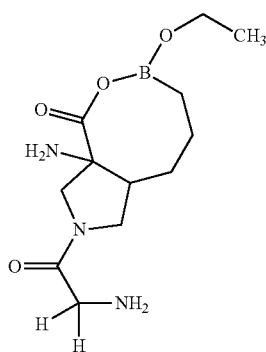 [SMILES: CCOB1CCCC2CN(C(=O)CN)CC2(N)C(=O)O1]

The compound may be a free base or may be ionized to form a pharmaceutically acceptable salt thereof.

In another particular embodiment, the compound of formula I* the following structure:

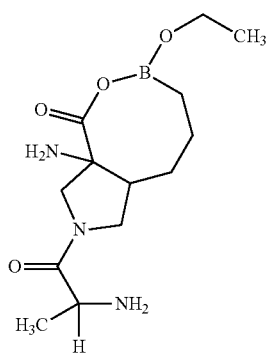 [SMILES: CCOB1CCCC2CN(C(=O)C(C)N)CC2(N)C(=O)O1]

The compound may be a free base or may be ionized to form a pharmaceutically acceptable salt thereof.

In another particular embodiment, the compound of formula I* has the following structure:

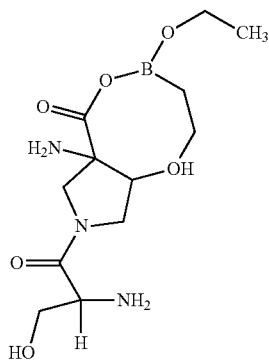 [SMILES: CCOB1CCOC2CN(C(=O)C(N)CO)CC2(N)C(=O)O1]

The compound may be a free base or may be ionized to form a pharmaceutically acceptable salt thereof.

In another particular embodiment, the compound of formula I* has the following structure:

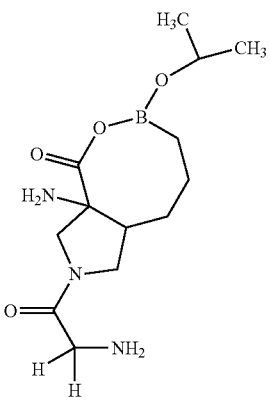 [SMILES: CC(C)OB1CCCC2CN(C(=O)CN)CC2(N)C(=O)O1]

The compound may be a free base or may be ionized to form a pharmaceutically acceptable salt thereof.

In another particular embodiment, the compound of formula I* has the following structure:

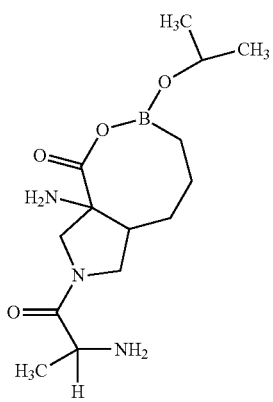 [SMILES: CC(C)OB1CCCC2CN(C(=O)C(C)N)CC2(N)C(=O)O1]

The compound may be a free base or may be ionized to form a pharmaceutically acceptable salt thereof.

In another particular embodiment, the compound of formula I* has the following structure:

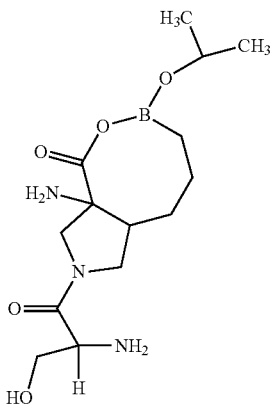 [SMILES: CC(C)OB1CCCC2CN(C(=O)C(N)CO)CC2(N)C(=O)O1]

The compound may be a free base or may be ionized to form a pharmaceutically acceptable salt thereof.

In certain embodiments, the compound of formula (I) has a structure of formula (Ia):

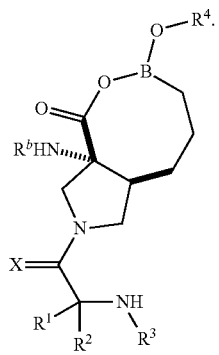

(Ia)

In certain embodiments, the compound of formula (I) has a structure of formula (Ib):

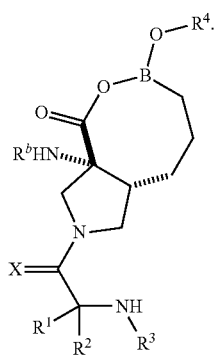

(Ib)

In certain embodiments, the compound of formula (I) has a structure of formula (Ic):

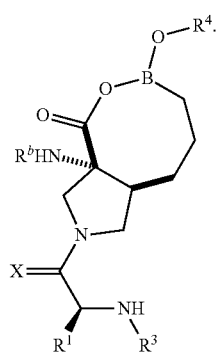

(Ic)

In certain embodiments, the compound of formula (I) has a structure of formula (Id):

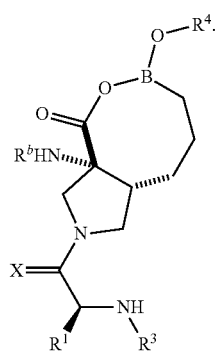

(Id)

In certain embodiments, the compound of formula (I) has a structure of formula (Ie):

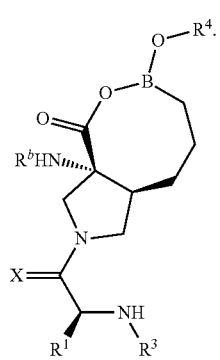

(Ie)

In certain embodiments, the compound of formula (I) has a structure of formula (If):

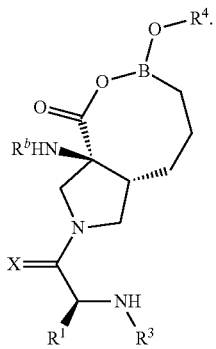

(If)

In certain embodiments, the compound of formula (I) has a structure of formula (Ig):

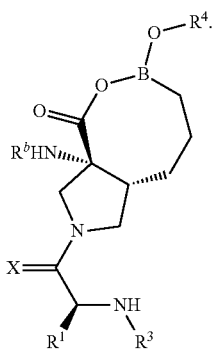

(Ig)

In certain embodiments, the compound of formula (I) has a structure of formula (Ih):

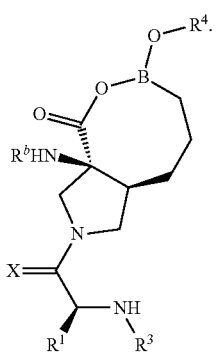

(Ih)

For the compounds of formulas (Ia), (Ib), (Ic), (Id), (Ie), (If), (Ig) and (Ih), the variables $R^b$, X, $R^1$, $R^2$, $R^3$ and $R^4$ are as described above for the various formulas falling within formula (I).

It will be understood that any recitation of the compound of formula (I) in the disclosure below includes the compounds of formulas (I'), (I''), (I'''), (I*), (Ia), (Ib), (Ic), (Id), (Ie), (If), (Ig) and (Ih).

Related arginase inhibitors are described in U.S. Patent Application Publication Nos. 2014/0343019, 2012/0083469, 2014/0371175, 2012/0129806, 2015/0080341, and PCT Application Publication Nos. WO 99/19295, WO 2010/085797, and WO 2012/091757, which are hereby incorporated by reference herein in their entirety. Such related arginase inhibitors are expected to form cyclic alkoxylated compounds similar to the compounds of the disclosure when they are treated with an anhydrous alcohol. In some embodiments, an anhydrous alcohol comprises 1-5% water, preferably <1% water, most preferably <0.5% water.

For example, U.S. Patent Application Publication No. 2012/0129806 discloses the arginase inhibitor of formula J:

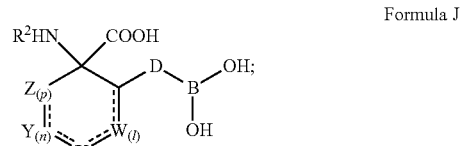

Formula J wherein:
$R^2$ is selected from H, straight or branched ($C_1$-$C_6$) alkyl, and ($C_1$-$C_6$)alkyl-C(O)—;
W, X, Y, and Z are each independently selected from —C(R')(R''')—, —C(R''')$_2$—, —CR'''—, —NR'''—, —N—, —O—, —C(O)—, and —S—, wherein no more than three of W, X, Y, and Z simultaneously represent a bond; at least one of W, X, Y, or Z is selected from —NR'''—, —N—, —O—, and —S—; and no two adjacent members of W, X, Y, and Z are simultaneously —O—, —S—, —N—, or —NR'''—;
l, m, n and p are each independently 0 or 1 or 2;

optionally represents one or more double bonds;
D is selected from straight or branched ($C_3$-$C_5$)alkylene;
R', R'' and R''' are each independently selected from H, OH, S(O)$R^d$, S(O)$_2R^d$, ($C_1$-$C_8$)alkyl, ($C_3$-$C_6$)aryl, —NH$_2$, —NH($C_1$-$C_6$)alkyl, —N[($C_1$-$C_6$)alkyl]$_2$, —C(O)NR$^d$R$^e$, —C(O)($C_1$-$C_6$)alkyl, —C(O)($C_3$-$C_{14}$)aryl, —C(O)O($C_1$-$C_6$)alkyl, —C(O)O($C_3$-$C_{14}$)aryl, ($C_3$-$C_6$)cycloalkyl, ($C_3$-$C_{14}$)heterocycloalkyl, —C(O)($C_3$-$C_{14}$)heterocycloalkyl, ($C_3$-$C_{14}$)heteroaryl, ($C_3$-$C_{14}$)aryl-($C_1$-$C_6$)alkylene-, —C(O) ($C_3$-$C_{14}$)aryl-($C_1$-$C_6$)alkylene-, —C(O)($C_3$-$C_{14}$)aryl, ($C_3$-$C_6$)cycloalkyl-($C_1$-$C_6$)alkylene-, ($C_3$-$C_{14}$)heteroaryl-($C_1$-$C_6$)alkylene-, and ($C_3$-$C_{14}$)heterocycle-($C_1$-$C_6$)alkylene-;
wherein any alkyl, alkylene, aryl, heteroaryl, cycloalkyl, or heterocycloalkyl is optionally substituted with one or more members selected from halogen, oxo, —COOH, —CN, —NO$_2$, —OH, —NR$^d$R$^e$, —NR$^g$S(O)$_2R^h$, ($C_1$-$C_6$)alkoxy, ($C_3$-$C_{14}$)aryl, ($C_1$-$C_6$)haloalkyl and ($C_3$-$C_{14}$)aryloxy;
wherein $R^d$, $R^e$, $R^g$, and $R^h$ are each independently selected from H, straight or branched ($C_1$-$C_6$)alkyl, optionally substituted ($C_3$-$C_{14}$)aryl($C_1$-$C_6$)alkylene-, optionally substituted ($C_3$-$C_{14}$)aryl, ($C_1$-$C_6$)hydroxyalkyl, ($C_1$-$C_6$) aminoalkyl, H$_2$N($C_1$-$C_6$)alkylene-, optionally substituted ($C_3$-$C_6$)cycloalkyl, optionally substituted ($C_3$-$C_{14}$)heterocycloalkyl, optionally substituted ($C_3$-$C_{14}$)heteroaryl, optionally substituted ($C_3$-$C_{14}$)aryl-($C_1$-$C_6$)alkylene-, NR'R''C (O)—, and ($C_3$-$C_6$)aryl-($C_3$-$C_{14}$)-cycloalkylene-.

Upon treatment with an anhydrous alcohol, the compound of formula J can cyclize to form the compound of Formula B:

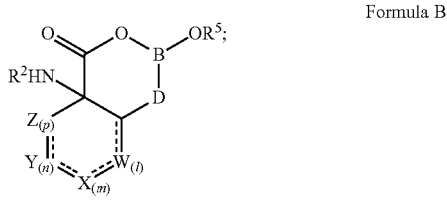

Formula B wherein R⁵ is H or lower alkyl, and the remaining variables are as defined for Formula J.

In certain embodiments of the compound of Formula B, $R^5$ is lower alkyl, preferably methyl, ethyl, propyl, or isopropyl. Most preferably, $R^5$ is ethyl.

In certain embodiments, D is propylene.

In certain embodiments, a compound of the present disclosure may have a prodrug modification, e.g., at the $R^1$ position. For example, compounds of Formula I may have $R^1$ equal to an amino acid side chain of an amino acid such as Arg or Lys. In certain such embodiments, the guanidino or amino group of such a side chain may be protected as, for example, an amide. Alternatively, in embodiments in which $R^1$ is a side chain of a serine residue, a hydroxyl group in the parent compound may be presented as an ester or a carbonate. In yet further embodiments in which $R^1$ is a side chain of a glutamic acid residue, a carboxylic acid group present in the parent compound may be presented as an ester. In certain such embodiments, the prodrug is metabolized to the active parent compound in vivo (e.g., the amide is hydrolyzed to the corresponding amino or guanidino group, the ester or carbonate is hydrolyzed to the hydroxyl, or the ester is hydrolyzed to the carboxylic acid).

In certain embodiments, compounds of the disclosure may be racemic. In certain embodiments, compounds of the disclosure may be enriched in one enantiomer. For example, a compound of the disclosure may have greater than 30% ee, 40% ee, 50% ee, 60% ee, 70% ee, 80% ee, 90% ee, or even 95% or greater ee.

The compounds of the disclosure have more than one stereocenter. Accordingly, the compounds of the disclosure may be enriched in one or more diastereomers. For example, a compound of the disclosure may have greater than 30% de, 40% de, 50% de, 60% de, 70% de, 80% de, 90% de, or even 95% or greater de. In certain embodiments, the compounds of the disclosure have substantially one isomeric configuration at one or more stereogenic centers, and have multiple isomeric configutations at the remaining stereogenic centers.

In certain embodiments, the enantiomeric excess of the stereocenter bearing $R^1$ is at least 40% ee, 50% ee, 60% ee, 70% ee, 80% ee, 90% ee, 92% ee, 94% ee, 95% ee, 96% ee, 98% ee or greater ee.

As used herein, single bonds drawn without stereochemistry do not indicate the stereochemistry of the compound. The compound of formula (I) provides an example of a compound for which no stereochemistry is indicated.

As used herein, hashed or bolded non-wedge bonds indicate relative, but not absolute, stereochemical configuration (e.g., do not distinguish between enantiomers of a given diastereomer). For example, in formula (Ia),

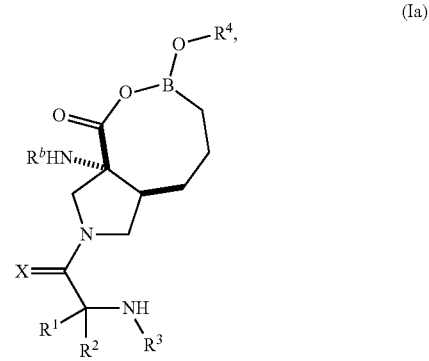

the bold, non-wedge bonds indicate that the —CO₂Rᵃ group and the (CH₂)₃B(ORᶜ)₂ group are configured to be cis to one another, but the bold, non-wedge bonds do not represent the absolute (i.e., R or S) configuration of the compound.

As used herein, hashed or bolded wedge bonds indicate absolute stereochemical configuration. For example, in formula (Ic),

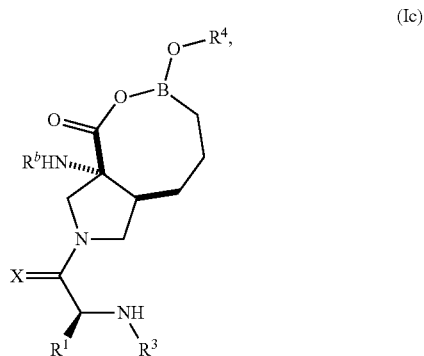

the bold, wedge bond indicates the absolute configuration of the stereocenter to which it is attached, while the bold, non-wedge bonds indicate that the —CO₂Rᵃ group and the (CH₂)₃B(ORᶜ)₂ group are configured to be cis to one another, but do not indicate the absolute configuration of those stereocenters. Therefore, the compound of formula (Ic) represents two isomers in total:

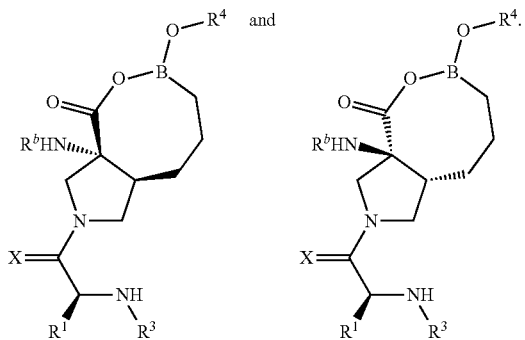

In certain embodiments, a therapeutic preparation of the compound of the disclosure may be enriched to provide predominantly one enantiomer of a compound. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, a therapeutic preparation may be enriched to provide predominantly one diastereomer of the compound of the disclosure. A diastereomerically enriched mixture may comprise, for example, at least 60 mol percent of one diastereomer, or more preferably at least 75, 90, 95, or even 99 mol percent.

In certain embodiments, a preparation of the compound of the disclosure may comprise at least 50 mol %, at least 60 mol %, at least 70 mol %, at least 80 mol %, at least 90 mol %, or at least 95 mol % of the cyclic alkoxylated compounds of the disclosure. In certain such embodiments, the balance of the preparation is the uncyclized free boronic ester counterpart or the cyclized but unesterified boronic acid (e.g., Formula I, $R^4$=H; Scheme 1).

In certain embodiments, the compounds of the disclosure exhibit an improved pharmacokinetic profile relative to existing arginase inhibitors. In one embodiment, the cyclic alkoxylated compounds of the disclosure, when administered to a subject or a number of subjects, provide an increased (or decreased) T max relative to that obtained by administration of a uncyclized free boronic ester counterpart, as referred to herein, of at least about 10%, or at least about 20%, or at least about 30%, or at least about 40%, or at least about 50%, and under similar conditions and administered in similar dosages. In one embodiment, the cyclic alkoxylated compounds compounds of the disclosure, when administered to a subject or a number of subjects, provide an increased (or decreased) C max relative to that obtained by administration of a uncyclized free boronic ester counterpart, as referred to herein, of at least about 10%, or at least about 20%, or at least about 30%, or at least about 40%, or at least about 50%, and under similar conditions and administered in similar dosages.

In certain embodiments, the compounds of the disclosure exhibit improved bioavailability relative to existing arginase inhibitors. In one embodiment, the cyclic alkoxylated compounds of the disclosure, when administered to a subject or a number of subjects, provide an increased bioavailability relative to that obtained by administration of an uncyclized free boronic ester counterpart (e.g., compounds of Formula J described herein) of at least about 20%, or at least about 25%, or at least about 30%, or at least about 35%, or at least about 40%, or at least about 45%, or at least about 50%, or at least about 55%, or at least about 60%, such as at least 65%, the bioavailability being determined as AUC(0-infinity) and under similar conditions and administered in similar dosages.

The cyclic alkoxylated compounds of the disclosure are typically less hygroscopic than their free boronic ester counterparts (e.g., compounds of Formula J described herein). For example, compound 10e, pictured in the examples, has low water content and is resistant to absorbance of water up to about 60% relative humidity, whereas its free boronic acid counterpart, compound 10, has higher water content and absorbs increasing amounts of water as the humidity increases, resulting in a less well defined composition.

The cyclic alkoxylated compounds of the disclosure can be about 50%, 45%, 40%, 35%, 30%, 25%, 20%, 15%, 10%, or 5% less hygroscopic than their free boronic ester counterparts as measured by standard techniques, such as thermogravimetric analysis (TGA) or dynamic vapor sorption (DVS). These values can be used for define a range, such as from about 40% to about 20%.

In certain embodiments, the cyclic alkoxylated compounds of the disclosure are crystalline. The cyclic alkoxylated compounds of the disclosure typically have higher degrees of crystallinity than their free boronic ester counterparts (e.g., compounds of Formula J described herein). For instance, compound 10e also shows defined peaks by powder X-ray diffraction which are not seen for its free boronic acid counterpart, compound 10, which is amorphous.

In certain embodiments, the cyclic alkoxylated compounds of the disclosure have a purity level of greater than 96%, 97%, or 98%. In certain embodiments, the cyclic alkoxylated compounds of the disclosure have a purity level of greater than 99%. In certain embodiments, the cyclic alkoxylated compounds of the disclosure have a purity level of greater than 99.5%. In certain embodiments, the cyclic alkoxylated compounds of the disclosure have a purity level of greater than 99.8%.

As a result, the cyclic alkoxylated compounds of the disclosure may have advantageous properties, allowing the preparation of more stable compositions, exhibiting better handling properties in the manufacturing process, and ultimately can result in compositions having higher purity and stability. In some embodiments, a pharmaceutical composition comprising a cyclic alkoxylated compound of the disclosure, when exposed to an environment of at least 50% humidity for at least 24 hours, takes up less than 50% (preferably less than 25%, or even less than 10% or 5%) of the water that a corresponding composition of an uncyclized free boronic ester counterpart of the compound takes up under identical conditions.

In certain embodiments, the cyclic alkoxylated compounds of the present disclosure exhibit improved stability, such as improved storage stability, with respect to structurally related compounds that have a free and non-cyclized boronic acid group (e.g., compounds of Formula J described herein). For example, the present compounds or pharmaceutical compositions, may exhibit improved storage stability by exhibiting less than about 10%, 7%, 5%, 4%, 3%, 2%, 1%, or 0.5% impurities by weight following storage under stressed conditions. Stressed conditions include storage over at least one, two, three, four, five, or six months at 25° C. and 60% RH, at 30° C. and 65% RH, or at 40° C. and 75% RH. Such compounds or compositions may be considered to be storage stable. In some embodiments, the impurities are associated with decomposition or degradation of the subject compound. Determination of the amount of impurities present in a sample of the present compounds or pharmaceutical compositions that has been subjected to stressed conditions may be performed by typical analytical methods known in the art, such as by HPLC or NMR analysis.

In certain embodiments, the present compounds or pharmaceutical compositions, exhibit improved storage stability by exhibiting little or no change in purity profile after being subject to stressed conditions as defined herein. For instance, following being subjected to stressed conditions, the cyclic alkoxylated compounds of the disclosure or pharmaceutical compositions comprising the cyclic alkoxylated compounds of the disclosure may exhibit a decrease in purity of about 10, 7, 5, 4, 3, 2, 1, or 0.5 percentage points or less (e.g., a decrease from 98% purity to 97% purity would be a decrease of 1 percentage point or less).

Methods of Treatment

Several specific approaches to T-cell activation have shown considerable recent promise in the treatment of tumors. One such approach involves activation of T-cells by blockade of the T-cell surface antigen CTLA-4 by the antibody ipilimumab. A second approach is to prevent the activation of immune checkpoints by blocking the interaction of programmed cell death 1 protein, or PD-1, expressed on T-cells and its ligand, PD-L1 found on many tumors. A third approach is to activate the T-cell receptor by supplying key stimulating factors or nutrients such as tryptophan.

Inhibitors of indoleamine dioxygenase, or IDO, have been shown to restore extracellular tryptophan without which the T-cell receptor cannot become active. Arginine, like tryptophan, is an amino acid that is fundamental to the function of cytotoxic T-cells. Without arginine, tumor-specific cytotoxic T-cells fail to express a functional T-cell receptor on their surface and as a result are unable to activate, proliferate, or mount an effective anti-tumor response. In response to tumor-secreted factors, myeloid-derived suppressor cells, or MDSCs, accumulate around the tumor and secrete the enzyme arginase, resulting in depletion of arginine from the tumor microenvironment.

Depletion of arginine due to elevated levels of arginase has been observed in renal cell carcinoma and acute myeloid leukemia. In addition, significant MDSC infiltrates have been observed in pancreatic, breast and other tumor types. Certain embodiments of the present disclosure provide a method of treating cancer by increasing arginine levels in a tumor microenvironment, thereby allowing activation of the body's cytotoxic T-cells.

One means of increasing arginine levels in the tumor microenvironment is by inhibiting arginase. Inhibitors of arginase, such as the compounds of the disclosure, may promote an anti-tumor immune response by restoring arginine levels, thereby allowing activation of the body's cytotoxic T-cells.

Accordingly, in certain embodiments, the disclosure provides methods for treating or preventing cancer, comprising administering to a subject in need thereof a therapeutically effective amount of a compound of formula (I) (which includes compounds of formulas (I'), (I"), (I'''), (I*), (Ia), (Ib), (Ic), (Id), (Ie), (If), (Ig) and (Ih)), or a pharmaceutical composition comprising said compound.

In certain embodiments, the cancer that is treated by the methods of the disclosure is Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Extracranial Germ Cell Tumor, Extragonadal Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CIVIL), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Renal Pelvis Cancer, Ureter Cancer, Transitional Cell Cancer, Retinoblastoma, Rhabdomyosarcoma, Salivary Gland Cancer, Sarcoma, Sézary Syndrome, Skin Cancer, Small Cell Lung Cancer, Small Intestine Cancer, Soft Tissue Sarcoma, Squamous Cell Carcinoma, Squamous Neck Cancer with Occult Primary, Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Gestational Trophoblastic Tumor, Unknown Primary, Unusual Cancer of Childhood, Urethral Cancer, Uterine Cancer, Uterine Sarcoma, Waldenström Macroglobulinemia, or Wilms Tumor.

In certain embodiments, the cancer that is treated by the methods of the disclosure is a variety of acute myeloid leukemia (AML), breast cancer, colorectal cancer, chronic myelogenous leukemia (CML), esophageal cancer, gastric cancer, lung cancer, melanoma, non-small cell lung carcinoma (NSCLC), pancreatic cancer, prostate cancer, or renal cancer.

In certain embodiments, the cancer is selected from bladder cancer, breast cancer (including TNBC), cervical cancer, colorectal cancer, chronic lymphocytic leukemia (CLL), diffuse large B-cell lymphoma (DLBCL), esophageal adenocarcinoma, glioblastoma, head and neck cancer, leukemia (acute and chronic), low-grade glioma, lung cancer (including adenocarcinoma, non-small cell lung cancer, and squamous cell carcinoma), Hodgkin's lymphoma, non-Hodgkin lymphoma (NHL), melanoma, multiple myeloma (MM), ovarian cancer, pancreatic cancer, prostate cancer, renal cancer (including renal clear cell carcinoma and kidney papillary cell carcinoma), and stomach cancer.

Combination therapy is an important treatment modality in many disease settings, such as cancer. Recent scientific advances have increased our understanding of the pathophysiological processes that underlie these and other complex diseases. This increased understanding has provided impetus to develop new therapeutic approaches using combinations of drugs directed at multiple therapeutic targets to improve treatment response, minimize development of resistance, or minimize adverse events. In settings in which combination therapy provides significant therapeutic advantages, there is growing interest in the development of combinations with new investigational drugs, such as arginase inhibitors.

When considering the administration of multiple therapeutic agents together, one must be concerned about what sort of drug interactions will be observed. This action can be positive (when the drug's effect is increased) or antagonistic (when the drug's effect is decreased) or a new side effect can be produced that neither produces on its own.

When the interaction causes an increase in the effects of one or both of the drugs the interaction, the degree to which the final effect of the combined drugs is greater than administering either drug alone can be calculated resulting in what is called the "combination index" (CI) (Chou and Talalay, 1984). A combination index at or around 1 is considered "additive"; whereas a value greater than 1 is considered "synergistic".

The present disclosure provides methods for combination therapy in treating or preventing cancer comprising an arginase inhibitor (e.g., a compound of the disclosure) and one or more additional chemotherapeutic agents.

Certain embodiments of the disclosure relate to treating cancer comprising conjointly administering a chemotherapeutic agent and a compound of the disclosure.

In certain embodiments, the chemotherapeutic is an immune-stimulating agent. For example, the immune-stimulating agent may be a pro-inflammatory agent.

The chemotherapeutic agent that may be conjointly administered with the arginase inhibitors described herein in the methods of the disclosure include ABT-263, afatinib dimaleate, aminoglutethimide, amsacrine, anastrozole, asparaginase, axitinib, Bacillus Calmette-Guérin vaccine (bcg), bevacizumab, BEZ235, bicalutamide, bleomycin, bortezomib, buserelin, busulfan, cabozantinib, campothecin, capecitabine, carboplatin, carfilzomib, carmustine, ceritinib, chlorambucil, chloroquine, cisplatin, cladribine, clodronate, cobimetinib, colchicine, crizotinib, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, eribulin, erlotinib, estradiol, estramustine, etoposide, everolimus, exemestane, filgrastim, fludarabine, fludrocortisone, fluorouracil and 5-fluorouracil, fluoxymesterone, flutamide, gefitinib, gemcitabine, genistein, goserelin, GSK1120212, hydroxyurea, idarubicin, ifosfamide, imatinib, interferon, irinotecan, ixabepilone, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, MK2206, mitomycin, mitotane, mitoxantrone, mutamycin, nilutamide, nocodazole, octreotide, olaparib, oxaliplatin, paclitaxel, pamidronate, pazopanib, pemetrexed, pentostatin, perifosine, PF-04691502, plicamycin, pomalidomide, porfimer, procarbazine, raltitrexed, ramucirumab, rituximab, romidepsin, rucaparib, selumetinib, sirolimus, sorafenib, streptozocin, sunitinib, suramin, talazoparib, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, vinorelbine, and vorinostat (SAHA).

In certain embodiments, the chemotherapeutic agent that may be administered with the arginase inhibitors described herein in the methods of the disclosure include abagovomab, adecatumumab, afutuzumab, alemtuzumab, anatumomab mafenatox, apolizumab, atezolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MGA012, MPDL3280A, nivolumab, obinutuzumab, ocaratuzumab, ofatumumab, olatatumab, pembrolizumab, pidilizumab, rituximab, ticilimumab, samalizumab, or tremelimumab.

In certain embodiments, the chemotherapeutic agent is ipilimumab, MGA012, nivolumab, pembrolizumab, or pidilizumab.

Many combination therapies have been developed for the treatment of cancer. In certain embodiments, compounds of the disclosure may be conjointly administered with a combination therapy. Examples of combination therapies with which compounds of the disclosure may be conjointly administered are included in Table 1.

TABLE 1

Exemplary combinatorial therapies for the treatment of cancer.

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |

TABLE 1-continued

Exemplary combinatorial therapies for the treatment of cancer.

| Name | Therapeutic agents |
|------|-------------------|
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocyte leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/ cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/ MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |

TABLE 1-continued

Exemplary combinatorial therapies for the treatment of cancer.

| Name | Therapeutic agents |
| --- | --- |
| TCP | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In certain embodiments, the conjointly administered chemotherapeutic agent is selected from a metabolic enzyme inhibitor, such as glucose transporters, hexokinase, pyruvate kinase M2, lactate dehydrogenase 1 or 2, pyruvate dehydrogenase kinase, fatty acid synthase and glutaminase. In some embodiments, the inhibitor inhibits lactate dehydrogenase 1 or 2, or glutaminase. In certain embodiments, the inhibitor is CB-839.

In some embodiments, the conjointly administered chemotherapeutic agent is an immuno-oncology therapeutic agent, such as an inhibitor of CTLA-4, indoleamine 2,3-dioxygenase, and/or PD-1/PD-L1. In certain embodiments, the immuno-oncology therapeutic agent is abagovomab, adecatumumab, afutuzumab, anatumomab mafenatox, apolizumab, atezolizumab, blinatumomab, catumaxomab, durvalumab, epacadostat, epratuzumab, indoximod, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, or tremelimumab. In some embodiments, the immuno-oncology agent is indoximod, ipilimumab, nivolumab, pembrolizumab, or pidilizumab. In certain embodiments, the immuno-oncology therapeutic agent is ipilimumab.

Exemplary immuno-oncology agents are disclosed in Adams, J. L. et al. "Big Opportunities for Small Molecules in Immuno-Oncology" *Nature Reviews Drug Discovery* 2015, 14, page 603-621, the contents of which are hereby incorporated by reference.

In certain embodiments, the conjointly administered chemotherapeutic agent is a pro-inflammatory agent. In certain embodiments, the pro-inflammatory agent administered with the arginase inhibitors of the disclosure is a cytokine or a chemokine.

Pro-inflammatory cytokines are produced predominantly by activated macrophages and are involved in the up-regulation of inflammatory reactions. Exemplary pro-inflammatory cytokines include but are not limited to IL-1, IL-1β, IL-6, IL-8, TNF-α, and IFN-γ.

Chemokines are a group of small cytokines. Pro-inflammatory chemokines promote recruitment and activation of multiple lineages of leukocytes (e.g., lymphocytes, macrophages). Chemokines are related in primary structure and share several conserved amino acid residues. In particular, chemokines typically include two or four cysteine residues that contribute to the three-dimensional structure via formation of disulfide bonds. Chemokines may be classified in one of four groups: C—C chemokines, C—X—C chemokines, C chemokines, and C—$X_3$—C chemokines. C—X—C chemokines include a number of potent chemoattractants and activators of neutrophils, such as interleukin 8 (IL-8), PF4 and neutrophil-activating peptide-2 (NAP-2). The C—C chemokines include, for example, RANTES (Regulated on Activation, Normal T Expressed and Secreted), macrophage inflammatory proteins 1-alpha and 1-beta (MIP-1α and MIP-1β), eotaxin and human monocyte chemotactic proteins 1 to 3 (MCP-1, MCP-2, MCP-3), which have been characterized as chemoattractants and activators of monocytes or lymphocytes. Accordingly, exemplary pro-inflammatory chemokines include MIP-1α, MIP-1β, MIP-1γ, MCP-1, MCP-2, MCP-3, IL-8, PF4, NAP-2, RANTES, CCL2, CCL3, CCL4, CCL5, CCL11, CXCL2, CXCL8, and CXCL10.

In certain embodiments, the method of treating or preventing cancer further comprises administering one or more non-chemical methods of cancer treatment, such as radiation therapy, surgery, thermoablation, focused ultrasound therapy, cryotherapy, or a combination of the foregoing.

Cellular pathways operate more like webs than superhighways. There are multiple redundancies, or alternate routes, that are activated in response to the inhibition of a pathway. This redundancy promotes the emergence of resistant cells or organisms under the selective pressure of a targeted agent, resulting in drug resistance and clinical relapse.

In certain embodiments of the disclosure, the chemotherapeutic agent is administered simultaneously with the arginase inhibitor. In certain embodiments, the chemotherapeutic agent is administered within about 5 minutes to within about 168 hours prior or after of the arginase inhibitor.

The present disclosure provides combination therapies comprising an immuno-oncology agent selected from inhibitors of CTLA-4, indoleamine 2,3-dioxygenase, and PD-1/PD-L1, and an arginase inhibitor of formula (I). In certain embodiments, the combination therapy treats or prevents cancer, an immunological disorder, or a chronic infection.

The present disclosure provides combination therapies comprising an immuno-oncology agent selected from inhibitors of an indoleamine 2,3-dioxygenase, and PD-1/PD-L1, and an arginase inhibitor of formula (I), such as combinations with epacadostat and nivolumab, epacadostate and pembrolizumab, and epacadostat and MGA012. In certain embodiments, the combination therapy treats or prevents cancer, an immunological disorder, or a chronic infection.

In certain embodiments, the disclosure provides methods for treating or preventing an immunological disease, comprising administering to a subject in need thereof a therapeutically effective amount of a compound of the disclosure (e.g., a compound of formula (I), or a pharmaceutical composition comprising said compound.

In certain embodiments, the immunological disease is selected from ankylosing spondylitis, Crohn's disease, erythema nodosum leprosum (ENL), graft versus host disease (GVHD), HIV-associated wasting syndrome, lupus erythematosus, organ transplant rejection, post-polycythemia, psoriasis, psoriatic arthritis, recurrent aphthous ulcers, rheumatoid arthritis (RA), severe recurrent aphthous stomatitis, systemic sclerosis, and tuberous sclerosis.

In certain embodiments, the method for treating or preventing an immunological disease further comprises conjointly administering an immuno-oncology therapeutic agent, as described above.

In certain embodiments, the disclosure provides methods for treating or preventing a chronic infection, comprising administering to a subject in need thereof a therapeutically effective amount of a compound of the disclosure (e.g., a compound of formula (I)), or a pharmaceutical composition comprising said compound.

In certain embodiments, the chronic infection is selected from bladder infection, chronic fatigue syndrome, cytomegalovirus/epstein barr virus, fibromyalgia, hepatitis B virus (HBV), hepatitis C virus (HCV), HIV/AIDS virus, mycoplasma infection, and urinary tract infections.

In certain embodiments, the method for treating or preventing a chronic infection further comprises conjointly administering an immuno-oncology therapeutic agent, as described above.

In certain embodiments, the disclosure provides a method for the treatment or prevention of a disease or condition associated with expression or activity of arginase I, arginase II, or a combination thereof in a subject, comprising administering to the subject a therapeutically effective amount of at least one of formula (I), or a pharmaceutically acceptable salt or stereoisomer thereof.

In certain embodiments, the disease or condition is selected from cardiovascular disorders, sexual disorders, wound healing disorders, gastrointestinal disorders, autoimmune disorders, immune disorders, infections, pulmonary disorders, and hemolytic disorders.

In certain embodiments, the disease or condition is a cardiovascular disorder selected from systemic hypertension, pulmonary arterial hypertension (PAH), pulmonary arterial hypertension in high altitude, ischemia reperfusion (IR) injury, myocardial infarction, and atherosclerosis.

In certain embodiments, the disease or condition is pulmonary arterial hypertension (PAH).

In certain embodiments, the disease or condition is myocardial infarction or atherosclerosis.

In certain embodiments, the disease or condition is a pulmonary disorder selected from chemically-induced lung fibrosis, idiopathic pulmonary fibrosis, cystic fibrosis, chronic obstructive pulmonary disease (COPD), and asthma.

In certain embodiments, the disease or condition is an autoimmune disorder selected from encephalomyelitis, multiple sclerosis, anti-phospholipid syndrome 1, autoimmune hemolytic anaemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture's syndrome.

In certain embodiments, the disease or condition is an immune disorder selected from myeloid-derived suppressor cell (MDSC) mediated T-cell dysfunction, human immunodeficiency virus (HIV), autoimmune encephalomyelitis, and ABO mismatch transfusion reaction.

In certain embodiments, the disease or condition is myeloid-derived suppressor cell (MDSC) mediated T-cell dysfunction.

In certain embodiments, the disease or condition is a hemolytic disorder selected from sickle-cell disease, thalassemias, hereditary spherocytosis, stomatocytosis, microangiopathic hemolytic anemias pyruvate kinase deficiency, infection-induced anemia, cardiopulmonary bypass and mechanical heart valve-induced anemia, and chemical induced anemia.

In certain embodiments, the disease or condition is a gastrointestinal disorder selected from gastrointestinal motility disorders, gastric cancer, inflammatory bowel disease, Crohn's disease, ulcerative colitis, and gastric ulcer.

In certain embodiments, the disease or condition is a sexual disorder selected from Peyronie's Disease and erectile dysfunction.

In certain embodiments, the disease or condition is ischemia reperfusion (IR) injury selected from liver IR, kidney IR, and myocardial IR.

In certain embodiments, the disease or condition is selected from renal disease inflammation, psoriasis, leishmaniasis, neurodegenerative diseases, wound healing, human immunodeficiency virus (HIV), hepatitis B virus (HBV), *H. pylori* infections, fibrotic disorders, arthritis, candidiasis, periodontal disease, keloids, adenotonsillar disease, African sleeping sickness and Chagas' disease.

In certain embodiments, the disease or condition is a wound healing disorder selected from infected and uninfected wound healing.

In certain embodiments, the combination therapy regimen is more efficacious than a therapy regimen of the arginase inhibitor as a single agent, or a therapy regimen of the additional chemotherapeutic agent as a single agent.

Combinations of Arginase Inhibitors of the Disclosure with IDO Inhibitors

The disclosure provides methods for treating or preventing cancer in a subject, comprising conjointly administering to a subject in need thereof an arginase inhibitor of formula (I) (which includes compounds of formulas (I'), (I''), (I'''), (I*), (Ia), (Ib), (Ic), (Id), (Ie), (If), (Ig) and (Ih) and an IDO inhibitor. The IDO inhibitor may be a compound disclosed in, or a compound having a structure of any one of the formulas disclosed herein. In certain embodiments, the methods further comprise conjointly administering one or more additional chemotherapeutic agents.

In certain embodiments, the subject is a human.

The disclosure further provides pharmaceutical kits, comprising an IDO inhibitor, an arginase inhibitor of formula (I), and optionally directions on how to administer the IDO inhibitor and the arginase inhibitor.

In certain embodiments, the IDO inhibitor is epacadostat, norharmane, rosmarinic acid, 1-methyltryptophan, a tryptophan derivative, indoximod, or NLG919, or pharmaceutically acceptable salts thereof. In certain embodiments, the IDO inhibitor is epacadostat. In certain embodiments, the IDO inhibitor has a structure of any of the formulas disclosed herein. In certain embodiments, the IDO inhibitor is a compound of any of the formulas disclosed herein.

Suitable IDO inhibitors for use in the compositions and methods disclosed herein are described in U.S. Patent Application Publication Nos. 20160158353, US2015353546, US2015291632, US2015218186, US2015291557, US2015246898, US2016002242, US2016015712, US2016166574, US2015051202; U.S. Pat. Nos. 8,748,461, 9,309,273, 8,809,378, 8,883,797, 8,669,274, 8,389,543, 9,447,073, 9,150,527, 9,056,855, 8,987,315, 9,409,914, 9,120,804, 9,073,944, 9,320,735, 9,023,851; PCT Application Publication Nos. WO2016059412, WO2016051181, WO2016057986, WO2016196890; and Europeant Patent Publication Nos. EP2804858, EP2563771; which are hereby incorporated by reference herein in their entirety, and in particular for the compound structures disclosed therein.

In some embodiments, suitable IDO inhibitors for use in the compositions and methods disclosed herein are the IDO inhibitors described in U.S. Pat. No. 7,767,675, which is hereby incorporated by reference herein in its entirety. In some embodiments, the IDO inhibitor is a compound of Formula (II), or a pharmaceutically acceptable salt thereof:

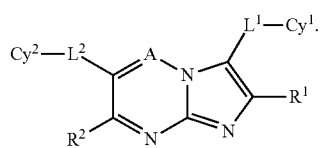

Formula (II)

In some embodiments, the IDO inhibitor is a compound selected from one of the following formulas or a pharmaceutically acceptable salt thereof:

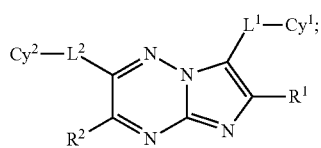

Formula (IIa)

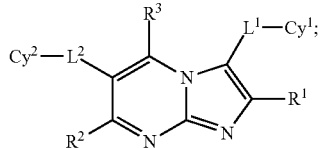

Formula (IIb)

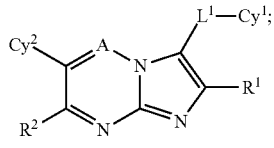

Formula (IIc)

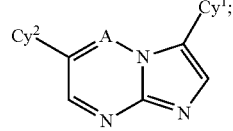

Formula (IId)

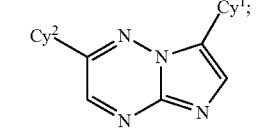

Formula (IIe)

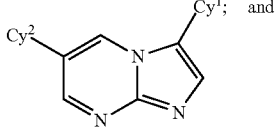

Formula (IIf)

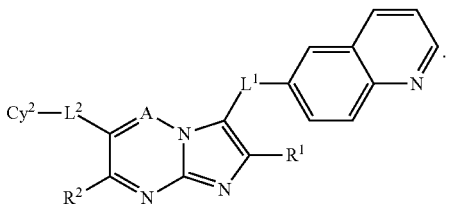

Formula (IIg)

The variable definitions, embodiments, and compound structures are as described in U.S. Pat. No. 7,767,675.

In some embodiments, suitable IDO inhibitors for use in the compositions and methods disclosed herein are the IDO inhibitors described in U.S. Pat. No. 8,088,803, which is hereby incorporated by reference herein in its entirety. In some embodiments, the IDO inhibitor is a compound of Formula (III), or a pharmaceutically acceptable salt thereof:

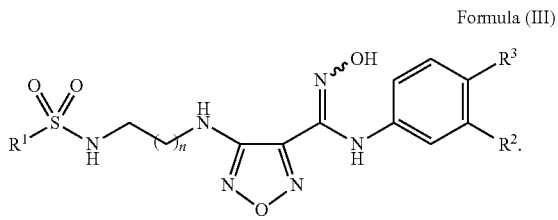

Formula (III)

In some embodiments, the IDO inhibitor is a compound selected from Formula F15, F19, and F28, or a pharmaceutically acceptable salt thereof:

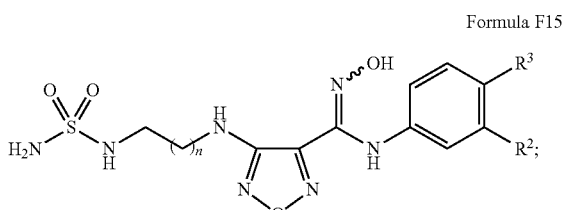

Formula F15

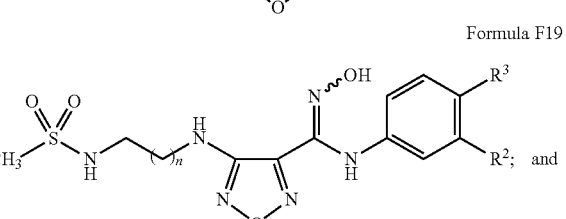

Formula F19 and

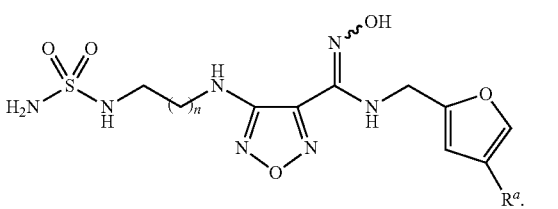

Formula F28

The variable definitions, embodiments, and compound structures are as described in U.S. Pat. No. 8,088,803.

In some embodiments, suitable IDO inhibitors for use in the compositions and methods disclosed herein are the IDO inhibitors described in U.S. Pat. No. 8,377,976, which is hereby incorporated by reference herein in its entirety. In some embodiments, the IDO inhibitor is a compound of Formula (IV), or a pharmaceutically acceptable salt thereof:

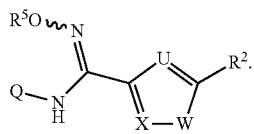

Formula (IV)

In some embodiments, the IDO inhibitor is a compound selected from one of the following formulas, or a pharmaceutically acceptable salt thereof:

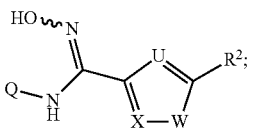

Formula (IVa)

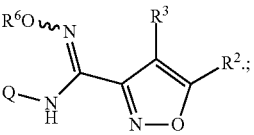

Formula (IVb)

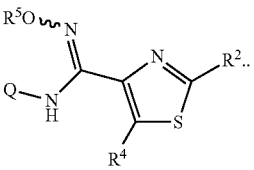

Formula (IVc)

The variable definitions, embodiments, and compound structures are as described in U.S. Pat. No. 8,377,976.

In some embodiments, suitable IDO inhibitors for use in the compositions and methods disclosed herein are the IDO inhibitors described in U.S. Pat. No. 8,507,541, which is hereby incorporated by reference herein in its entirety. In some embodiments, the IDO inhibitor is a compound of Formula (V), or a pharmaceutically acceptable salt thereof:

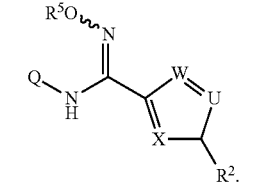

Formula (V)

In some embodiments, the IDO inhibitor is a compound selected from one of the following formulas, or a pharmaceutically acceptable salt thereof:

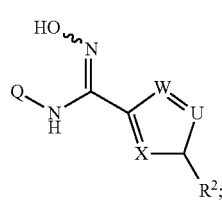

Formula (Va)

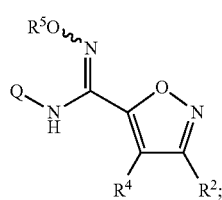

Formula (Vb)

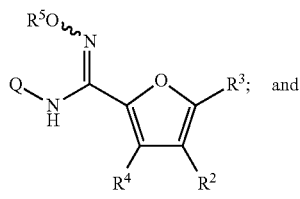

Formula (Vc)

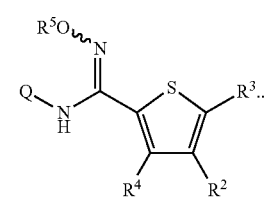

Formula (Vd)

The variable definitions, embodiments, and compound structures are as described in U.S. Pat. No. 8,507,541.

In some embodiments, suitable IDO inhibitors for use in the compositions and methods disclosed herein are the IDO inhibitors described in U.S. Pat. No. 9,321,755, which is hereby incorporated by reference herein in its entirety. In some embodiments, the IDO inhibitor is a compound of Formula (VI), or a pharmaceutically acceptable salt thereof:

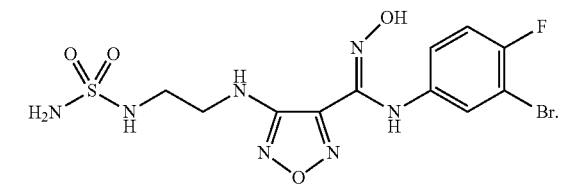

Formula (VI)

In some embodiments, the IDO inhibitor is a compound selected from Formula F5, F8, F10, F15, F16, F17, F18, F19, and F20, or a pharmaceutically acceptable salt thereof:

Formula F5

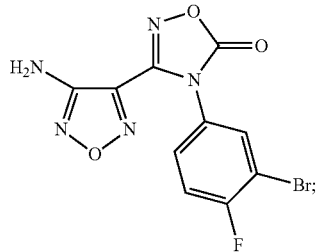

Formula F18

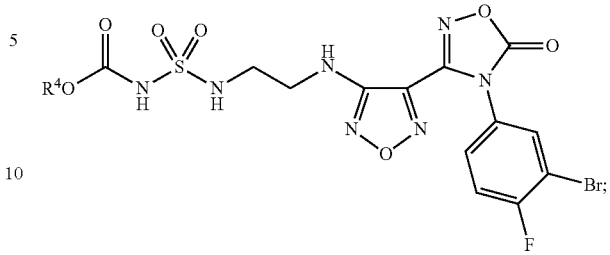

Formula F8

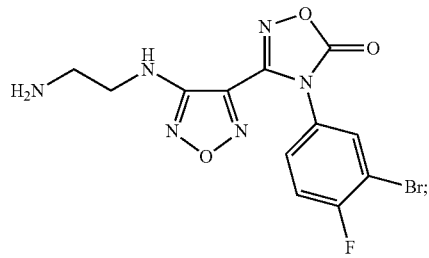

Formula F19

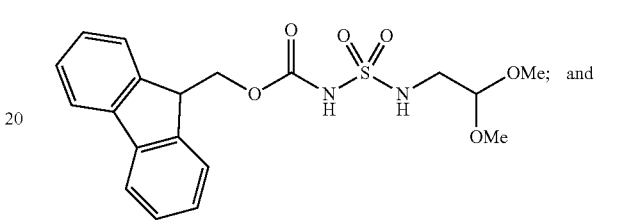

Formula F10

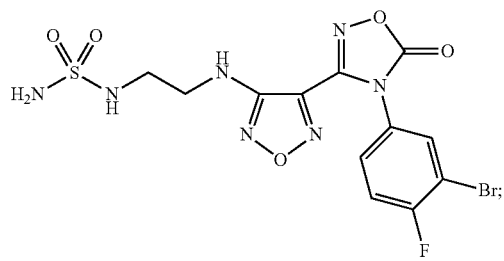

Formula F20

Formula F15

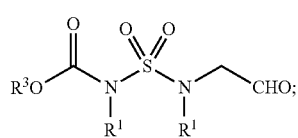

The variable definitions, embodiments, and compound structures are as described in U.S. Pat. No. 9,321,755.

In some embodiments, suitable IDO inhibitors for use in the compositions and methods disclosed herein are the IDO inhibitors described in U.S. Pat. No. 8,748,469, which is hereby incorporated by reference herein in its entirety. In some embodiments, the IDO inhibitor is a compound of Formula (VII), Formula (VIII), or a pharmaceutically acceptable salt thereof:

Formula F16

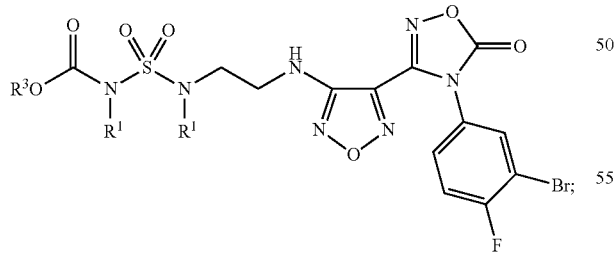

Formula (VII)

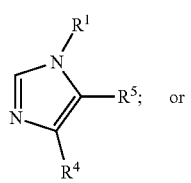

Formula (VIII)

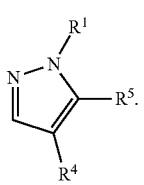

Formula F17

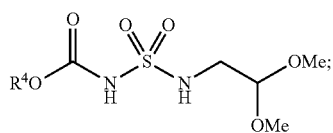

In some embodiments, the IDO inhibitor is a compound selected from one of the following formulas, or a pharmaceutically acceptable salt thereof:

Formula (IXa), Formula (IXb), Formula (IXc), Formula (IXd), Formula (IXe), Formula (IXf), Formula (IXg), Formula (IXh), Formula (IXi), Formula (IXj), Formula (IXk), Formula (IXl), Formula (IXm), Formula (IXn), Formula (IXo), Formula (IXp), Formula (IXq), Formula (IXr), Formula (IXs), Formula (IXt), Formula (IXu), Formula (IXv), Formula (IXw)

Formula (IXx)

Formula (IXy)

Formula (IXz)

Formula (IXaa)

Formula (IXab)

Formula (IXac)

Formula (IXad)

Formula (IXae)

Formula (IXaf)

Formula (IXag)

Formula (IXah)

Formula (IXai)

Formula (IXaj)

Formula (IXak)

Formula (IXal)

Formula (IXam)

Formula (IXan)

Formula (IXao)

Formula (IXap)

Formula (IXaq)

Formula (IXar)

Formula (IXas)

Formula (IXat)
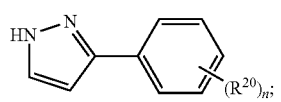

Formula (IXau)
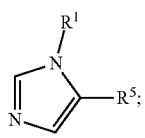

Formula (IXav)
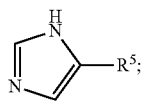

Formula (IXaw)
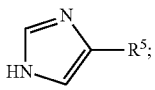

Formula (IXax)
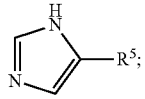

Formula (IXay)
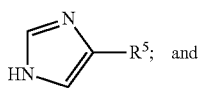 and

Formula (IXaz)
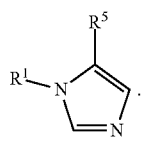

The variable definitions, embodiments, and compound structures are as described in U.S. Pat. No. 8,748,469.

In some embodiments, suitable IDO inhibitors for use in the compositions and methods disclosed herein are the IDO inhibitors described in U.S. Pat. No. 9,260,434, which is hereby incorporated by reference herein in its entirety. In some embodiments, the IDO inhibitor is a compound of Formula (X), or a pharmaceutically acceptable salt thereof:

Formula (X)
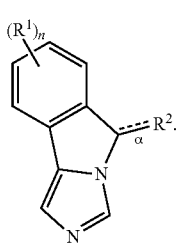

In some embodiments, the IDO inhibitor is a compound selected from one of the following formulas, or a pharmaceutically acceptable salt thereof:

Formula (Xa)
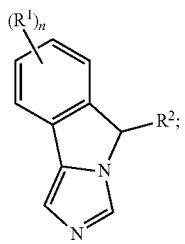

Formula (Xb)
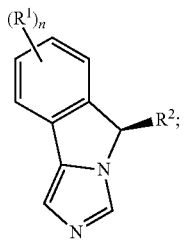

Formula (Xc)
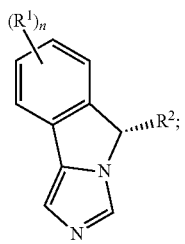

Formula (Xd)
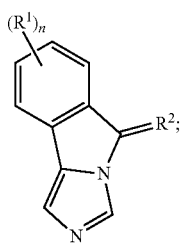

Formula (Xe)
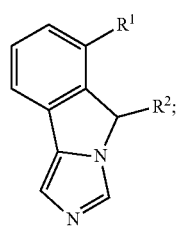

Formula (Xf)
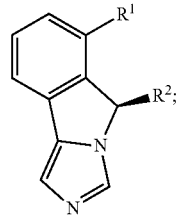

Formula (Xg)

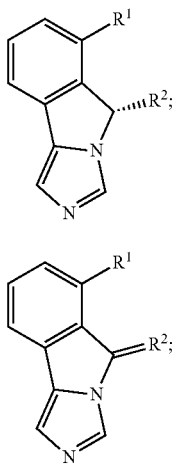

Formula (Xh)

The variable definitions, embodiments, and compound structures are as described in U.S. Pat. No. 9,260,434.

In some embodiments, suitable IDO inhibitors for use in the compositions and methods disclosed herein are the IDO inhibitors described in U.S. Pat. No. 9,120,804, which is hereby incorporated by reference herein in its entirety. In some embodiments, the IDO inhibitor is a compound of Formula (XI), or a pharmaceutically acceptable salt thereof:

Formula (XI)

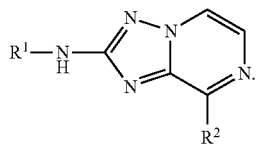

The variable definitions, embodiments, and compound structures are as described in U.S. Pat. No. 9,120,804.

In some embodiments, suitable IDO inhibitors for use in the compositions and methods disclosed herein are the IDO inhibitors described in U.S. Patent Publication Number 2008/0146624, which is hereby incorporated by reference herein in its entirety. In some embodiments, the IDO inhibitor is a compound of Formula (XII), (XIII), or a pharmaceutically acceptable salt thereof:

Formula (XII)

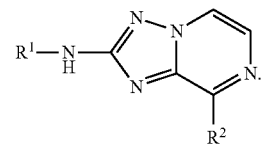

or

Formula (XIII)

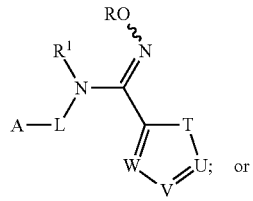

In some embodiments, the IDO inhibitor is a compound selected from one of the following formulas, or a pharmaceutically acceptable salt thereof:

Formula (XIVa)

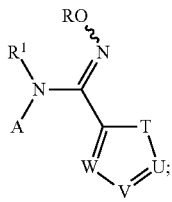

Formula (XIVb)

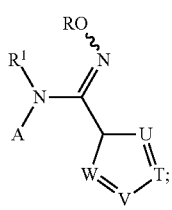

Formula (XIVc)

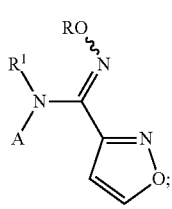

Formula (XIVd)

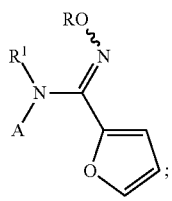

Formula (XIVe)

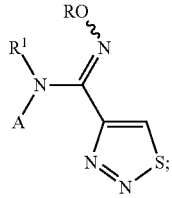

Formula (XIVf)

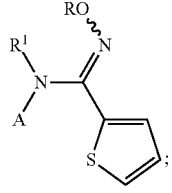

Formula (XIVg)

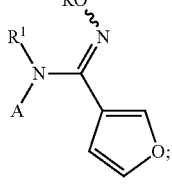

Formula (XIVh)
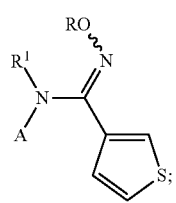

Formula (XIVi)
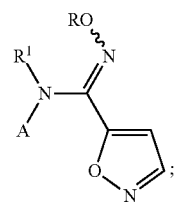

Formula (XIVj)
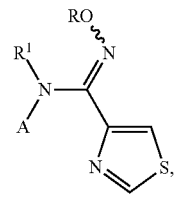

Formula (XIVk)
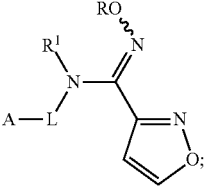

Formula (XIVl)
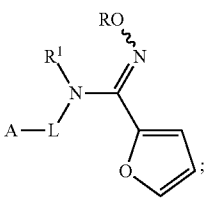

Formula (XIVm)
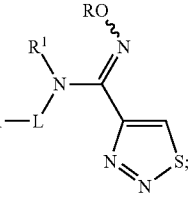

Formula (XIVn)
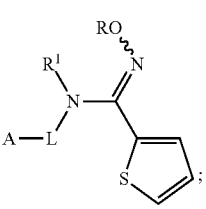

Formula (XIVo)
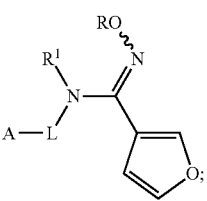

Formula (XIVp)
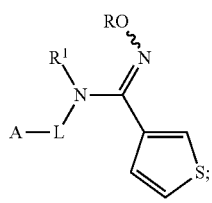

Formula (XIVq)
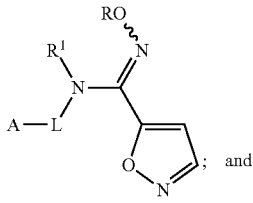

and

Formula (XIVr)
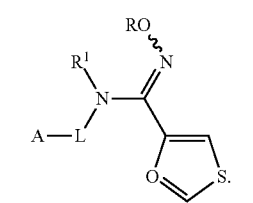

The variable definitions, embodiments, and compound structures are as described in U.S. Patent Publication Number 2008/0146624.

In some embodiments, suitable IDO inhibitors for use in the compositions and methods disclosed herein are the IDO inhibitors described in U.S. Patent Publication Number 2008/0182882, which is hereby incorporated by reference herein in its entirety. In some embodiments, the IDO inhibitor is a compound of Formula (XV), or a pharmaceutically acceptable salt thereof:

Formula (XV)
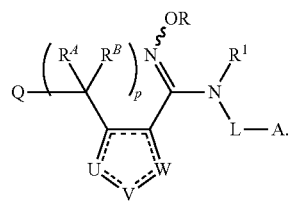

In some embodiments, the IDO inhibitor is a compound of Formula (XVa), Formula (XVb), or a pharmaceutically acceptable salt thereof:

Formula (XVa)
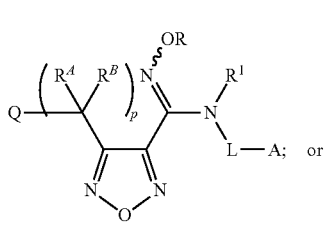

or

Formula (XVb)

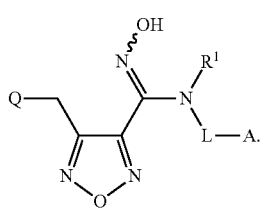

The variable definitions, embodiments, and compound structures are as described in U.S. Patent Publication Number 2008/0182882.

In some embodiments, suitable IDO inhibitors for use in the compositions and methods disclosed herein are the IDO inhibitors described in U.S. Patent Publication Number 2007/0203140, which is hereby incorporated by reference herein in its entirety. In some embodiments, the IDO inhibitor is a compound of Formula (XVI), or a pharmaceutically acceptable salt thereof:

Formula (XVI)

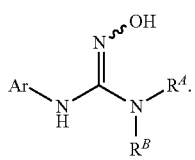

The variable definitions, embodiments, and compound structures are as described in U.S. Patent Publication Number 2007/0203140.

In some embodiments, suitable IDO inhibitors for use in the compositions and methods disclosed herein are the IDO inhibitors described in U.S. Patent Publication Number 2008/0119491. In some embodiments, the IDO inhibitor is a compound of Formula (XVII), or a pharmaceutically acceptable salt thereof:

Formula (XVII)

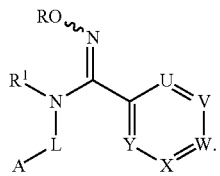

In some embodiments, the IDO inhibitor is a compound selected from one of the following formulas, or a pharmaceutically acceptable salt thereof:

Formula (XVIIa)

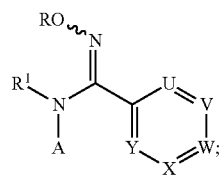

Formula (XVIIb)

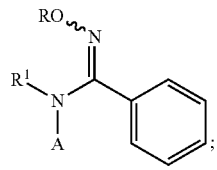

Formula (XVIIc)

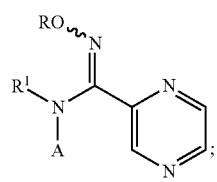

Formula (XVIId)

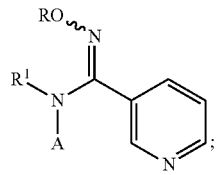

Formula (XVIIe)

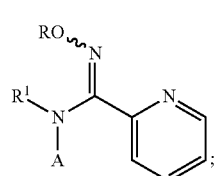

Formula (XVIIf)

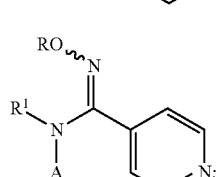

Formula (XVIIg)

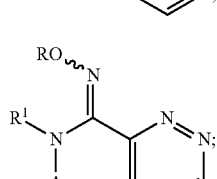

Formula (XVIIh)

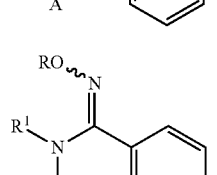

Formula (XVIIi)

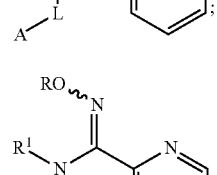

Formula (XVIIj)

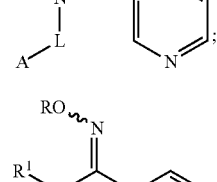
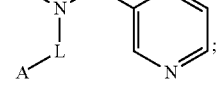

Formula (XVIIk)

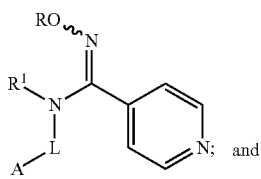

Formula (XVIIl)

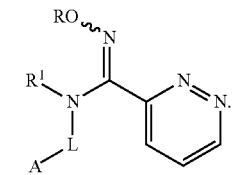
and

Formula (XVIIm)

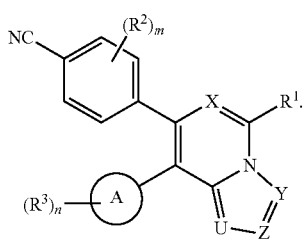

The variable definitions, embodiments, and compound structures are as described in U.S. Patent Publication Number 2008/0119491.

In some embodiments, suitable IDO inhibitors for use in the compositions and methods disclosed herein are the IDO inhibitors described in U.S. Patent Publication Number 2016/0289238, which is hereby incorporated by reference herein in its entirety. In some embodiments, the IDO inhibitor is a compound of Formula (XVIII), or a pharmaceutically acceptable salt thereof:

Formula (XVIII)

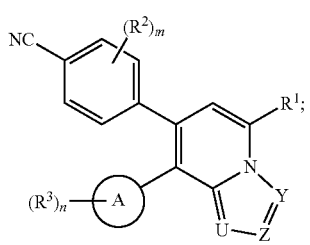

In some embodiments, the IDO inhibitor is a compound selected from one of the following formulas, or a pharmaceutically acceptable salt thereof:

Formula (XVIIIa)

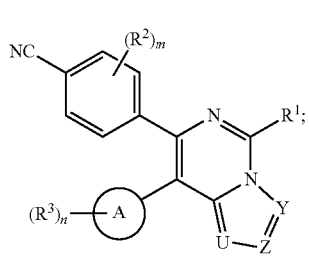

Formula (XVIIIb)

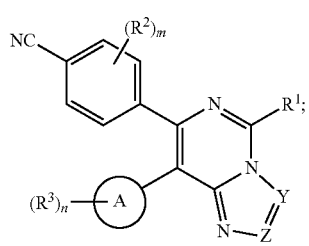

Formula (XVIIIc)

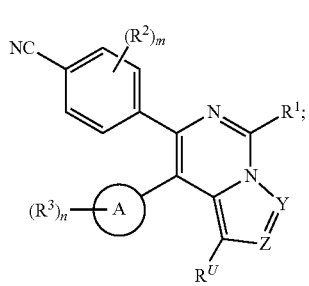

Formula (XVIIId)

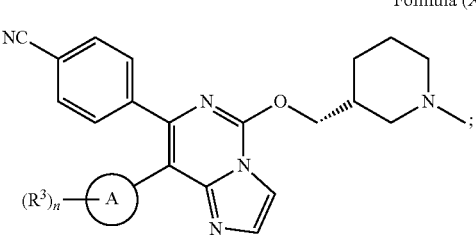

Formula (XVIIIe)

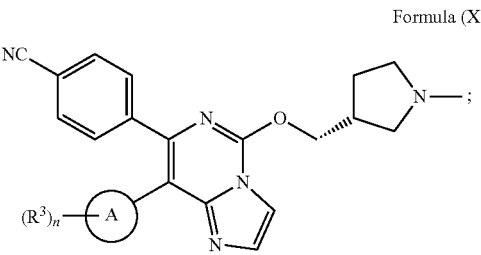

Formula (XVIIIf)

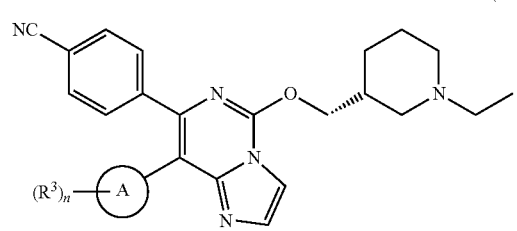

Formula (XVIIIg)

Formula (XVIIIh)

Formula (XVIIIi)

Formula (XVIIIj)

Formula (XVIIIk)

Formula (XVIIIl)

Formula (XVIIIm)

Formula (XVIIIn)

Formula (XVIIIo)

Formula (XVIIIp)

The variable definitions, embodiments, and compound structures are as described in U.S. Patent Publication Number 2016/0289238.

In some embodiments, suitable IDO inhibitors for use in the compositions and methods disclosed herein are the IDO inhibitors described in U.S. Patent Publication Number 2016/0229843, which is hereby incorporated by reference herein in its entirety. In some embodiments, the IDO inhibitor is a compound of Formula (XIX), or a pharmaceutically acceptable salt thereof:

Formula (XIX)

In some embodiments, the IDO inhibitor is a compound selected from one of the following formulas, or a pharmaceutically acceptable salt thereof:

Formula (XIXa)
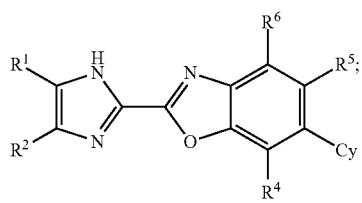
Formula (XIXb)
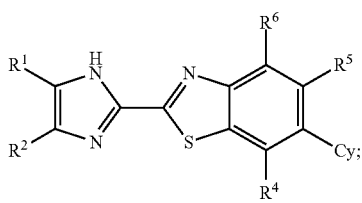
Formula (XIXc)
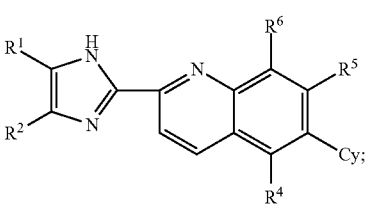
Formula (XIXd)
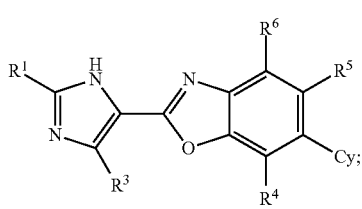
Formula (XIXe)
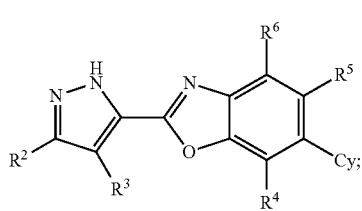
Formula (XIXf)
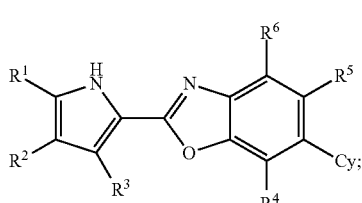
Formula (XIXg)
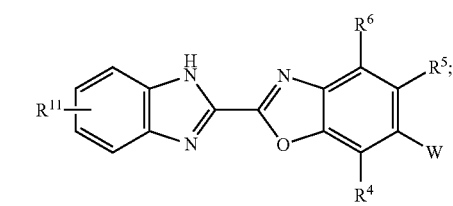
Formula (XIXh)
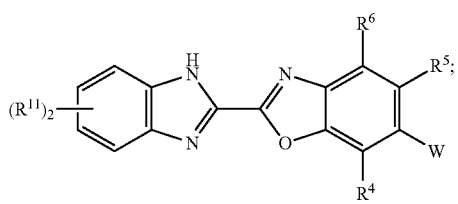
Formula (XIXi)
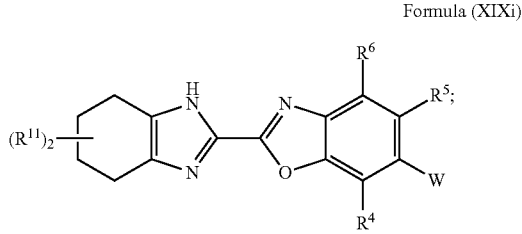
Formula (XIXj)
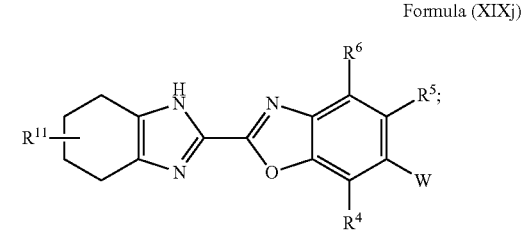
Formula (XIXk)
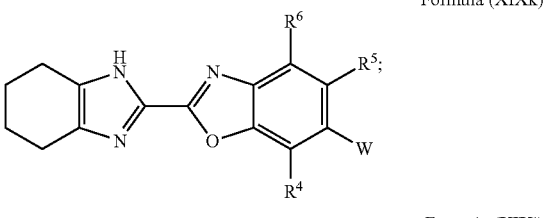
Formula (XIXl)
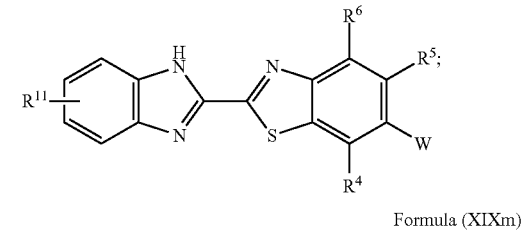
Formula (XIXm)
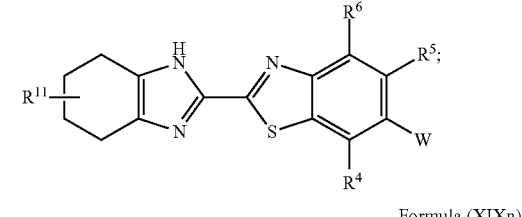
Formula (XIXn)
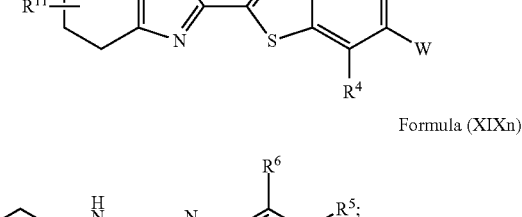

-continued

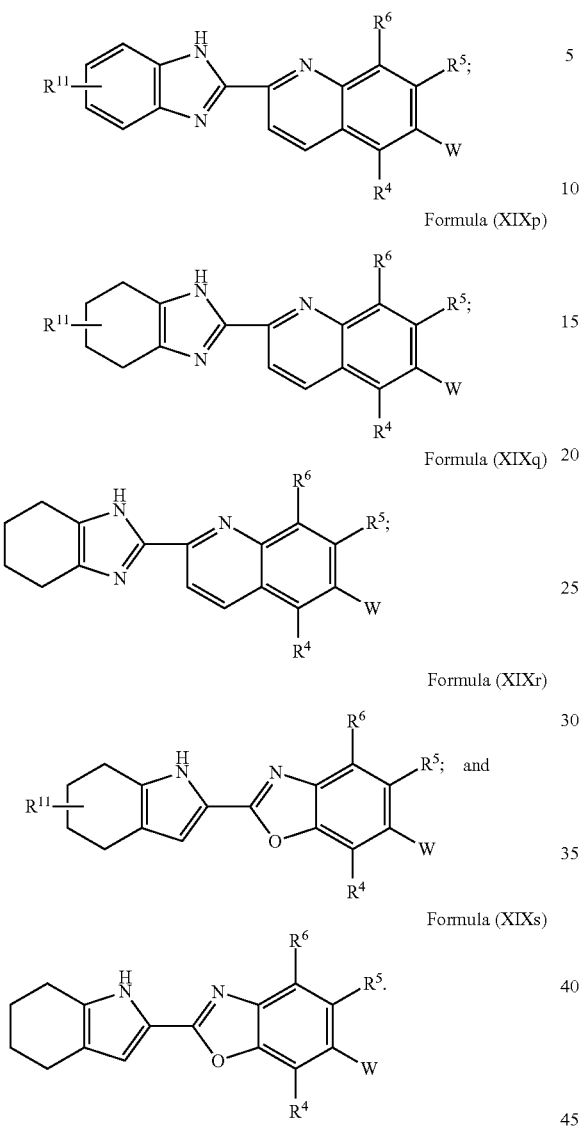

The variable definitions, embodiments, and compound structures are as described in U.S. Patent Publication Number 2016/0229843.

In some embodiments, suitable IDO inhibitors for use in the compositions and methods disclosed herein are the IDO inhibitors described in U.S. Patent Publication Number 2016/0046596, which is hereby incorporated by reference herein in its entirety. In some embodiments, the IDO inhibitor is a compound of Formula (XX), or a pharmaceutically acceptable salt thereof:

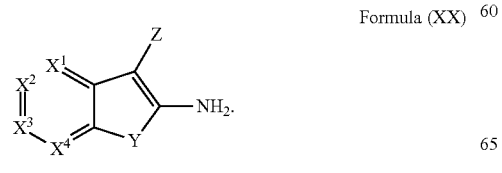

Formula (XX)

In some embodiments, the IDO inhibitor is a compound selected from one of the following formulas, or a pharmaceutically acceptable salt thereof:

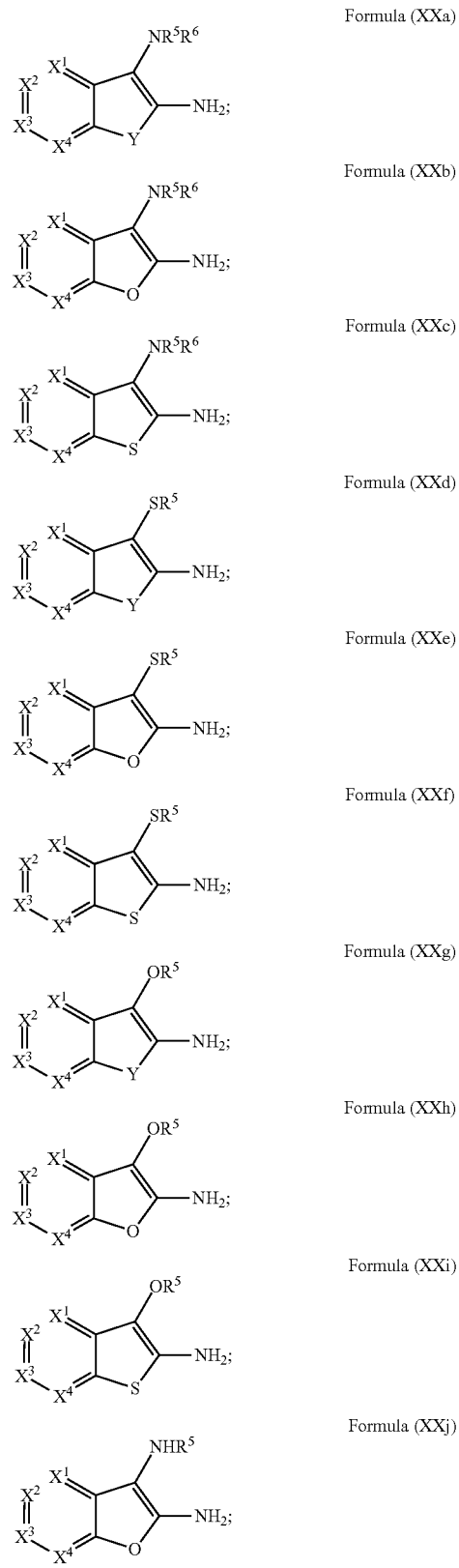

-continued

Formula (XXk)
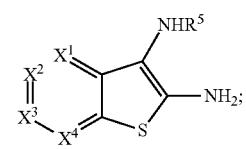

Formula (XXl)
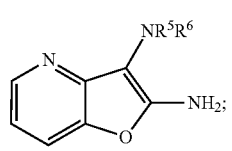

Formula (XXm)
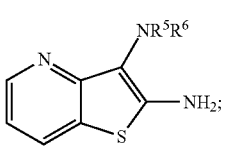

Formula (XXn)
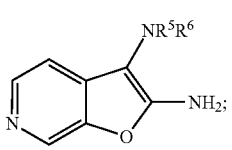

Formula (XXo)
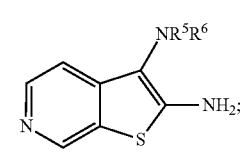

Formula (XXp)
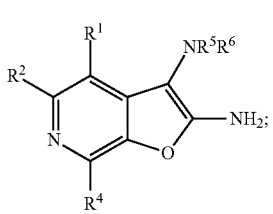

Formula (XXq)
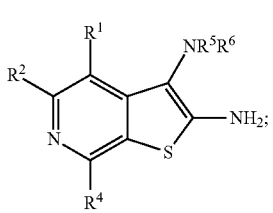

Formula (XXr)
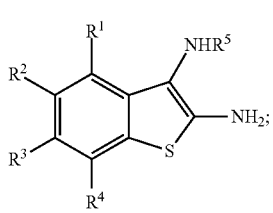

Formula (XXs)
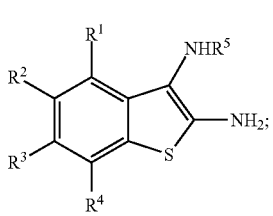

-continued

Formula (XXt)
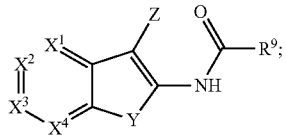

Formula (XXu)
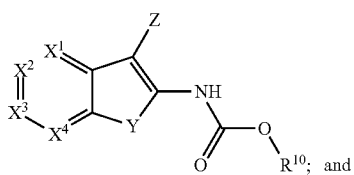

Formula (XXv)
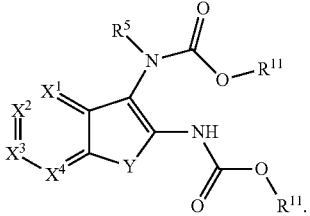

The variable definitions, embodiments, and compound structures are as described in U.S. Patent Publication Number 2016/0046596.

In some embodiments, suitable IDO inhibitors for use in the compositions and methods disclosed herein are the IDO inhibitors described in U.S. Patent Publication Number 2011/0053941 or 2013/0289083, which are hereby incorporated by reference herein in their entireties. In some embodiments, the IDO inhibitor is a compound of Formula (XXI), Formula (XXII) or a pharmaceutically acceptable salt thereof:

Formula (XXI)
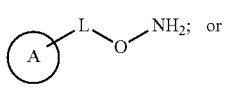

Formula (XXII)
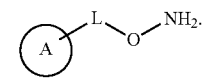

In some embodiments, the IDO inhibitor is a compound selected from one of the following formulas, or a pharmaceutically acceptable salt thereof:

Formula (XXIIIa)
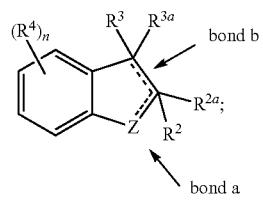

Formula (XXIIIb)
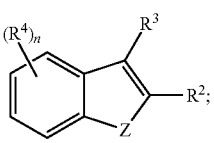

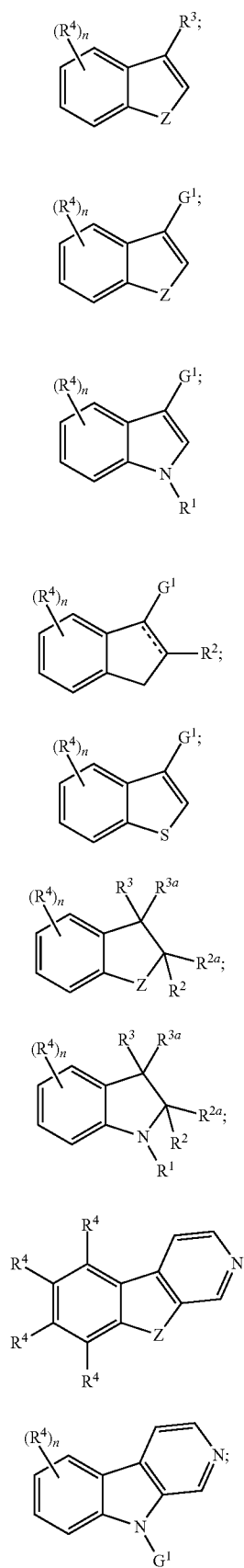
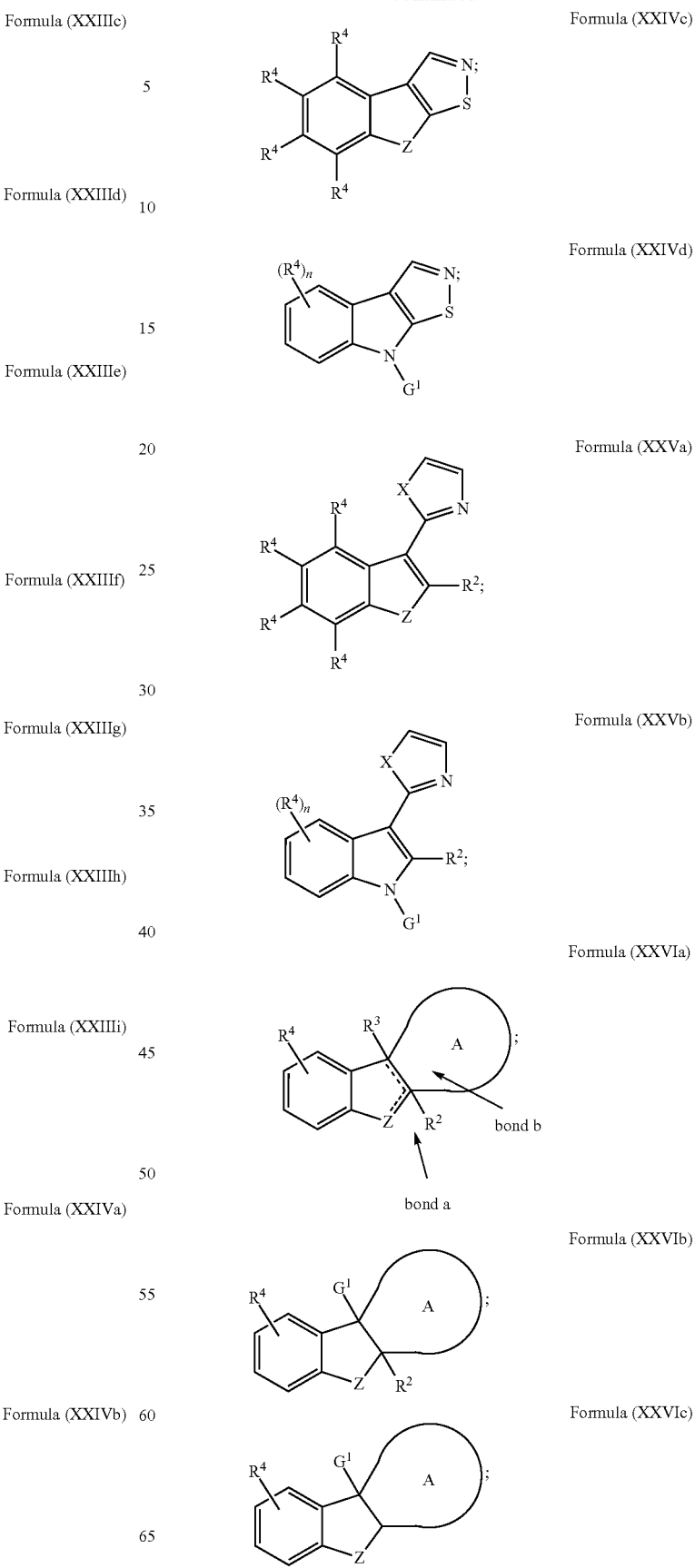

-continued
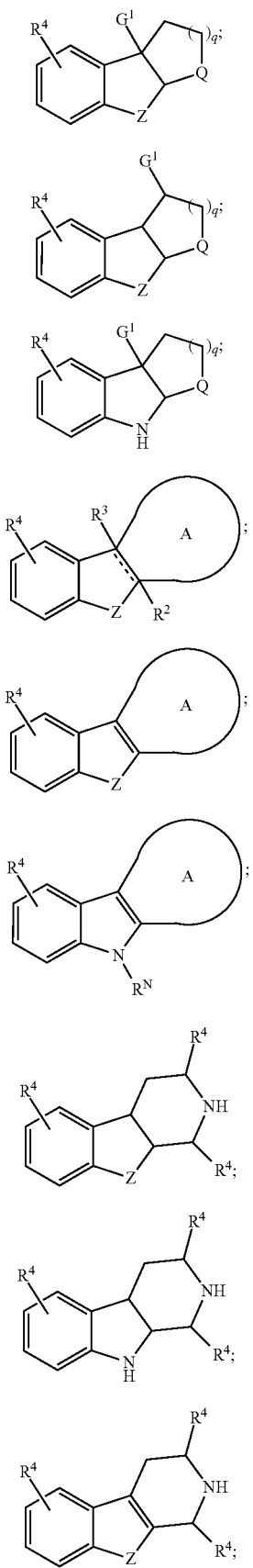
Formula (XXVId)
Formula (XXVIe)
Formula (XXVIf)
Formula (XXVIg)
Formula (XXVIh)
Formula (XXVIi)
Formula (XXVIj)
Formula (XXVIk)
Formula (XXVIl)
-continued
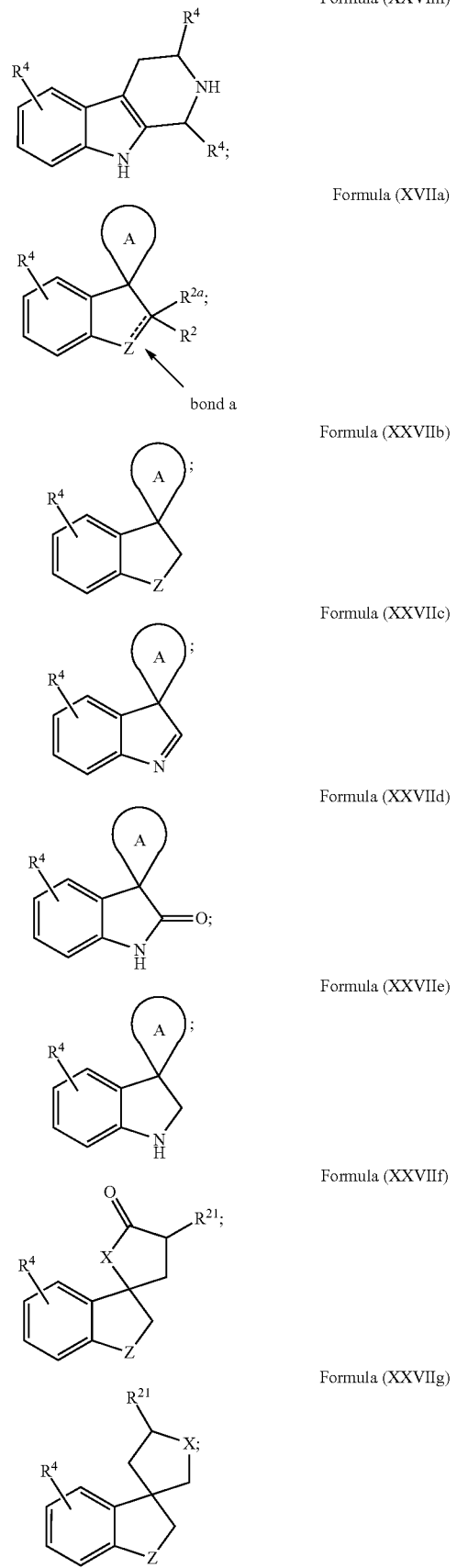
Formula (XXVIm)
Formula (XVIIa)
Formula (XXVIIb)
Formula (XXVIIc)
Formula (XXVIId)
Formula (XXVIIe)
Formula (XXVIIf)
Formula (XXVIIg)

Formula (XXVIIh)
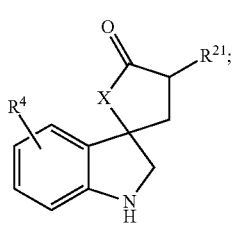
Formula (XXVIIi)
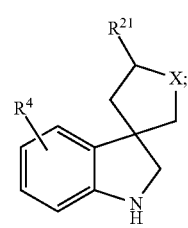
Formula (XXVIIIa)
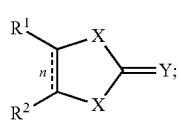
Formula (XXVIIIb)
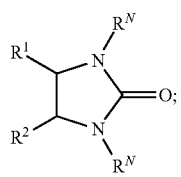
Formula (XXVIIIc)
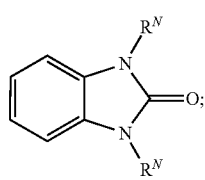
Formula (XXVIIId)
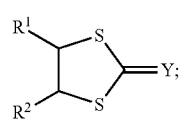
Formula (XXVIIIe)
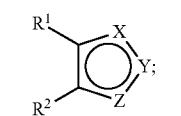
Formula (XXVIIIf)
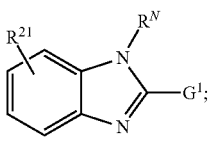
Formula (XXVIIIg)
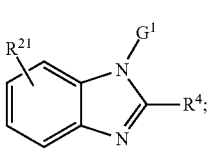
Formula (XXVIIIh)
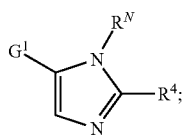
Formula (XXVIIIi)
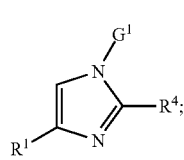
Formula (XXVIIIj)
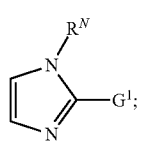
Formula (XXVIIIk)
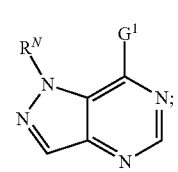
Formula (XXVIIIl)
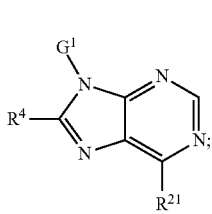
Formula (XXVIIIm)
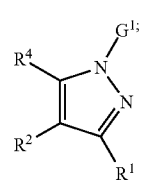
Formula (XXVIIIn)
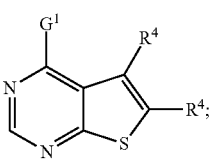
Formula (XXVIIIo)
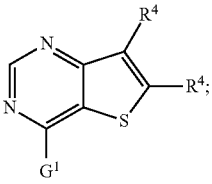
Formula (XXVIIIp)
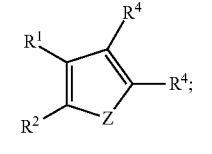
Formula (XXVIIIq)
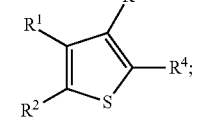

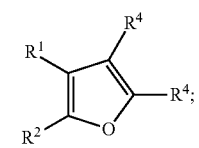
Formula (XXVIIIr)
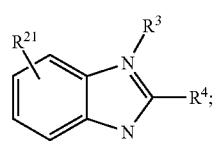
Formula (XXVIIIs)
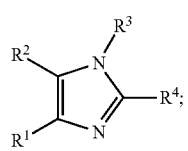
Formula (XXVIIIt)
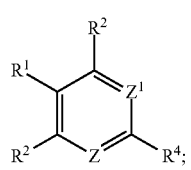
Formula (XXVIIIu)
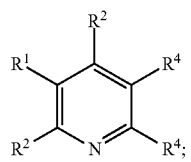
Formula (XXVIIIv)
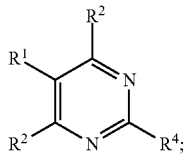
Formula (XXVIIIw)
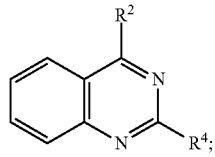
Formula (XXVIIIx)
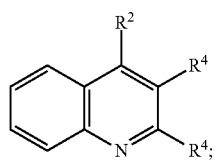
Formula (XXVIIIy)
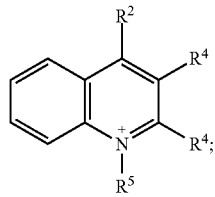
Formula (XXVIIIz)
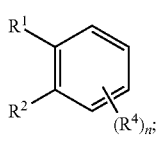
Formula (XXVIIIab)
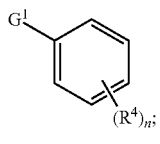
Formula (XXVIIIbn)
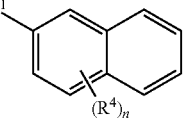
Formula (XXVIIIac)
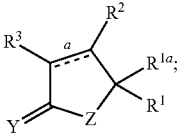
Formula (XXVIIIad)
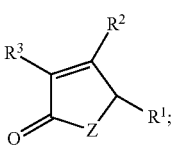
Formula (XXVIIIae)
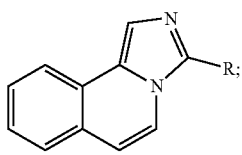
Formula (XXVIIIaf)
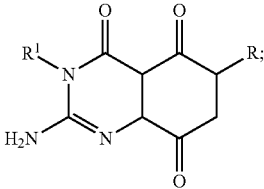
Formula (XXVIIIag)
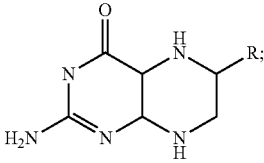
Formula (XXVIIIah)
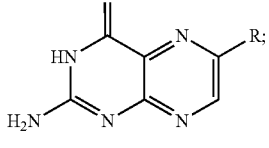
Formula (XXVIIIai)
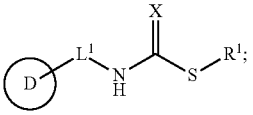
Formula (XXVIIIaj)

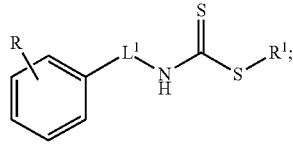
Formula (XXVIIIbw)
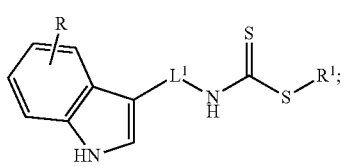
Formula (XXVIIIak)
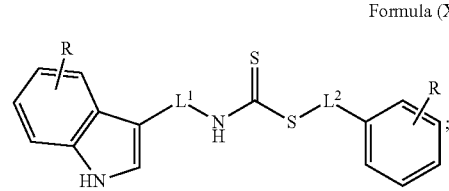
Formula (XXVIIIal)
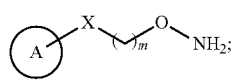
Formula (XXVIIIam)
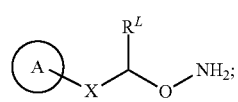
Formula (XXVIIIan)
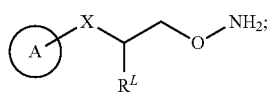
Formula (XXVIIIao)
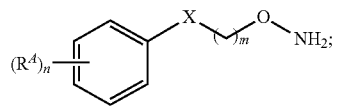
Formula (XXVIIIap)
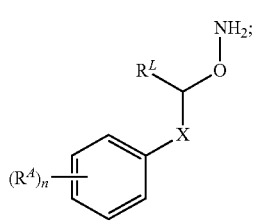
Formula (XXVIIIaq)
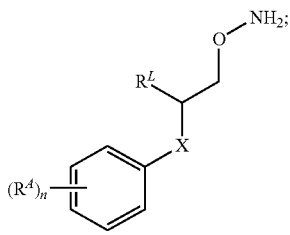
Formula (XXVIIIar)
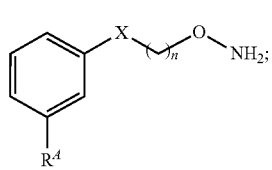
Formula (XXVIIIas)
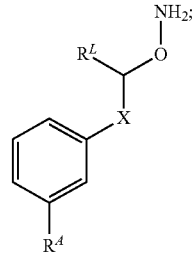
Formula (XXVIIIat)
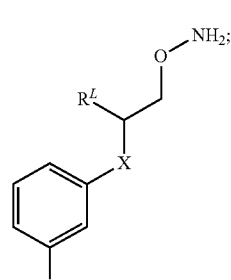
Formula (XXVIIIau)
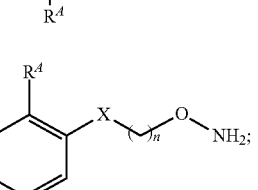
Formula (XXVIIIav)
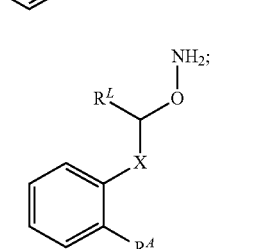
Formula (XXVIIIaw)
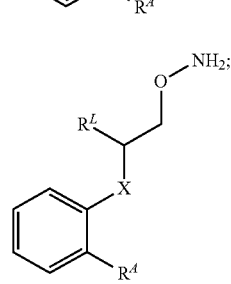
Formula (XXVIIIax)
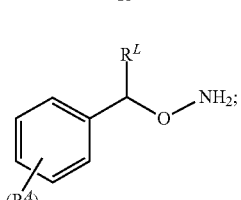
Formula (XXVIIIay)
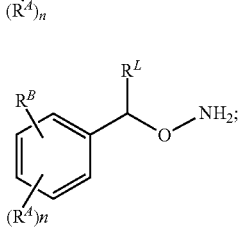
Formula (XXVIIIaz)

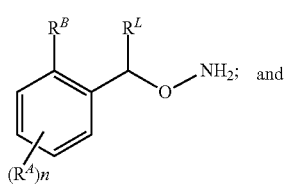
Formula (XXVIIIba)

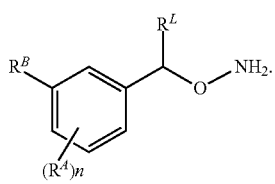
Formula (XXVIIIbb)

The variable definitions, embodiments, and compound structures are as described in U.S. Patent Publication Number 2011/0053941 or 2013/0289083.

In some embodiments, suitable IDO inhibitors for use in the compositions and methods disclosed herein are the IDO inhibitors described in U.S. Patent Publication Number 2016/0060266, which is hereby incorporated by reference herein in its entirety. In some embodiments, the IDO inhibitor is a compound of Formula (XXIX), or a pharmaceutically acceptable salt thereof:

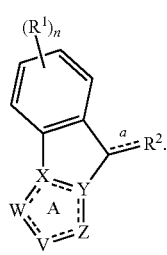
Formula (XXIX)

In some embodiments, the IDO inhibitor is a compound selected from the following formulas, or a pharmaceutically acceptable salt thereof:

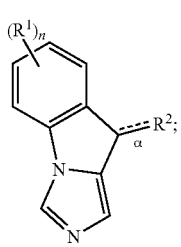
Formula (XXIXa)

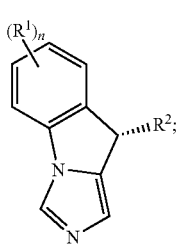
Formula (XXIXb)

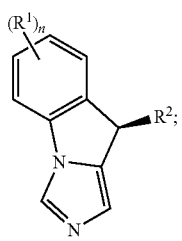
Formula (XXIXc)

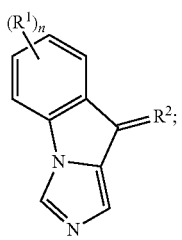
Formula (XXIXd)

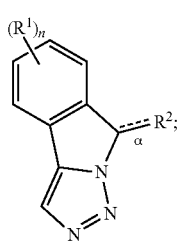
Formula (XXIXe)

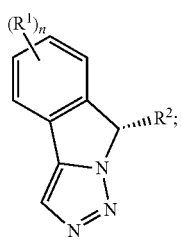
Formula (XXIXf)

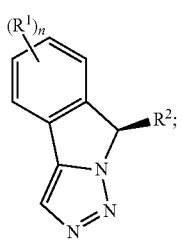
Formula (XXIXg)

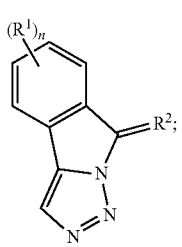
Formula (XXIXh)

Formula (XXIXi)

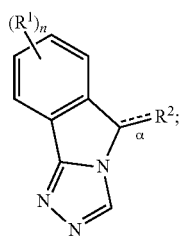

Formula (XXIXj)

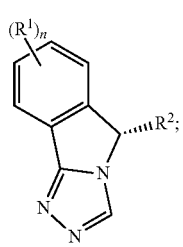

Formula (XXIXk)

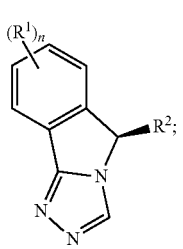

Formula (XXIXl)

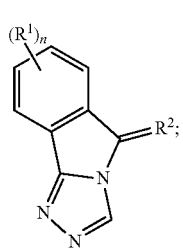

Formula (XXIXm)

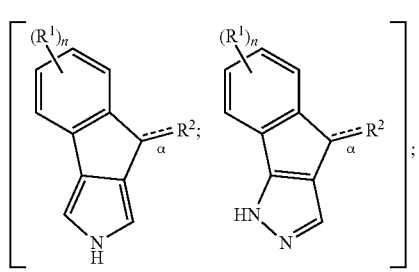

Formula (XXIXn)

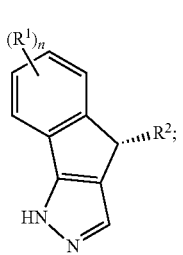

Formula (XXIXo)

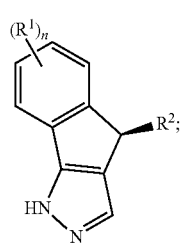

Formula (XXIXp)

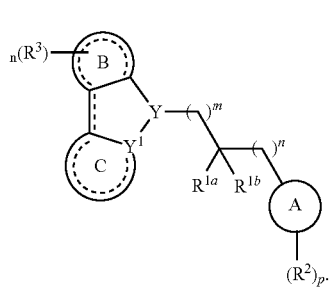

The variable definitions, embodiments, and compound structures are as described in U.S. Patent Publication Number 2016/0060266.

In some embodiments, suitable IDO inhibitors for use in the compositions and methods disclosed herein are the IDO inhibitors described in U.S. Patent Publication Number 2016/075711, which is hereby incorporated by reference herein in its entirety. In some embodiments, the IDO inhibitor is a compound of Formula (XXX), or a pharmaceutically acceptable salt thereof:

Formula (XXX)

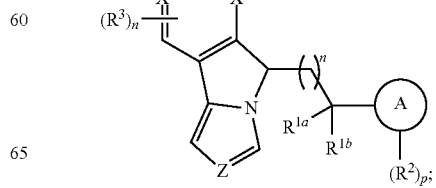

In some embodiments, the IDO inhibitor is a compound selected from a compound of the following formulas, or a pharmaceutically acceptable salt thereof:

Formula (XXXa)

-continued
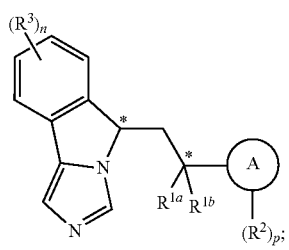
Formula (XXXb)
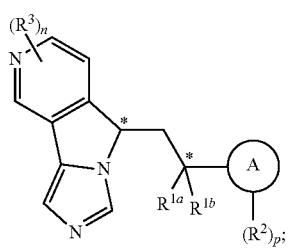
Formula (XXXc)
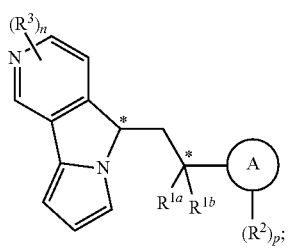
Formula (XXXd)
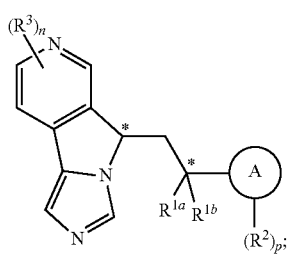
Formula (XXXe)
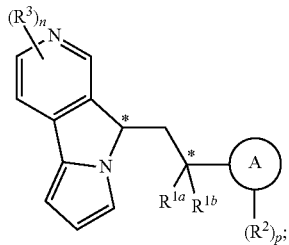
Formula (XXXf)
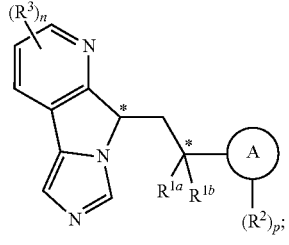
Formula (XXXg)
-continued
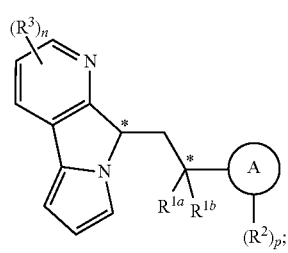
Formula (XXXh)
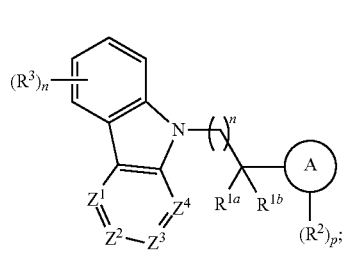
Formula (XXXi)
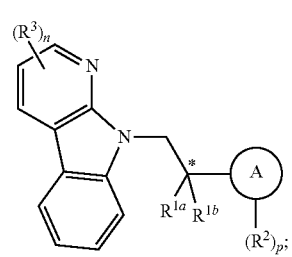
Formula (XXXj)
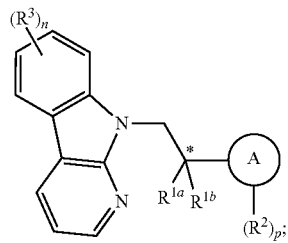
Formula (XXXk)
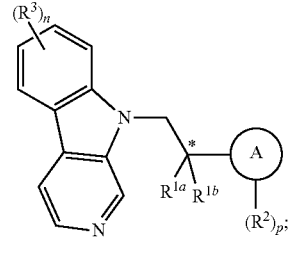
Formula (XXXl)
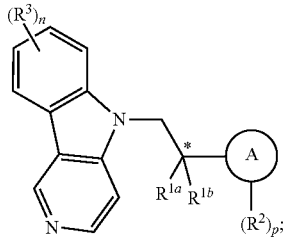
Formula (XXXm)

Formula (XXXn)
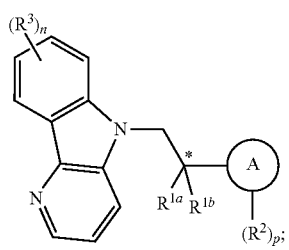
Formula (XXXo)
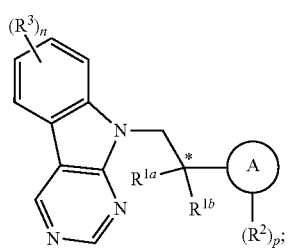
Formula (XXXp)
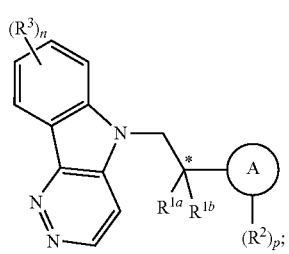
Formula (XXXq)
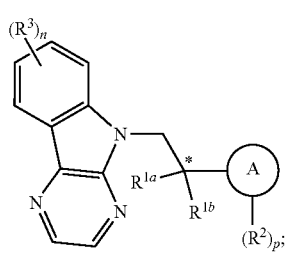
Formula (XXXr)
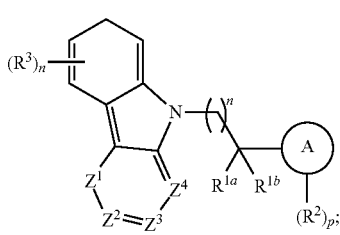
Formula (XXXs)
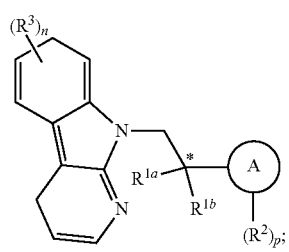
Formula (XXXt)
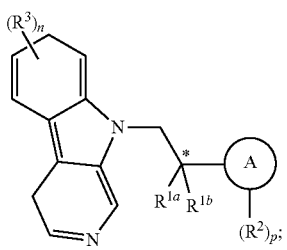
Formula (XXXu)
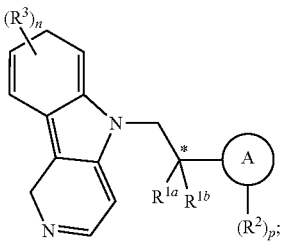
Formula (XXXv)
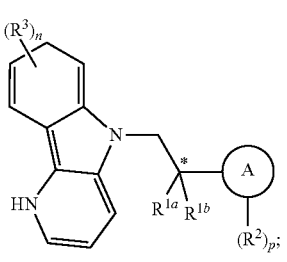
Formula (XXXw)
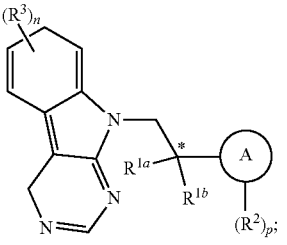
Formula (XXXx)
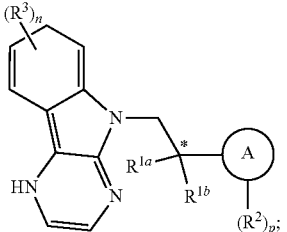
Formula (XXXy)
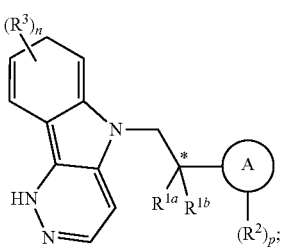

Formula (XXXz)

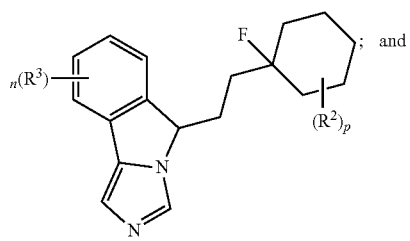

; and

Formula (XXXab)

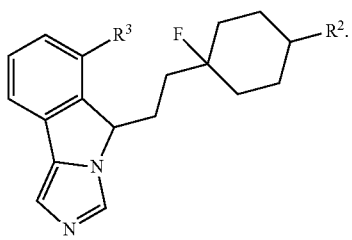

The variable definitions, embodiments, and compound structures are as described in U.S. Patent Publication Number 2016/075711.

In some embodiments, suitable IDO inhibitors for use in the compositions and methods disclosed herein are the IDO inhibitors described in U.S. Patent Publication Number 2016/0022619, which is hereby incorporated by reference herein in its entirety. In some embodiments, the IDO inhibitor is a compound of Formula (XXXI), a compound of Formula (XXXII), or a pharmaceutically acceptable salt thereof:

Formula (XXXI)

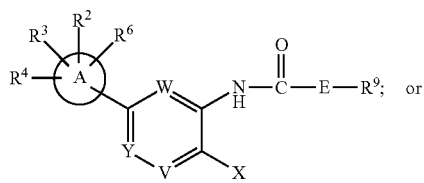

Formula (XXXII)

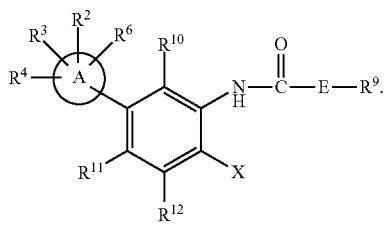

The variable definitions, embodiments, and compound structures are as described in U.S. Patent Publication Number 2016/0022619.

In some embodiments, suitable IDO inhibitors for use in the compositions and methods disclosed herein are the IDO inhibitors described in U.S. Patent Publication Number 2016/0060237, which is hereby incorporated by reference herein in its entirety. In some embodiments, the IDO inhibitor is a compound of Formula (XXXIII), a compound of Formula (XXXIV), or a pharmaceutically acceptable salt thereof:

Formula (XXXIII)

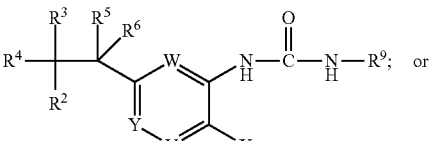

Formula (XXXIV)

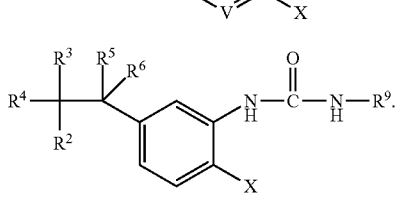

The variable definitions, embodiments, and compound structures are as described in U.S. Patent Publication Number 2016/0060237.

In some embodiments, suitable IDO inhibitors for use in the compositions and methods disclosed herein are the IDO inhibitors described in U.S. Patent Publication Number 2016/0137595, which is hereby incorporated by reference herein in its entirety. In some embodiments, the IDO inhibitor is a compound of Formula (XXXV), a compound of Formula (XXXVI), or a pharmaceutically acceptable salt thereof:

Formula (XXXV)

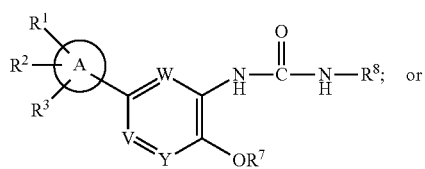

Formula (XXXVI)

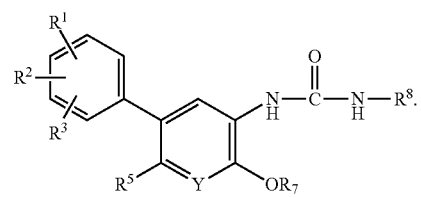

The variable definitions, embodiments, and compound structures are as described in U.S. Patent Publication Number 2016/0137595.

In some embodiments, suitable IDO inhibitors for use in the compositions and methods disclosed herein are the IDO inhibitors described in U.S. Patent Publication Number 2016/0143870, which is hereby incorporated by reference herein in its entirety. In some embodiments, the IDO inhibitor is a compound of Formula (XXXVII), a compound of Formula (XXXVIII), or a pharmaceutically acceptable salt thereof:

Formula (XXXVII)

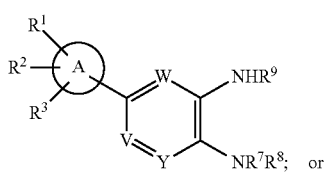

Formula (XXXVIII)

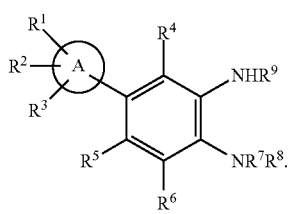

The variable definitions, embodiments, and compound structures are as described in U.S. Patent Publication Number 2016/0143870.

In some embodiments, suitable IDO inhibitors for use in the compositions and methods disclosed herein are the IDO inhibitors described in U.S. Patent Publication Number 2016/0200674, which is hereby incorporated by reference herein in its entirety. In some embodiments, the IDO inhibitor is a compound of Formula (XXXIX), a compound of Formula (XL), or a pharmaceutically acceptable salt thereof:

Formula (XXXIX)

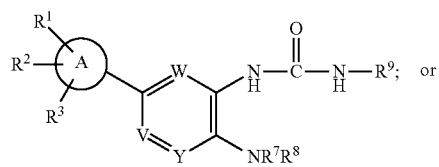

Formula (XL)

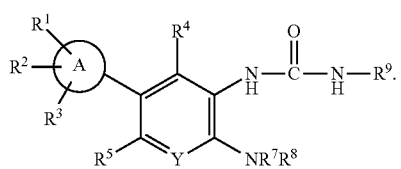

The variable definitions, embodiments, and compound structures are as described in U.S. Patent Publication Number 2016/0200674.

In some embodiments, suitable IDO inhibitors for use in the compositions and methods disclosed herein are the IDO inhibitors described in U.S. Patent Publication Number 2016/0289171, which is hereby incorporated by reference herein in its entirety. In some embodiments, the IDO inhibitor is a compound of Formula (XLI), a compound of Formula (XLII), or a pharmaceutically acceptable salt thereof:

Formula (XLI)

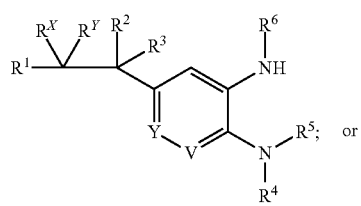

Formula (XLII)

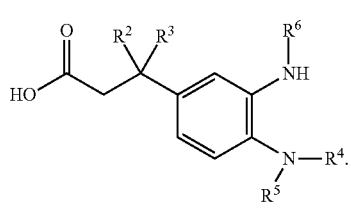

The variable definitions, embodiments, and compound structures are as described in U.S. Patent Publication Number 2016/0289171.

In some embodiments, suitable IDO inhibitors for use in the compositions and methods disclosed herein are the IDO inhibitors described in U.S. Patent Publication Number 2016/0137652, which is hereby incorporated by reference herein in its entirety. In some embodiments, the IDO inhibitor is a compound of Formula (XLIII), or a pharmaceutically acceptable salt thereof:

Formula (XLIII)

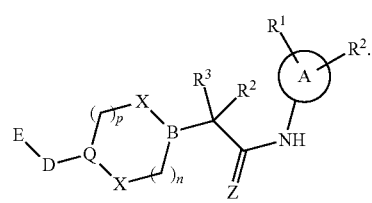

In some embodiments, the IDO inhibitor is a compound selected from one of the following formulas, or a pharmaceutically acceptable salt thereof:

Formula (XLIIIa)

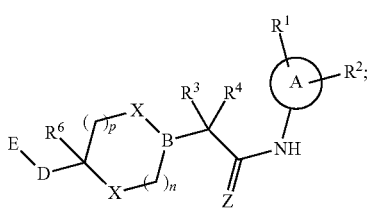

Formula (XLIIIb)

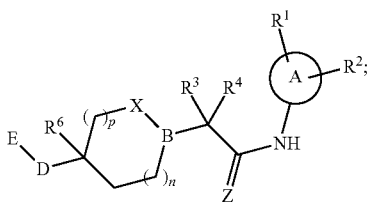

Formula (XLIIIc)

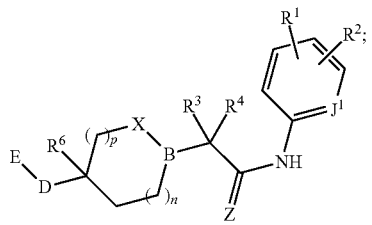

-continued

Formula (XLIIId)
Formula (XLIIIe)
Formula (XLIIIf)
Formula (XLIIIg)
Formula (XLIIIh)
Formula (XLIIIi)

Formula (XLIIIj)
Formula (XLIIIk)
Formula (XLIIIl)
Formula (XLIIIm)
Formula (XLIIIn)

Formula (XLIIIo)
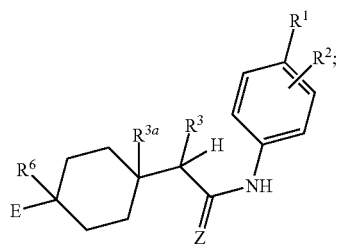

Formula (XLIIIp)
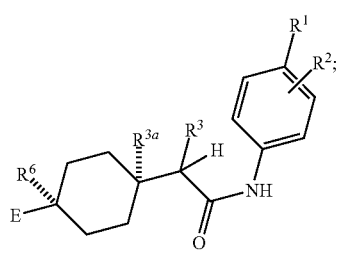

Formula (XLIIIq)
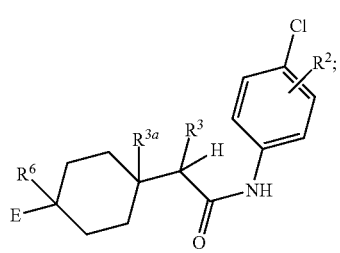

Formula (XLIIIr)
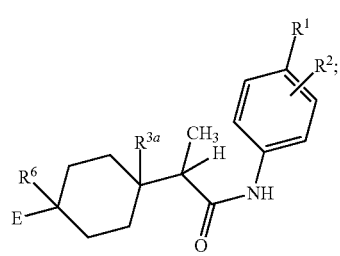

Formula (XLIIIs)
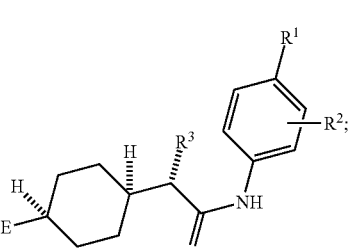

Formula (XLIIIt)
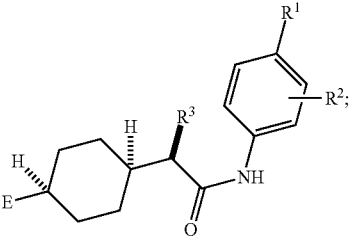

Formula (XLIIIu)
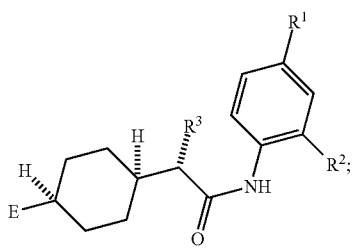

Formula (XLIIIv)
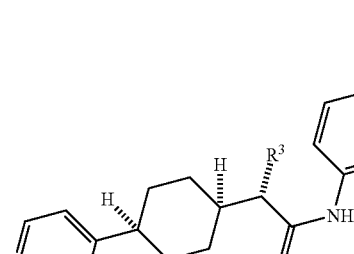

Formula (XLIIIw)
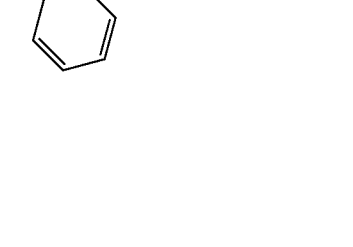

and

Formula (XLIIIx)
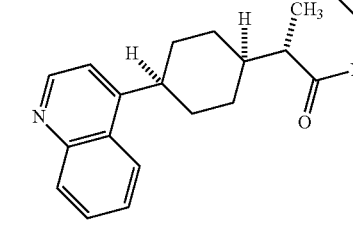

The variable definitions, embodiments, and compound structures are as described in U.S. Patent Publication Number 2016/0137652.

In some embodiments, suitable IDO inhibitors for use in the compositions and methods disclosed herein are the IDO inhibitors described in U.S. Patent Publication Number 2016/0137653, which is hereby incorporated by reference herein in its entirety. In some embodiments, the IDO inhibitor is a compound of Formula (XLIV), or a pharmaceutically acceptable salt thereof:

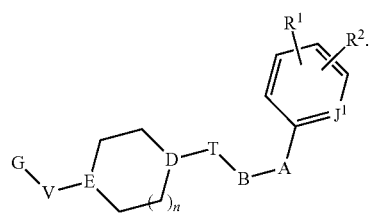
Formula (XLIV)
In some embodiments, the IDO inhibitor is a compound selected from one of the following formulas, or a pharmaceutically acceptable salt thereof:
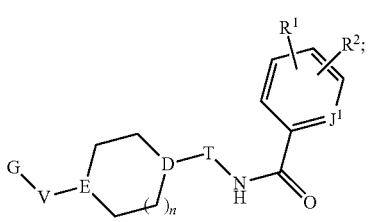
Formula (XLIVa)
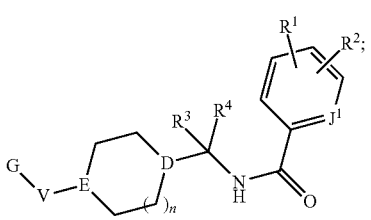
Formula (XLIVb)
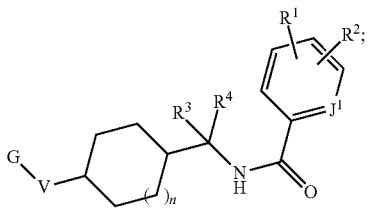
Formula (XLIVc)
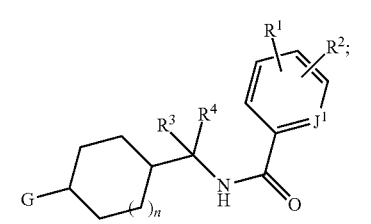
Formula (XLIVd)
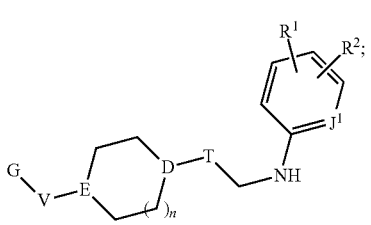
Formula (XLIVe)
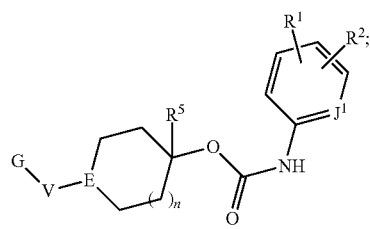
Formula (XLIVf)
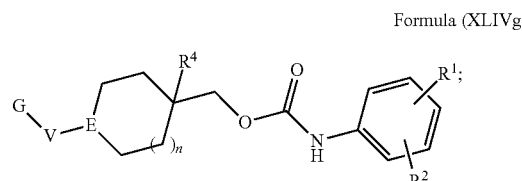
Formula (XLIVg)
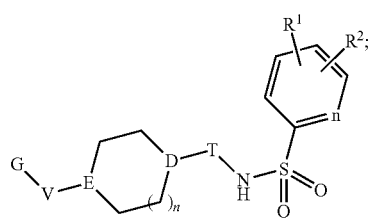
Formula (XLIVh)
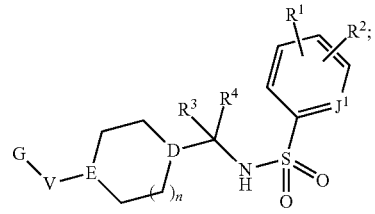
Formula (XLIVi)
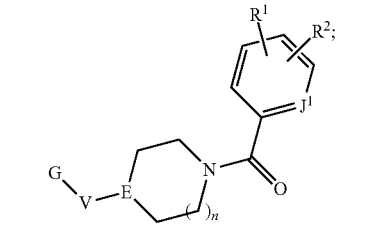
Formula (XLIVj)
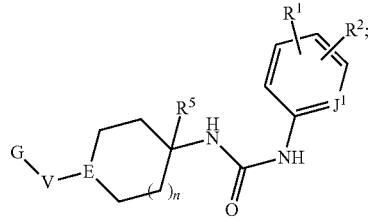
Formula (XLIVk)
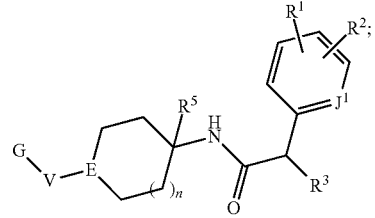
Formula (XLIVl)

Formula (XLIVm)

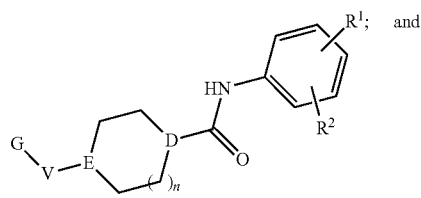

and

Formula (XLIVn)

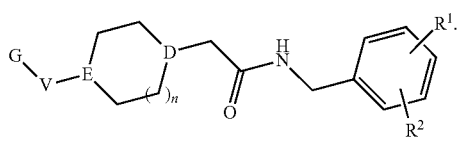

The variable definitions, embodiments, and compound structures are as described in U.S. Patent Publication Number 2016/0137653.

In some embodiments, suitable IDO inhibitors for use in the compositions and methods disclosed herein are the IDO inhibitors described in PCT Application Publication Number WO2014141110, which is hereby incorporated by reference herein in its entirety. In some embodiments, the IDO inhibitor is a compound of Formula (XLV), or a pharmaceutically acceptable salt thereof:

Formula (XLV)

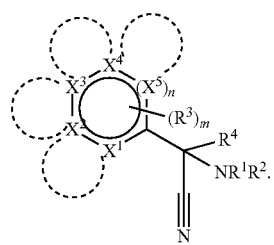

In some embodiments, the IDO inhibitor is a compound selected from one of the following formulas, or a pharmaceutically acceptable salt thereof:

Formula (XLVa)

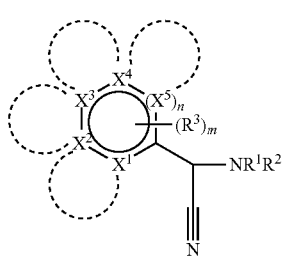

Formula (XLVb)

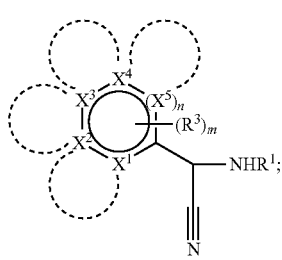

Formula (XLVc)

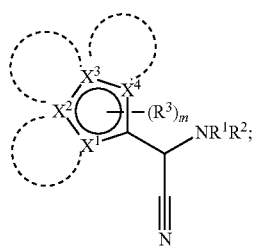

Formula (XLVd)

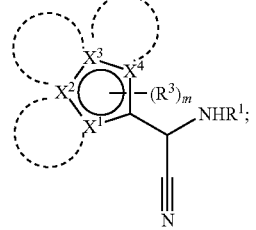

Formula (XLVe)

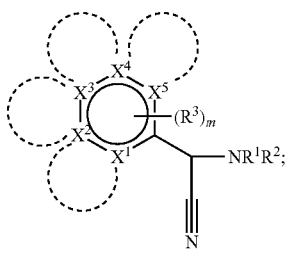

Formula (XLVf)

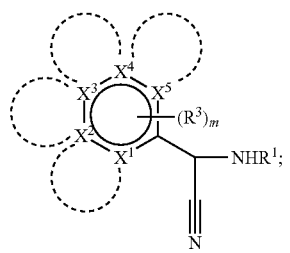

Formula (XLVg)

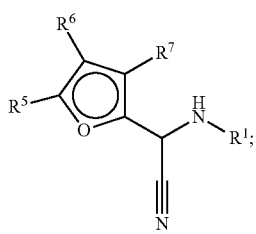

Formula (XLVh)

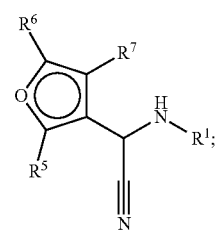

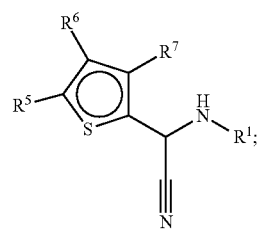
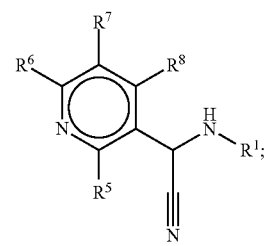

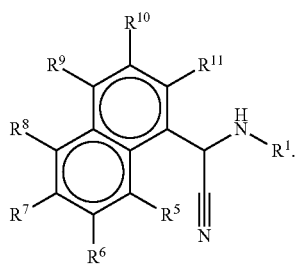

Formula (XLVw)

The variable definitions, embodiments, and compound structures are as described in PCT Application Publication Number WO2014141110.

In some embodiments, suitable IDO inhibitors for use in the compositions and methods disclosed herein are the IDO inhibitors described in PCT Application Publication Number WO2016027241, which is hereby incorporated by reference herein in its entirety. In some embodiments, the IDO inhibitor is a compound of Formula (XLVI), or a pharmaceutically acceptable salt thereof:

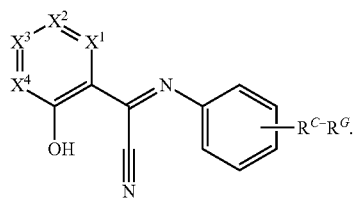

Formula (XLVI)

In some embodiments, the IDO inhibitor is a compound selected from one of the following formulas, or a pharmaceutically acceptable salt thereof:

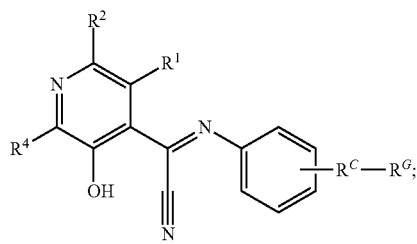

Formula (XLVIa)

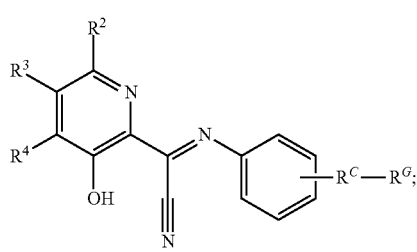

Formula (XLVIb)

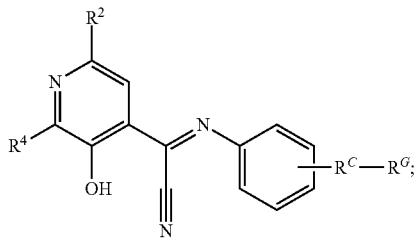

Formula (XLVIc)

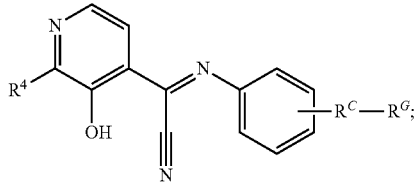

Formula (XLVId)

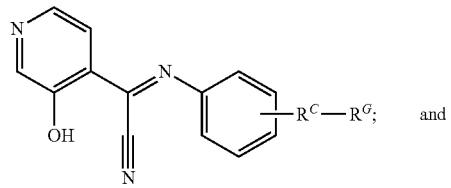

Formula (XLVIe)

and

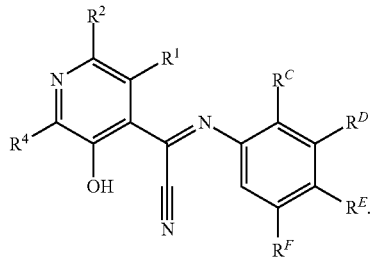

Formula (XLVIf)

The variable definitions, embodiments, and compound structures are as described in PCT Application Publication Number WO2016027241.

In some embodiments, suitable IDO inhibitors for use in the compositions and methods disclosed herein are the IDO inhibitors described in PCT Application Publication Number WO2016181348, which is hereby incorporated by reference herein in its entirety. In some embodiments, the IDO inhibitor is a compound of Formula (XLVII), or a pharmaceutically acceptable salt thereof:

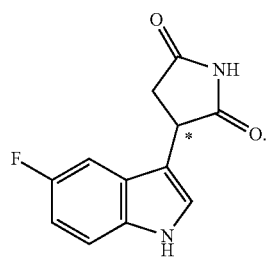

Formula (XLVII)

In some embodiments, the IDO inhibitor is a compound selected from one of the following formulas, or a pharmaceutically acceptable salt thereof:

Formula (XLVIIa)

Formula (XLVIIb)

Formula (XLVIIc)

Formula (XLVIId)

Formula (XLVIIe)

The variable definitions, embodiments, and compound structures are as described in PCT Application Publication Number WO2016181348.

In some embodiments, suitable IDO inhibitors for use in the compositions and methods disclosed herein are the IDO inhibitors described in PCT Application Publication Number WO2016051181, which is hereby incorporated by reference herein in its entirety. In some embodiments, the IDO inhibitor is a compound of Formula (XLIX), or a pharmaceutically acceptable salt thereof:

Formula (XLIX)

In some embodiments, the IDO inhibitor is a compound selected from one of the following formulas, or a pharmaceutically acceptable salt thereof:

Formula (XLIXa)

Formula (XLIXb)

Formula (XLIXc)

Formula (XLIXd)

-continued

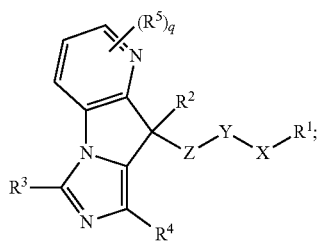
Formula (XLIXe)

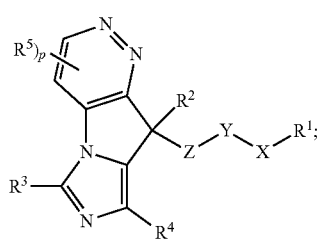
Formula (XLIXf)

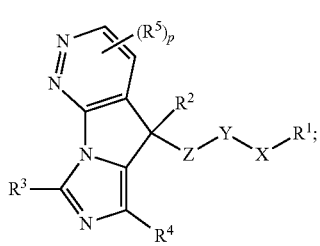
Formula (XLIXg)

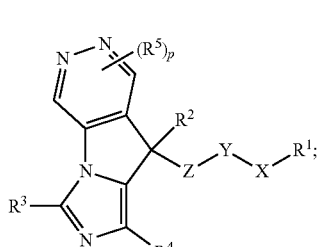
Formula (XLIXh)

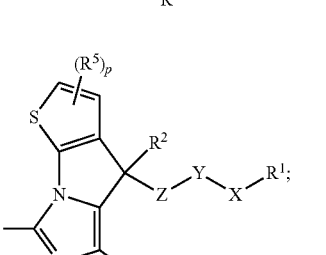
Formula (XLIXi)

and

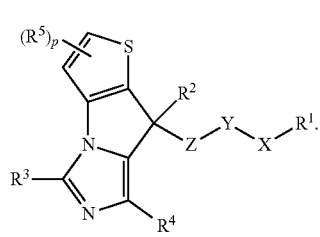
Formula (XLIXj)

The variable definitions, embodiments, and compound structures are as described in PCT Application Publication Number WO2016051181.

In some embodiments, suitable IDO inhibitors for use in the compositions and methods disclosed herein are the IDO inhibitors described in PCT Application Publication Number WO2016059412, which is hereby incorporated by reference herein in its entirety. In some embodiments, the IDO inhibitor is a compound of Formula (L), or a pharmaceutically acceptable salt thereof:

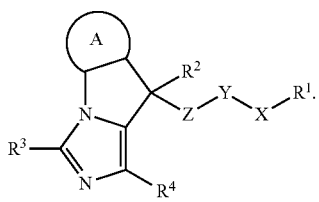
Formula (L)

In some embodiments, the IDO inhibitor is a compound selected from the following formulas, or a pharmaceutically acceptable salt thereof:

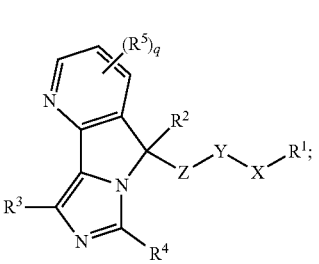
Formula (La)

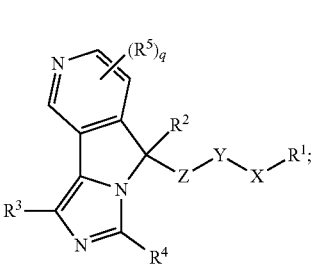
Formula (Lb)

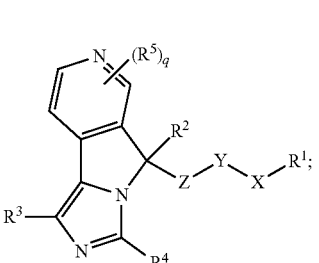
Formula (Lc)

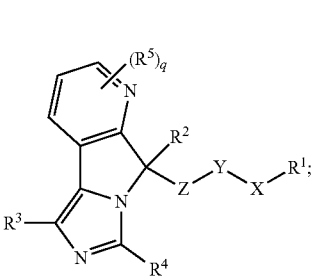
Formula (Ld)

Formula (Le)
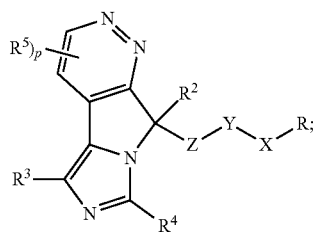

Formula (Lf)
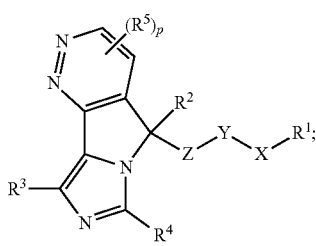

Formula (Lg)
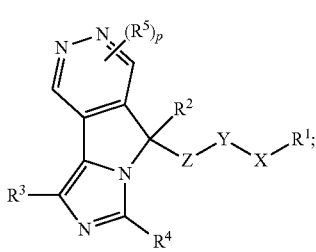

Formula (Lh)
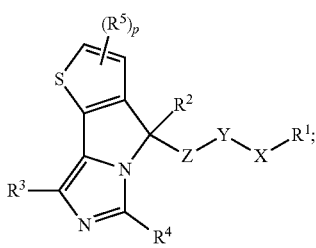

Formula (Li)
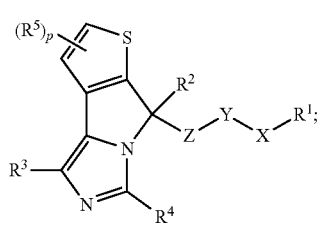

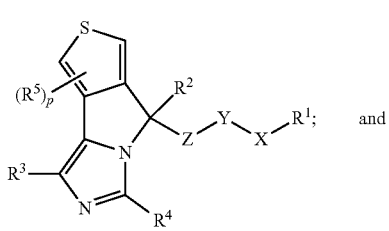 and

Formula (Lk)
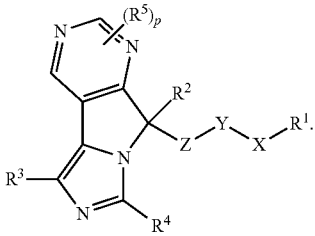

The variable definitions, embodiments, and compound structures are as described in PCT Application Publication Number WO2016059412.

In some embodiments, suitable IDO inhibitors for use in the compositions and methods disclosed herein are the IDO inhibitors described in PCT Application Publication Number WO2015119944, which corresponds to European Patent Publication Number: EP3102237, which are hereby incorporated by reference herein in their entireties. In some embodiments, the IDO inhibitor is a compound of Formula (LI), or a pharmaceutically acceptable salt thereof:

Formula (LI)
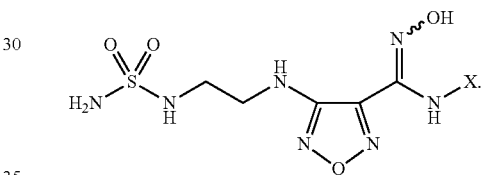

In some embodiments, the IDO inhibitor is a compound selected from Formula (LII) and Formula (LIII), or a pharmaceutically acceptable salt thereof:

Formula (LII)
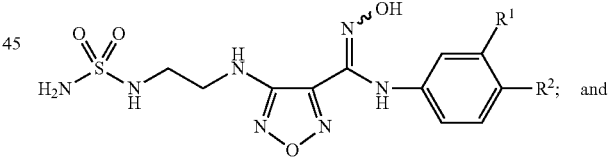
and

Formula (LIII)
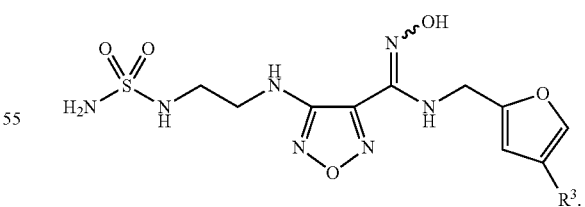

The variable definitions, embodiments, and compound structures are as described in PCT Application Publication Number WO2015119944.

In some embodiments, suitable IDO inhibitors for use in the compositions and methods disclosed herein are the IDO inhibitors described in PCT Application Publication Number WO2016073738, which is hereby incorporated by reference herein in its entirety. In some embodiments, the IDO inhibitor is a compound of Formula (LIV), or a pharmaceutically acceptable salt thereof:

Formula (LIV)

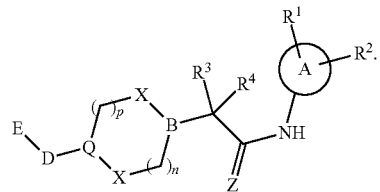

In some embodiments, the IDO inhibitor is a compound selected from one of the following formulas, or a pharmaceutically acceptable salt thereof:

Formula (LIVa)

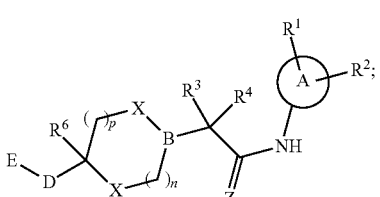

Formula (LIVb)

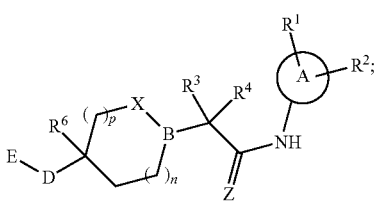

Formula (LIVc)

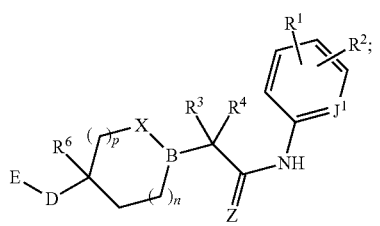

Formula (LIVd)

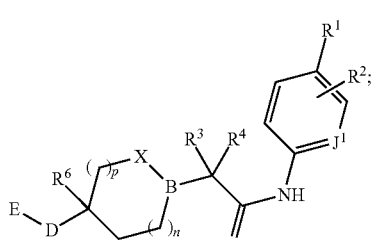

Formula (LIVe)

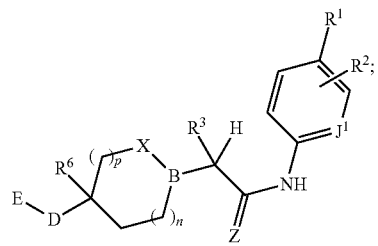

Formula (LIVf)

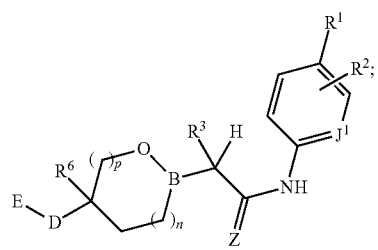

Formula (LIVg)

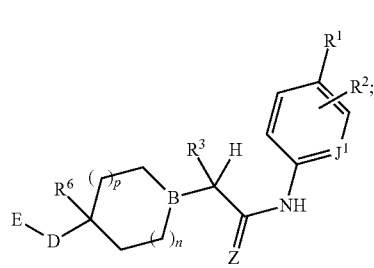

Formula (LIVh)

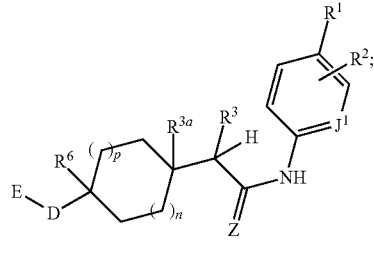

Formula (LIVi)

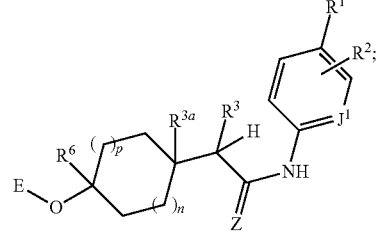

Formula (LIVj)

Formula (LIVk)
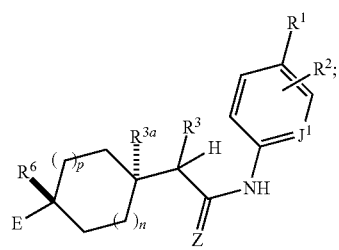
Formula (LIVl)
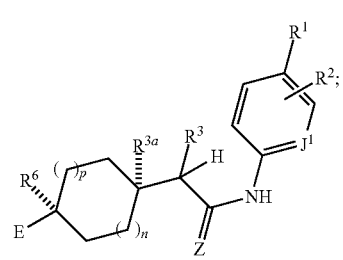
Formula (LIVm)
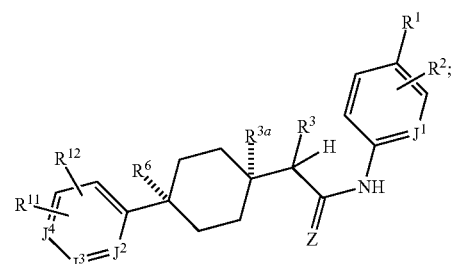
Formula (LIVn)
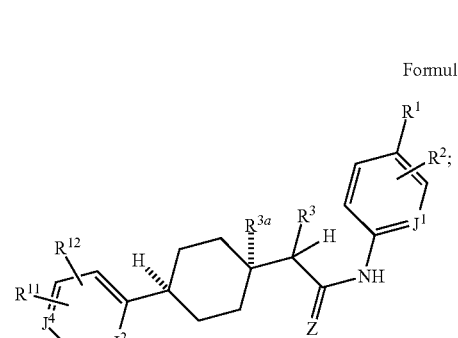
Formula (LIVo)
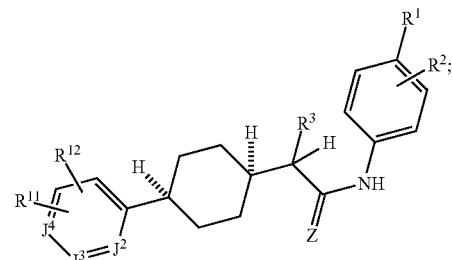
Formula (LIVp)
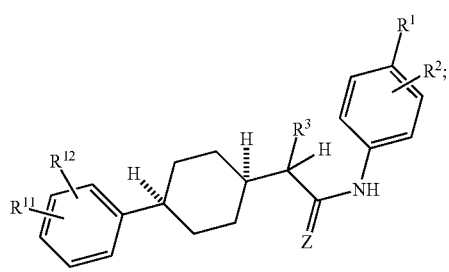
Formula (LIVq)
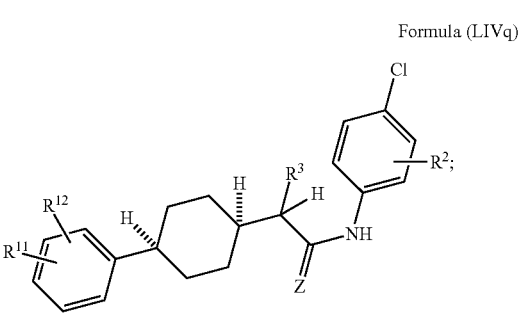
Formula (LIVr)
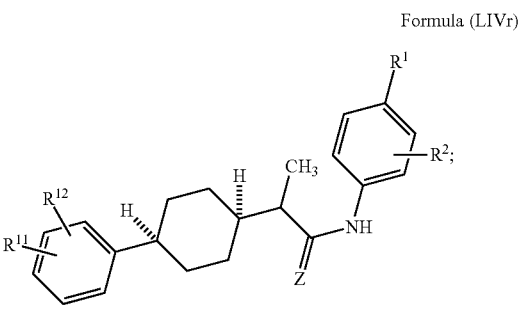
Formula (LIVs)
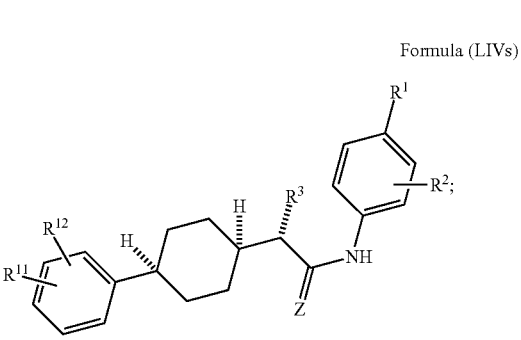
Formula (LIVt)
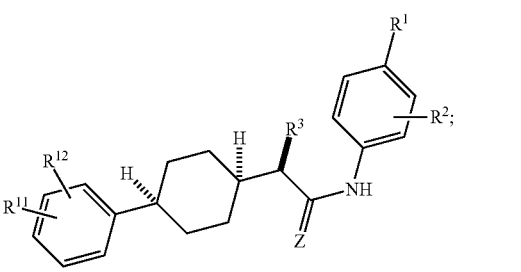

Formula (LIVu)
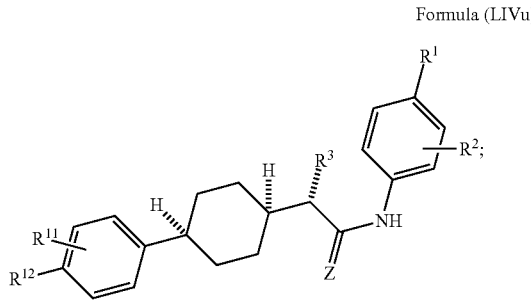

Formula (LIVv)
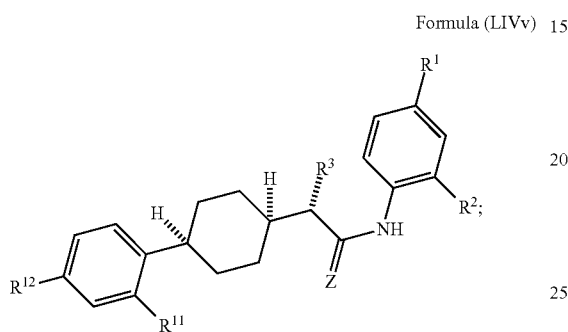

Formula (LIVw)
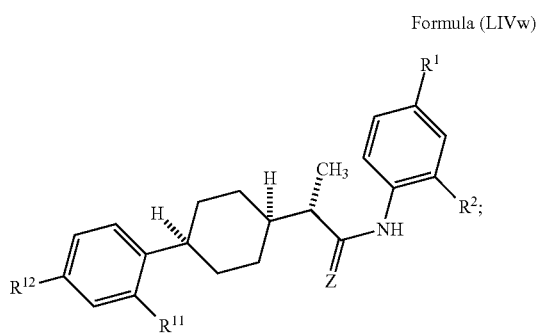

Formula (LIVx)
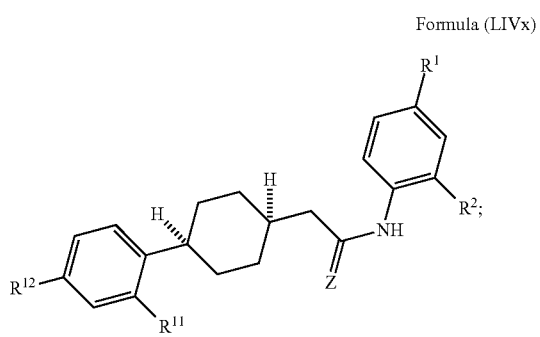

Formula (LIVy)
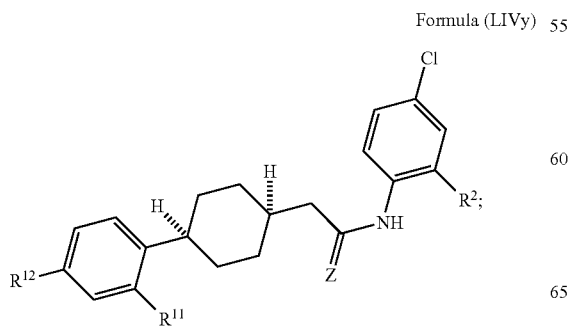

Formula (LIVz)
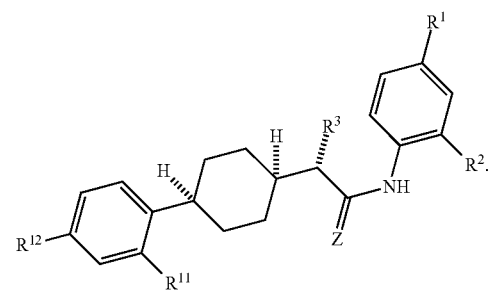
and

Formula (LIVaa)
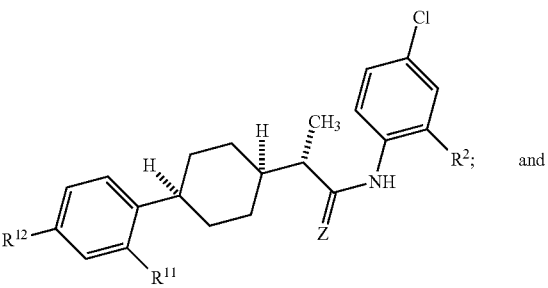

The variable definitions, embodiments, and compound structures are as described in PCT Application Publication Number WO2016073738.

In some embodiments, suitable IDO inhibitors for use in the compositions and methods disclosed herein are the IDO inhibitors described in PCT Application Publication Number WO2015188085, which is hereby incorporated by reference herein in its entirety. In some embodiments, the IDO inhibitor is a compound of Formula (LV), or a pharmaceutically acceptable salt thereof:

Formula (LV)
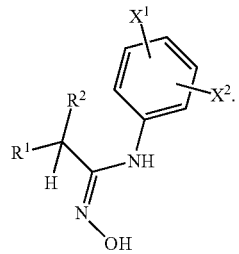

In some embodiments, the IDO inhibitor is a compound selected from one of the following formulas, or a pharmaceutically acceptable salt thereof:

Formula (LVa)
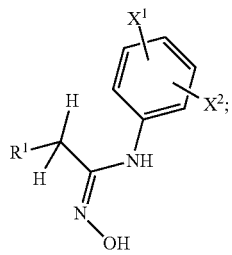

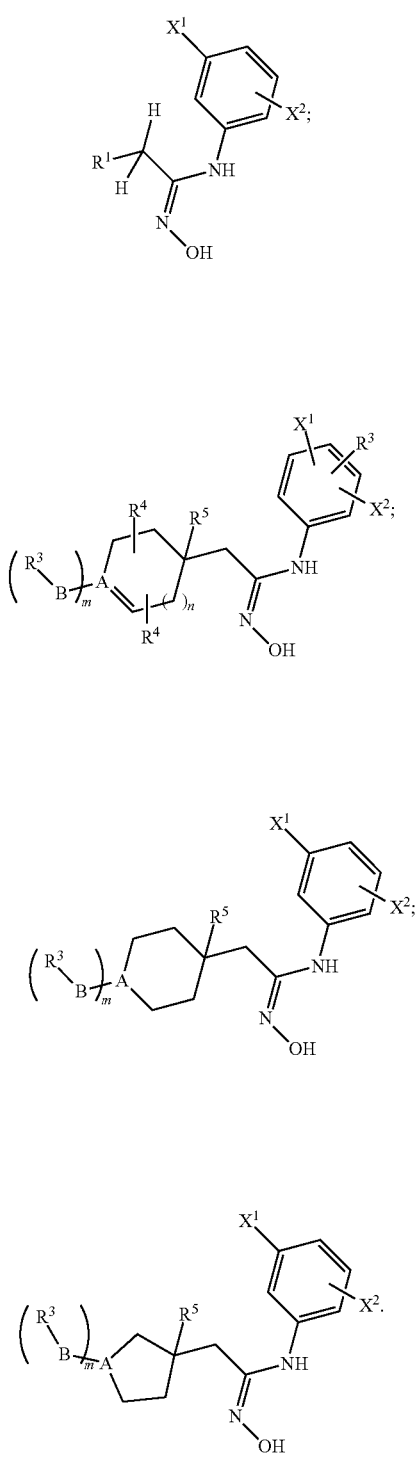

The variable definitions, embodiments, and compound structures are as described in PCT Application Publication Number WO2015188085.

In particular embodiments, the disclosure provides methods of treating cancer by administering to a human subject epacadostat and an arginase inhibitor having one of the following stuctures, or a pharmaceutically acceptable salt therof:

In some such embodiments, the epacdostat and an arginase inhibitor depicted in the schematic above are provided in a single pharmaceutical composition. In another embodiment, the epacdostat and an arginase inhibitor depicted in the schematic above are administered in separate pharmaceutical compositions.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

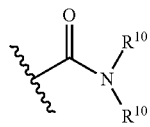

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

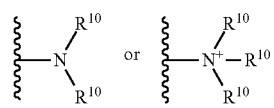

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Accordingly, the term "aryl" can encompass ($C_5$-$C_{10}$) and ($C_6$-$C_{10}$) aryl groups. Aryl groups include benzene, naphthalene, phenanthrene, phenol, aniline, and the like.

The term "carbamate" is art-recognized and refers to a group

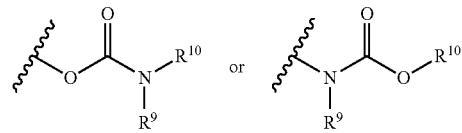

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be susbstituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "(cycloalkyl)alkyl", as used herein, refers to an alkyl group substituted with a cycloalkyl group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —$C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The term "heteroaralkyl", as used herein, refers to an alkyl group substituted with a heteroaryl group.

The term "heteroalkyl", as used herein, refers to a saturated or unsaturated chain of carbon atoms and at least one heteroatom, wherein no two heteroatoms are adjacent.

The term "heteroaryl" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Accordingly, the term "heteroaryl" can encompass ($C_2$-$C_{10}$) and ($C_2$-$C_{10}$) heteroaryl groups. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocycloalkyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocycloalkyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocycloalkyl groups include, for example, piperidine, piperazine, pyrrolidine, morpholine, lactones, lactams, and the like.

The term "(heterocycloalkyl)alkyl", as used herein, refers to an alkyl group substituted with a heterocycloalkyl group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulas

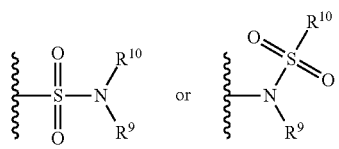

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

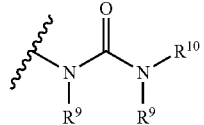

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

The term "bioavailability" refers to the fraction of an administered drug that reaches the systemic circulation, one of the principal pharmacokinetic properties of drugs. When a medication is administered intravenously, its bioavailability is 100%. When a medication is administered via other routes (such as oral), its bioavailability generally decreases due to incomplete absorption and first-pass metabolism or may vary from patient to patient. Bioavailability is a term that indicates measurement of total amount of drug that reaches the general circulation from an administered pharmaceutical composition, e.g., from an orally or intravenously administered pharmaceutical composition, in a single dose or multiple dose setting. It is often expressed in %, i.e., area under the concentration time curve "AUC" (from 0 time to infinity) or AUC (from 0 time to 48 or 72 h) of a single dose of the drug when administered, e.g., orally, in serum, blood or plasma compared to the AUC (from 0 time to infinity) or AUC (from 0 time to 48 or 72 h) of single dose of the same amount of drug when injected, i.e., AUC(orally)/AUC(injected) expressed in %. Also, "T max" denotes the time to reach the maximal plasma concentration (C max) after administration.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into therapeutically active agents, such as the compounds of Formula A or Formula B. A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present disclosure. Alternatively, amides (e.g., an amide of an amino group) may be a prodrug of the disclosure. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

One or more constituent atoms of the compounds presented herein can be replaced or substituted with isotopes of the atoms in natural or non-natural abundance. In some embodiments, the compound includes at least one hydrogen that is enriched for deuterium atoms, i.e., the compound contains deuterium atoms in excess of the natural abundance of deuterium on Earth. For example, one or more hydrogen atoms in a compound presented herein can be enriched for deuterium (e.g., one or more protium atoms of a $C_{1-6}$ alkyl group can be replaced by deuterium atoms, such as —$CD_3$ being substituted for a more common —$C(^1H)_3$ methyl group). In some embodiments, the compound is enriched for two or more deuterium atoms. In some embodiments, the compound includes 1, 2, 3, 4, 5, 6, 7, 8, 9, 10, 11, 12, 13, 14, 15, 16, 17, 18, 19, 20, 21, 22, 23, or 24 deuterium atoms. In some embodiments, all of the hydrogen atoms in a compound can be enriched for deuterium atoms instead of protium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes, such as deuterium for protium, may afford certain therapeutic advantages resulting from greater metabolic stability, for example, increased in vivo half-life or reduced dosage requirements, and hence may be preferred in some circumstances. (see, e.g., A. Kerekes et. al. *J. Med. Chem.* 2011, 54, 201-210; R. Xu et. al. *J. Label Compd. Radiopharm.* 2015, 58, 308-312).

The radionuclide that is incorporated in the instant radio-labeled compounds will depend on the specific application of that radio-labeled compound. For radio-imaging applications, $^{11}C$, $^{18}F$, $^{125}I$, $^{123}I$, $^{124}I$, $^{131}I$, $^{75}Br$, $^{76}Br$, or $^{77}Br$ can be useful.

It is understood that a "radio-labeled" or "labeled compound" is a compound that has incorporated at least one radionuclide. In some embodiments, the radionuclide is selected from $^3H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and one of ordinary skill in the art will readily recognize methods applicable for the compounds of disclosure.

Pharmaceutical Compositions

In certain embodiments, the disclosure provides a solid pharmaceutical composition comprising a compound of the disclosure, such as a compound of formula (I) (which includes compounds of formulas (I'), (I''), (I'''), (I*), (Ia), (Ib), (Ic), (Id), (Ie), (If), (Ig) and (Ih)) or a pharmaceutically acceptable salt thereof; and a pharmaceutically acceptable carrier.

In certain embodiments, the present disclosure provides a pharmaceutical preparation suitable for use in a human patient, comprising any compound of the disclosure (e.g., a compound of formula (I)), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

One embodiment of the present disclosure provides a pharmaceutical kit comprising a compound of the disclosure, such as a compound of formula (I), or a pharmaceutically acceptable salt thereof, and optionally directions on how to administer the compound.

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the disclosure and a pharmaceutically acceptable carrier. Pharmaceutically acceptable carriers are well known in the art and include, for example, non-aqueous vehicles such as glycols, glycerol, oils such as olive oil, or injectable organic esters. The excipients can be chosen, for example, to effect delayed release of an agent or to selectively target one or more cells, tissues, or organs. The pharmaceutical composition can be in dosage unit form such as tablet, capsule (including sprinkle capsule and gelatin capsule), granule, lyophile for reconstitution, powder, suppository, or the like. The composition can also be present in a transdermal delivery system, e.g., a skin patch.

A pharmaceutically acceptable carrier can contain physiologically acceptable agents that act, for example, to stabilize, increase solubility or to increase the absorption of a compound such as a compound of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a self microemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) ethyl alcohol; and (17) other non-toxic compatible substances employed in pharmaceutical formulations.

A pharmaceutical composition (preparation) can be administered to a subject by any of a number of routes of administration including, for example, orally (for example, drenches as in non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in a non-aqueous liquid, or as pastilles (using an inert base, such as gelatin and glycerin, or sucrose and acacia) and the like, each containing a predetermined amount of a compound of the present disclosure as an active ingredient. Compositions or compounds may also be administered as a bolus, electuary, or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable nonaqueous carriers that may be employed in the pharmaceutical compositions of the disclosure include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the disclosure may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the disclosure with one or more additional therapeutic agent(s) (e.g., one or more additional chemotherapeutic agent(s)) provides improved efficacy relative to each individual administration of the compound of the disclosure (e.g., compound of formula (I)) or the one or more additional therapeutic agent(s). In certain such embodiments, the conjoint administration provides an additive effect, wherein an additive effect refers to the sum of each of the effects of individual administration of the compound of the disclosure and the one or more additional therapeutic agent(s).

This disclosure includes the use of pharmaceutically acceptable salts of compounds of the disclosure in the compositions and methods of the present disclosure. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, oxalic, mandelic and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula (I). As another example, the salt may comprise less than one inorganic or organic acid molecule per molecule of base, such as two molecules of compound of Formula (I) per molecule of tartaric acid.

In further embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts.

The pharmaceutically acceptable acid addition salts can also exist as various solvates, such as with methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The disclosure now being generally described, it will be more readily understood by reference to the following examples which are included merely for purposes of illustration of certain aspects and embodiments of the present disclosure, and are not intended to limit the disclosure.

EXAMPLES

Abbreviations:
ACN=acetonitrile
Boc=tert-butyloxycarbonyl
Bn=benzyl
Cbz or Z=benzyloxycarbonyl
COD=cyclooctadiene
DCM=methylene chloride or dichloromethane
DMAP=4-(dimethylamino)pyridine
DMF=dimethylformamide
dppe=ethylenebis(diphenylphosphine)
EDC or EDCI=N-(3-dimethylaminopropyl)-N'-ethylcarbodiimide
EtOAc=ethyl acetate
iso-BuB(OH)$_2$=isobutylboronic acid
LiHMDS—lithium bis(trimethylsilyl)amide
OSu=N-hydroxysuccinimide
TBAF=tetrabutylammonium fluoride hydrate
TFA=trifluoroacetic acid
THF=tetrahydrofuran
TMS=trimethylsilane
Z-Ala-OSu=Benzyloxycarbonyl-L-alanine hydroxysuccinimde ester
Z-OSu=N-(Benzyloxycarbonyloxy)succinimide
Pin=pinacol

Example 1: General Procedure for the Alcoholate Complex Formation

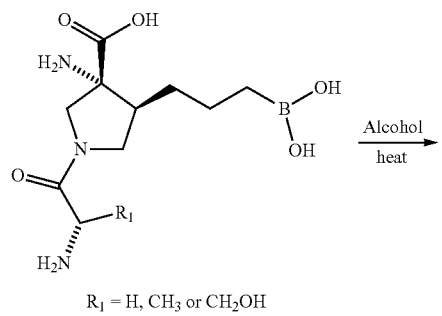

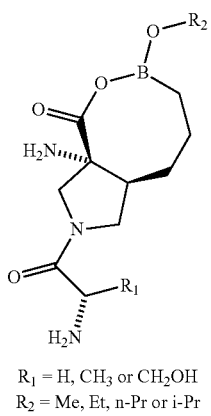

The boronic acid amino acid (200 mg) was suspended in anhydrous alcohol (20 mL). The suspension was stirred at 70° C. for 14 hours, resulting in complete dissolution of the compound. The reflux condenser was changed to a small distillation head and the reaction was distilled (at atmospheric pressure (with an attached Drierite drying tube to exclude moisture) until the hot solution had started to become cloudy (approximately half of the alcohol had been collected during the distillation). Anhydrous alcohol (10 mL) was added and then the reaction was heated to 80° C. and stirred at 80° C. for a further 4 hrs. The distillation process was repeated until the solution became cloudy once again (~10 mL distillate collected). Anhydrous alcohol (10 mL) was added again and then the reaction was heated to 80° C. and stirred at 80° C. for a further 2 hours. The distillation process was repeated until the solution just started to become cloudy (~15 mL distillate collected). The remaining solution was allowed to cool to RT and then filtered and quickly suction dried, and then further dried under high vacuum (38 mTor) at room temperature for at least 2 hrs to give the product as an off-white to pale yellow powder.

Example 2: Exemplary Synthetic Method to Arginase Inhibitor

Synthesis of (6aS,9aR)-8-(L-alanyl)-9a-amino-3-ethoxyoctahydro-[1,2]oxaborocino[6,7-c]pyrrol-1(3H)-one (10e)

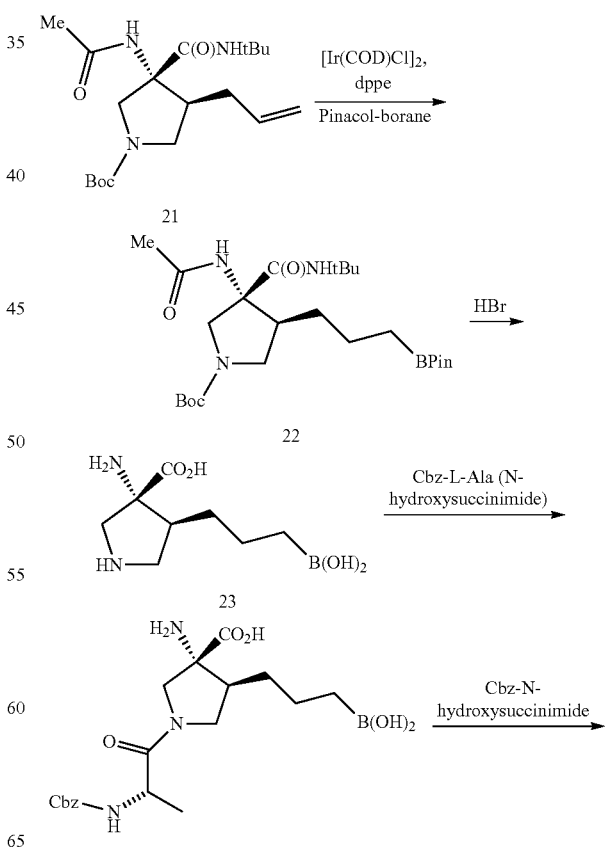

-continued

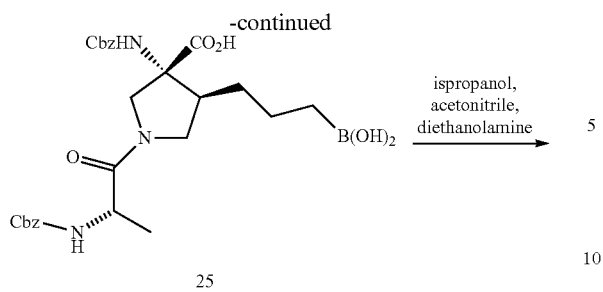

25

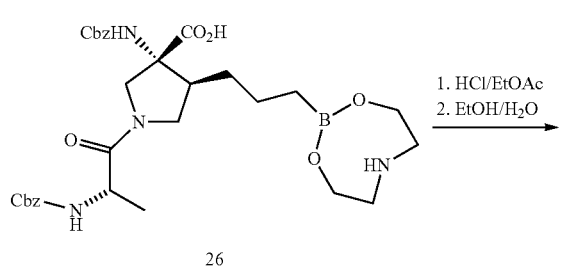

26

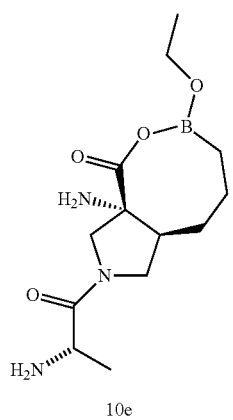

10e

Starting material compound 21 (racemic) was prepared as described WO2012/058065 at page 48-50, which is incorporated herein by reference. The resolution was done by chiral chromatography. Racemic compound 21 was resolved on a chiral stationary phase CHIRALPAK® 1B column (Daicel Chiral Technologies) using heptane-ethanol as the eluent to yield the resolved enantiomer of compound 21.

Iridium-Catalyzed Hydroboration to Give 22

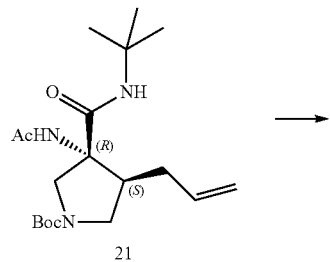

21

-continued

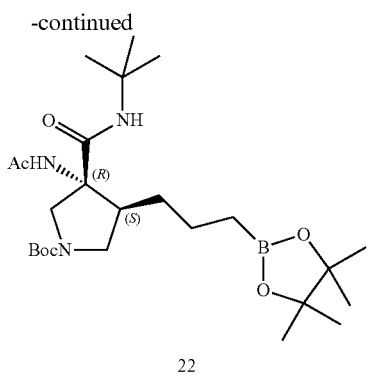

22

A 10 L reaction flask with dichloromethane (5 L) was evacuated to approximately 250 mBar, and the pressure was released with nitrogen. The procedure was repeated twice, and the reaction was performed under nitrogen atmosphere. Bis (1,5-cyclooctadiene)diiridium (I) dichloride (26.00 g, 38.7 mmol, 0.03 eq.) and ethylenebis(diphenylphosphine) (30.85 g, 77.4 mmol, 0.06 eq.) were added, and the mixture was stirred at 13-15° C. until formation of a clear solution was observed. Compound 21 (resolved, 466.3 g, 1.269 mol) was added, and the mixture was stirred at 15-17° C. for a period of 30 minutes. The resulting dark red solution was cooled to 0° C., and 4,4,5,5-tetramethyl-1,3,2-dioxaborolane (224.0 g, 1.750 mol, 1.38 eq.) was added at −2 to +2° C. over a period of one hour. The reaction mixture was stirred at −2 to +2° C. for a period of 2 hours, and HPLC indicated 90.7% conversion. After stirring an additional 14 h at 18-22° C., HPLC indicated 98.9% conversion.

Acetonitrile (2.2 L) was added to the reaction mixture. The mixture was heated for distillation at 30-35° C. under reduced pressure (470 mBar), and 2.7 L were distilled off. Acetonitrile (2.2 L) was added to the residue. The mixture was heated for distillation at 35-38° C. under reduced pressure (350-250 mBar), and 2.2 L were distilled off. Acetonitrile (2.2 L) was added to the residue. The mixture was heated for distillation at 55-40° C. under reduced pressure (240-155 mBar), and 3.7 L were distilled off.

The residual suspension (~1300 mL) was stirred at 20-23° C. overnight and the precipitate was isolated by filtration. The filter cake was washed with cold (0-10° C.) acetonitrile (1.5 L) and dried to a constant weight at 40° C. in an air-vented drying oven. Obtained yield of compound 22: 466.5 g (74%).

Preparation of Compound 26

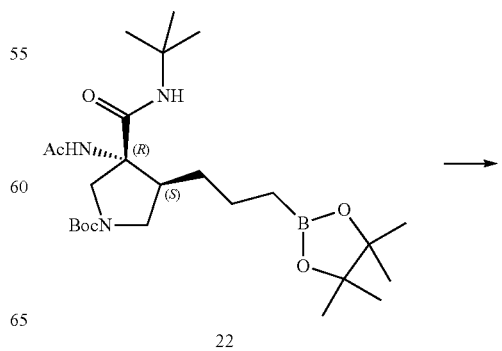

22

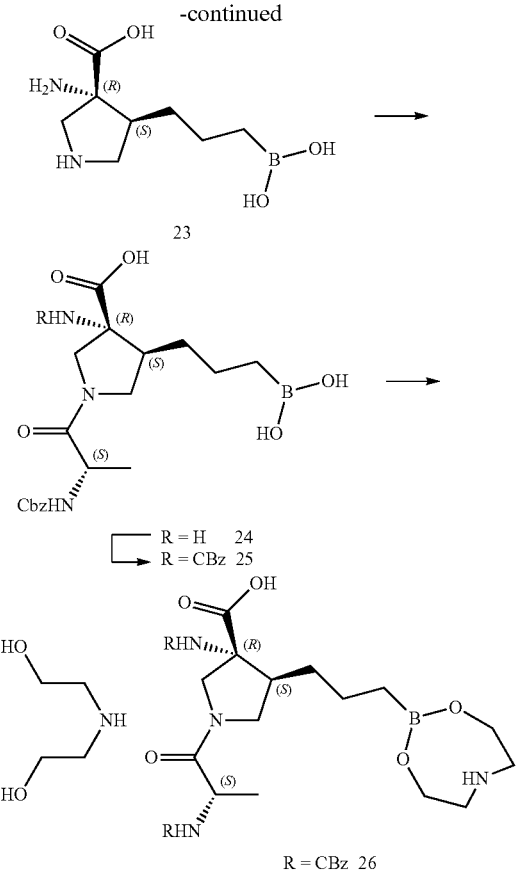

48% HBr (aq., 500 mL) and compound 22 (250 g, 505 mmol) were added to a 2 L, 3-necked round bottom flask. The mixture was heated for distillation, and the distillation was continued until an internal temperature of 120° C. was reached. The mixture was stirred at 120° C. for an additional 2 h. The mixture was allowed to cool to room temperature. Water was added (0.5 L), and the reaction mixture was extracted with toluene (1 L). The atmosphere was exchanged for nitrogen and the aqueous mixture was cooled to 0° C., and the aqueous solution of compound 23 was left overnight. The pH of the mixture was adjusted to 9.7 with NaOH (27.65%, 460 mL), followed by the addition of acetonitrile (750 mL). Z-Ala-OSu (323 g, 1009 mmol, 2 eq.) was added, and pH was continuously adjusted to 9.5-10.0 with NaOH (27.65%, 175 mL). After 1.5 h the conversion was >98% (TLC). The pH was adjusted to 3.3 with 48% HBr (aq., 207 mL), and the reaction mixture was allowed to warm to room temperature. The mixture was extracted with toluene (1.14 L) and two times with ethyl acetate (2×1.14 L). The two ethyl acetate phases were back-extracted twice with water (2×225 mL). The combined aqueous phases, containing compound 24 were kept under nitrogen at 0° C. overnight.

The pH of the mixture was adjusted to 10.4 with NaOH (27.65%, 207 mL), and the temperature was allowed to increase to 10-20° C. Acetonitrile was added (750 mL), followed by Z-OSu (176 g, 707 mmol, 1.4 eq.) and the pH of the mixture was continuously adjusted to 10.0-10.5 with NaOH (27.65%, 112 mL). The reaction was allowed to continue for 3 h until a conversion of >95% was observed (HPLC, comparison with standard). The pH was adjusted to 3.2 with 48% HBr (aq., 300 mL). Ethyl acetate (1.14 L) was added, and the mixture was stirred vigorously. The phases were separated and the organic phases combined giving compound 25 which was kept in the freezer overnight.

The ethyl acetate solution of compound 25 was evaporated under reduced pressure at a water bath temperature of 50° C. until dryness. Acetonitrile (200 mL) was added, and the evaporation was continued until dryness. The residue was dissolved in acetonitrile (3.63 L) at 40° C. and isopropanol (225 mL) was added. Diethanolamine (95.9 g, 912 mmol) was dissolved in isopropanol (150 mL) and acetonitrile (150 mL). The diethanolamine solution was added to the acetonitrile/isopropanol solution of compound 25 at 40° C. over 10 minutes. The solution was seeded with compound 26 and cooled to room temperature. The precipitation was very slow and had to be left overnight, where a thick suspension was obtained. The suspension was filtered slowly, and the filter cake was washed with 2 L of 10% isopropanol/acetonitrile. Part of the filter cake was dried, giving a yield of 83% (276.2 g).

The main part (271.6 g) of the material was re-precipitated by suspending it in isopropanol (400 mL) and acetonitrile (900 mL). The solid was dissolved at reflux temperature. Acetonitrile (2.7 L) was added, and the solution was allowed to cool to room temperature. At 45° C. precipitation was observed. After 5 h the thick suspension was filtered and the filter cake was washed with 1.5 L of 10% isopropanol/acetonitrile. The solid was dried overnight in vacuum at 25° C., giving 239.2 g of compound 26 (88% recovery, 72% overall yield).

Preparation of Compound 10e

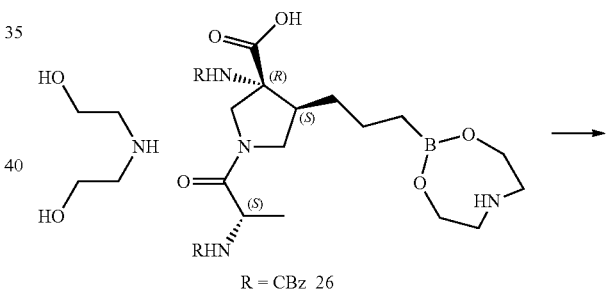

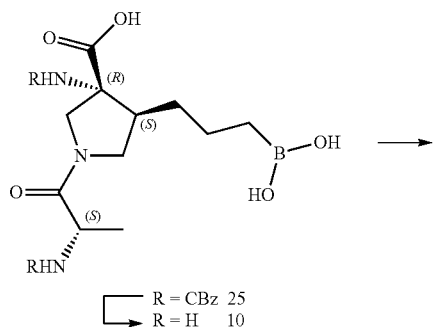

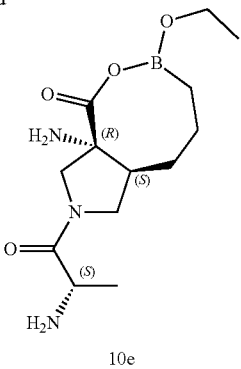

10e

To a 5 L, three-necked round-bottomed flask was added water (2.4 L) and 36% HCl (aq, 75 g). Ethyl acetate (2.45 L) was added followed by compound 26 (250 g, 343 mmol). The mixture was stirred until the solid had dissolved. The phases were separated, and the aqueous phase was extracted with ethyl acetate (1.22 L). The combined organic phases were dried over magnesium sulphate (190 g). The suspension was filtered, and the filter cake was washed with ethyl acetate (560 mL). The filtrate and wash were evaporated under reduced pressure at a water bath temperature of 50° C. to give crude 25 as a white foam. Ethanol (2.4 L) and water (100 mL) were added, and the mixture was stirred until a solution was obtained. The system was evacuated to <180 mbar and the vacuum was released with nitrogen three times. 10% Pd/C was added (wet, 57.7% water, 35.9 g). The system was evacuated to <180 mbar and the vacuum released with nitrogen one time and hydrogen three times. The hydrogenation was continued overnight at room temperature, then the atmosphere was exchanged for nitrogen and another portion of 10% Pd/C was added (wet, 57.7% water, 4.5 g). The atmosphere was exchanged for hydrogen, and the hydrogenation was continued for another night. The slurry was filtered over celite (83 g), and the filter cake was washed with a mixture of ethanol (400 mL) and water (16.7 mL) to give a crude solution of 10. The filtrate was evaporated under reduced pressure in portions at a water bath temperature of 50° C. to a volume of 350-400 mL. Ethanol (600 mL) was added, and the solution was seeded with compound 10e. The thin suspension was concentrated to the same volume under reduced pressure and at a water bath temperature of 50° C. The suspension was kept at −15° C. for three days. The suspension was allowed to warm to around 0° C. and then filtered (GF-A). The filter cake was washed with ethanol (3×100 mL). The solid was dried at 50° C. under vacuum overnight to give 82.8 g of compound 10e. This material could be further purified as described below.

Compound 10e (77.5 g) was suspended in ethanol (1.1 L) and heated to 60-62° C. for 6 h and 15 min. The suspension was cooled to 2° C., and stirred overnight. The suspension was filtered and the filter cake was washed with ethanol (400 mL). The solid was dried at 50° C. under vacuum overnight to give 71.5 g of compound 10e as a white solid.

An analytical sample or 10e was prepared as follows: 2 g of 10e was suspended in sufficient anhydrous ethanol (~70 mL) to fully dissolve the material at 80° C. This solution was heated at 80° C. for 2 hrs under an atmosphere of dry nitrogen. The reflux condenser was changed to a small still head and the reaction was distilled (at atmospheric pressure, with an attached drying tube to exclude moisture) until the hot solution had started to become cloudy (approximately 40 mL of ethanol had been collected during the distillation). This procedure was repeated twice more, and the remaining solution was allowed to cool to RT and then filtered and quickly suction dried, and then further dried under high vacuum (40 mTor) at RT for 2 hrs to give an analytical sample of 10e as a white powder.

Compound 10e. 400 MHz, d6-DMSO: (3:2 rotamer population) d 7.01-6.80 (2H, br m, exch), 3.81 (1H, d, J=12.8 Hz), 3.68 (0.6H, dd, J=9.8, 7.5 Hz), 3.62 (0.4H, dd, J=11.3, 7.8 Hz), 3.53 (0.4H, d, J=10.4 Hz), 3.48-3.35 (3H, m), 3.20 (0.6 H, d, J=12.5 Hz), 3.13 (0.6H, dd, J=11.7, 9.7 Hz), 2.81 (0.4H, t, J=11.6 Hz), 2.42 (0.6H, m) and 2.30 (0.4H, m), 1.83-1.70 (2H, m), 1.62 (2H, br s, exch), 1.44-1.37 (1H, m), 1.09-1.04 (6H, m, CH3CH2 and CH3CHN), 0.98 (1H, dd, J=15, 12.4 Hz), 0.65 (1H, dd, J=14.7, 5.6 Hz) and 0.42 (1H, m). $^{11}$B-NMR (400 MHz, DMSO) δ: 7.85 ppm. FTIR (powder diffraction) (cm$^{-1}$): 2905 (w), 1722 (s), 1646 (s), 1623 (s), 1271 (s), 1119 (s), 1067 (m), 658 (m) and 562 (m).

800 mg of the analytical sample of 10e was dissolved in the minimum amount of ethanol (~30 mL) at room temperature. This solution was allowed to sit, at room temperature and pressure, in a desiccator, fitted with a DRIERITE® drying tube to exclude moisture, to allow the ethanol to slowly evaporate, causing fine crystals to slowly form over the course of 10 days. These crystals were filtered under suction, washed quickly with cold (5° C.) ethanol and then dried under high vacuum (40 mTor) at RT for 14 hrs to give the product (386 mg) as white crystals suitable for crystallography.

X-Ray Structure Determination

Low-temperature diffraction data (ω-scans) were collected on a Rigaku MicroMax-007HF diffractometer coupled to a Saturn994+ CCD detector with Cu Kα (λ=1.54178 Å) for the structure of 10e. The diffraction images were processed and scaled using the Rigaku CrystalClear software (CrystalClear and CrystalStructure; Rigaku/MSC: The Woodlands, Tex., 2005). The structure was solved with SHELXT and was refined against F$^2$ on all data by full-matrix least squares with SHELXL (Sheldrick, G. M. Acta Cryst. 2008, A64, 112-122). All non-hydrogen atoms were refined anisotropically. Hydrogen atoms were included in the model at geometrically calculated positions and refined using a riding model. The isotropic displacement parameters of all hydrogen atoms were fixed to 1.2 times the U value of the atoms to which they are linked (1.5 times for methyl groups). All hydrogen atoms associated with nitrogen atoms were found in the difference map. The N—H distances were restrained to 0.92(2), as suggested by the difference map. The atomic displacement parameters were allowed to freely refine. The hydrogen atom associated with the ethanol was geometrically placed and restrained. All hydrogen atoms involved in hydrogen bonding were identified and their associated donor/acceptor metrics were refined.

Figure 1:
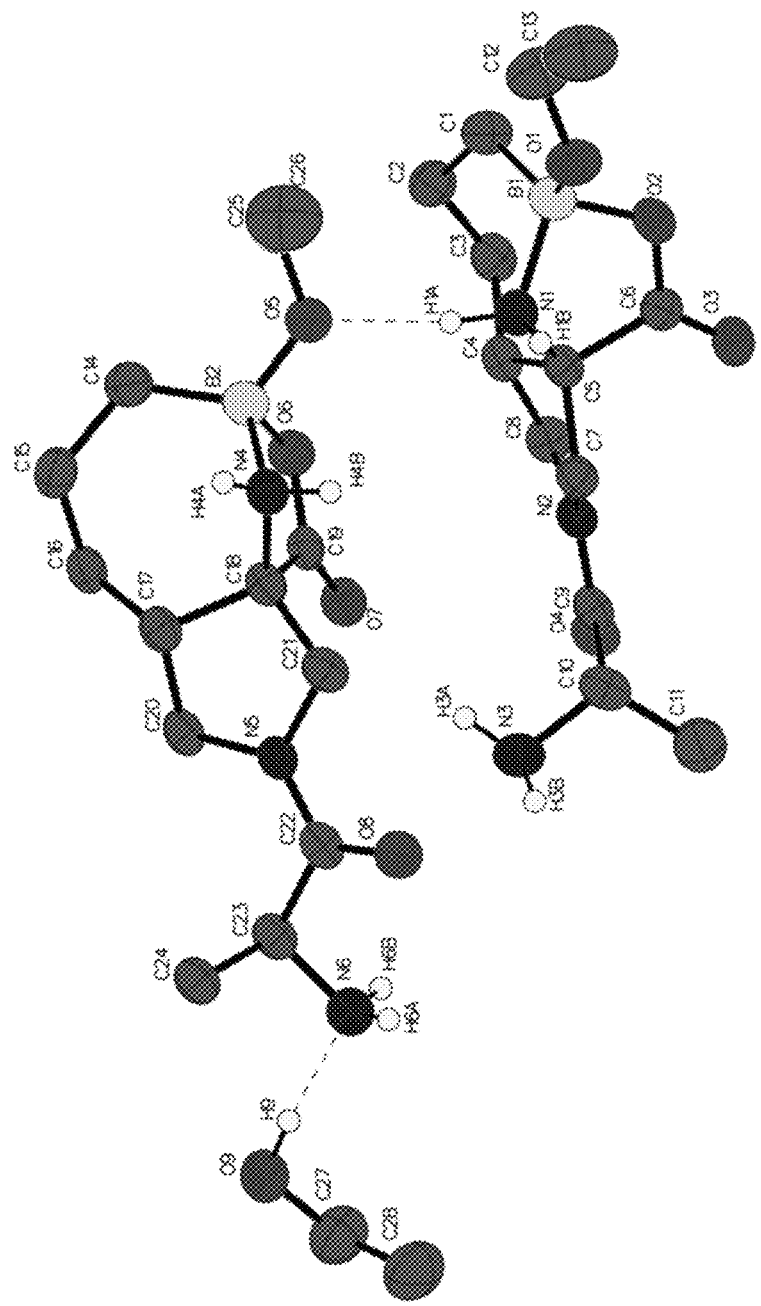
FIG. 1 shows the structure of compound 10e obtained by X-ray diffraction with 50% thermal ellipsoid probability levels. Most hydrogen atoms have been omitted for clarity.

The structure of 10e obtained by X-ray diffraction is shown in FIG. 1 at 50% thermal ellipsoid probability levels. This structure is consistent with the line drawings for 10e shown in the text. Certain crystal data and structure refinement for 10e are provided in Table 2.

TABLE 2

| Crystal data and structure refinement for 10e. | |
|---|---|
| Empirical formula | C14 H26 B N3 O4.50 |
| Formula weight | 319.19 |
| Temperature | 93(2) K |
| Wavelength | 1.54178 Å |
| Crystal system | Orthorhombic |
| Space group | $P2_12_12_1$ |
| Unit cell dimensions | a = 9.7668(7) Å     $\alpha = 90°$. |
| | b = 11.6068(8) Å    $\beta = 90°$. |
| | c = 29.707(2) Å     $\gamma = 90°$. |
| Volume | 3367.6(4) Å$^3$ |
| Z | 8 |
| Density (calculated) | 1.259 Mg/m$^3$ |
| Absorption coefficient | 0.761 mm$^{-1}$ |
| F(000) | 1376 |
| Crystal size | 0.200 × 0.200 × 0.010 mm$^3$ |
| Theta range for data collection | 4.089 to 66.565°. |
| Index ranges | $-11 \le h \le 11, -13 \le k \le 13, -35 \le l \le 35$ |
| Reflections collected | 111128 |
| Independent reflections | 5944 [R(int) = 0.1161] |
| Completeness to theta = 66.565° | 99.9% |
| Absorption correction | Semi-empirical from equivalents |
| Max. and min. transmission | 1.000 and 0.727 |
| Refinement method | Full-matrix least-squares on F$^2$ |
| Data/restraints/parameters | 5944/8/444 |
| Goodness-of-fit on F$^2$ | 1.171 |
| Final R indices [I > 2sigma(I)] | R1 = 0.0642, wR2 = 0.1681 |
| R indices (all data) | R1 = 0.0739, wR2 = 0.1741 |
| Absolute structure parameter | −0.10(8) |
| Largest diff. peak and hole | 0.330 and −0.227 e.Å$^{-3}$ |

The conversion of compound 10 to compound 10e represents an equilibrium and the composition of the mixture depends on the solvent composition. The formation of 10e occurs upon treatment of compound 10 with anhydrous ethanol. This transformation presumably proceeds though intermediates B and/or C as shown in Scheme 1. Compound 10e is the predominant species formed through treatment of 10 with absolute ethanol and removal of water through distillation or by re-slurrying the material with hot absolute ethanol. Samples of 10 that have undergone less extensive processing (in ethanol) to remove water contain mixtures of 10e and intermediates A, B, or C (Scheme 1).

Scheme 1. Interconversion of compounds 10 and 10e.

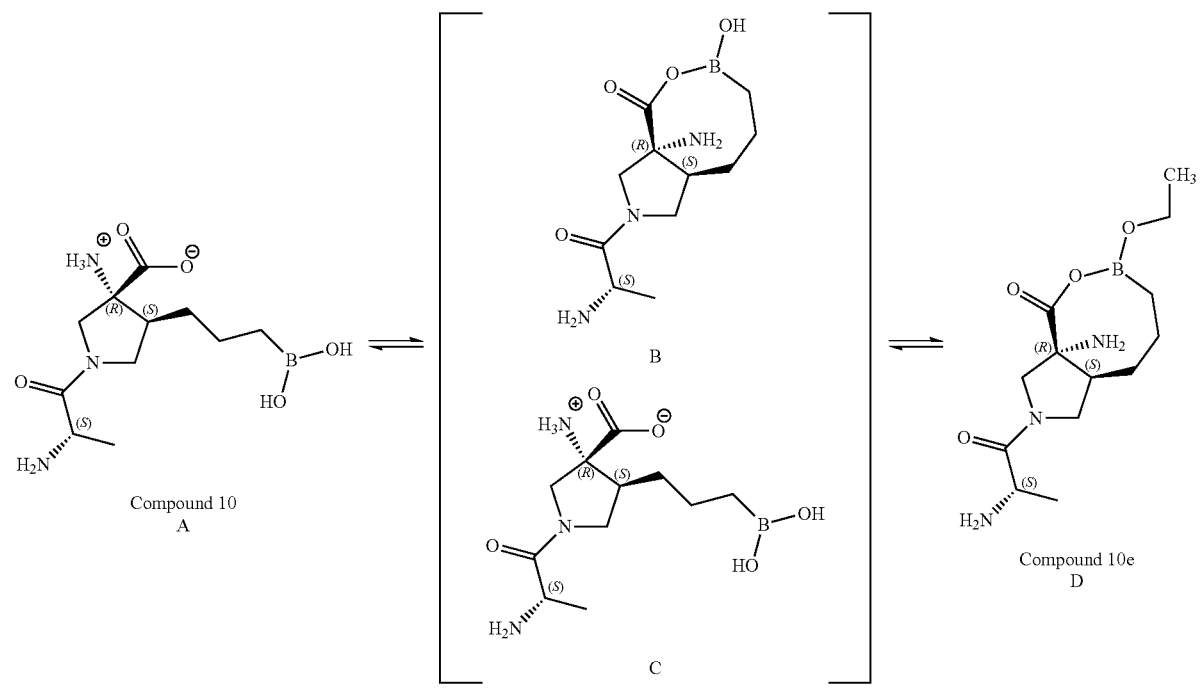

The isolated ethanolate (compound 10e) rapidly hydrolyzes under physiological conditions or any other aqueous conditions to the open free boronic acid form, compound 10, which may exist in an equilibrium of open form A and closed form B. It should be understood in these depicted structures, the NH₂ moieties each exist in an equilibrium of protonated (salt) and unprotonated (free base) forms, and the depictions above are not intended to represent a fixed form for either of these moieties. The presence of other acids and/or bases in a solution will affect these equilibria, as will be understood by those of skill in the art.

The rapid conversion of compound 10e to compound 10 in water was confirmed by the similarity of a spectrum of 10e in D₂O to a spectrum of 10 in D₂O. When a sample of compound 10e was dissolved in D₂O and the spectra immediately recorded (elapsed time<5 minutes), the spectra observed is identical to a spectra of compound 10 (the free boronic acid) plus ethanol (1:1 ratio). The spectrum of 10e in D₂O was the same at 5 minutes and one hour after sample preparation, indicating the transformation was rapid and complete after a few minutes.

Figure 2:
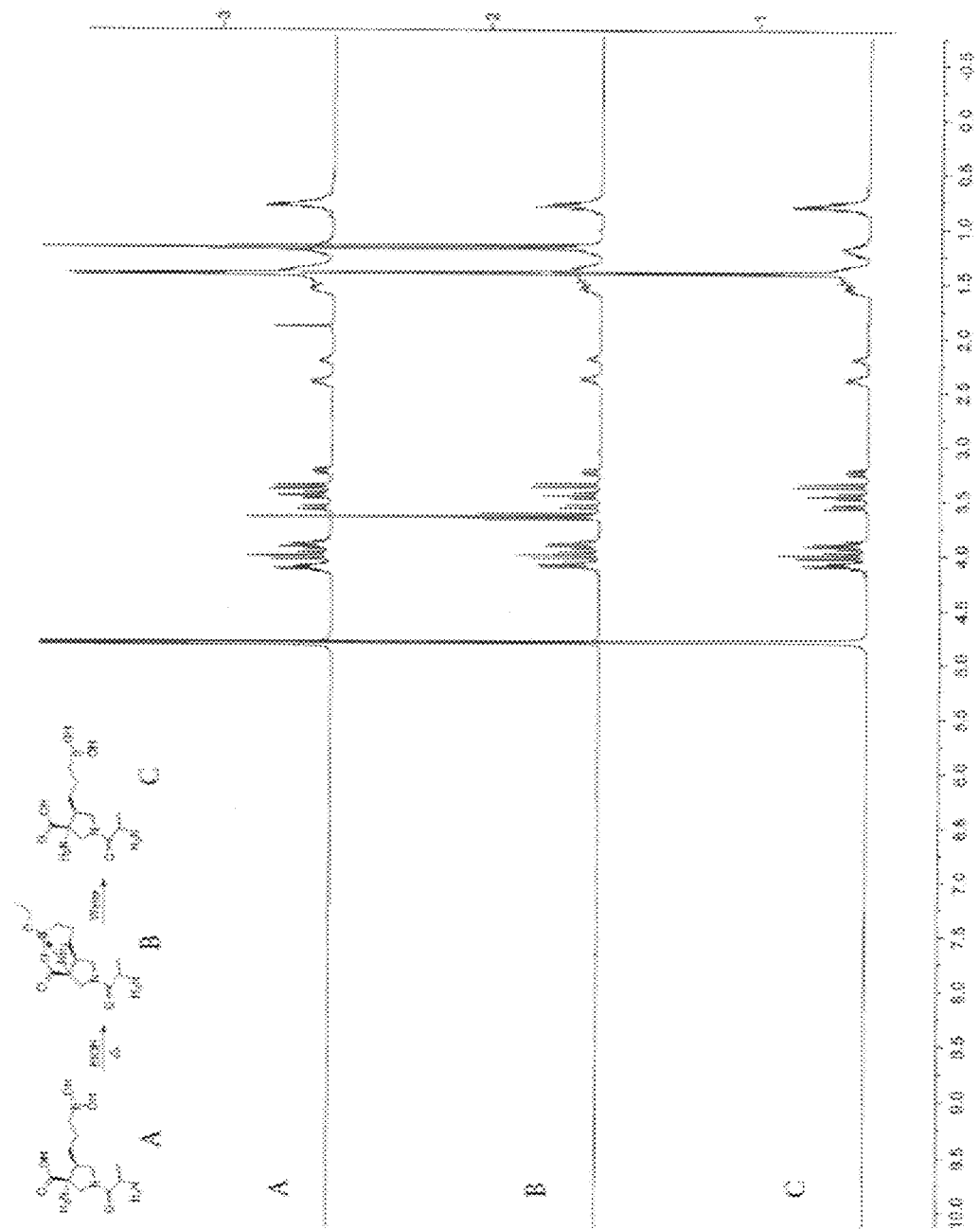
FIG. 2 shows NMR spectra (in $D_2O$) showing the conversion of compound 10 (referred to as compound A in the figure) to compound 10e (referred to as compound B in the figure) and back to compound 10 (referred to as compound C in the figure).[

FIG. 2 demonstrates the conversion of 10e to 10 in D₂O. The NMR spectra (D₂O) labeled A is compound 10 (free base) prepared from 11 as described in Example 2. The NMR spectra (D₂O) labeled B is an analytical sample of compound 10e prepared as described above. The NMR spectra (D₂O) labeled C is the sample from spectra B that has been lyophilized and redissolved in D₂O. The spectra in FIG. 2 demonstrate that the 10e undergoes hydrolysis in water and the spectra of 10e in D₂O is identical with 10 except for the presence of the ethanol which is released upon hydrolysis.

Upon dissolution in 1:1 water/acetonitrile and immediate injection into an HPLC system, only a single peak is observed. The mass of this peak is consistent with compound 10. No mass is seen for intact compound 10e.

Compound 10 is hygroscopic, with a consistent uptake of water as humidity is increased. The observed moisture uptake is over 70% at 90% relative humidity (RH). The sorption and desorption isotherms show minimal hysteresis for compound 10. Compound 10e is not notably hygroscopic in conditions below 60% RH. The sorption isotherm suggests that compound 10e does absorb water up to 40 wt percent between 60 and 90% RH. The isotherm also indicates significant hysteresis. This hysteresis is consistent with the rapid hydrolysis of the ethanolate into the corresponding boronic acid form that does have associated water in the solid state when isolated from water-containing solutions.

Example 3: Alternative Synthesis of an Exemplary Arginase Inhibitor (3R, 4S)-3-amino-1-((S)-2-aminopropanoyl)-4-(3-boronopropyl)-yl)pyrrolidine-3-carboxylate

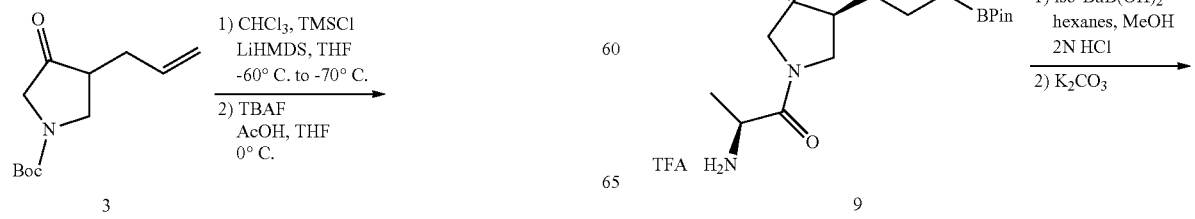

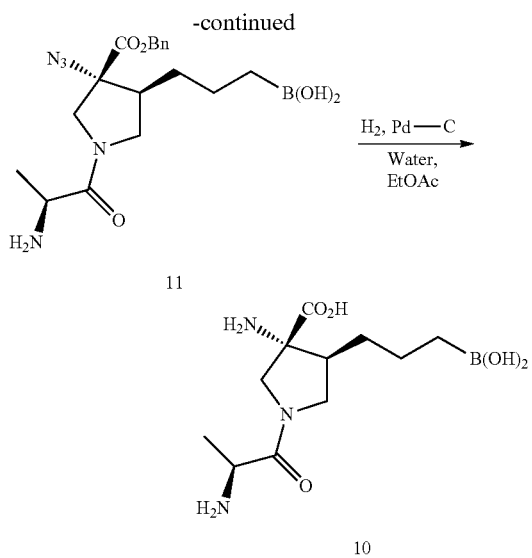

trans-4-Allyl-3-azido-1-(tert-butoxycarbonyl)pyrrolidine-3-carboxylic acid (4, Racemic)

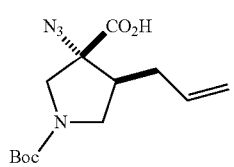

A solution of chloroform (26.86 mL, 333 mmol) and TMS-Cl (32.86 mL, 257.1 mmol) in anhydrous THF (300 mL) was cooled to −78° C. After stirring for 10 min, LiHMDS (1M in THF, 249 mL, 249 mmol) was added at a rate such that the temperature remained below −60° C. (approximately 30 min). After stirring an additional 30 min at −60 to −70° C. (reaction mixture becomes cloudy) the solution was warmed to −20° C. (reaction mixture becomes clear) and treated with tert-butyl-3-allyl-4-oxopyrrolidine-1-carboxylate (3, 30 g, 133.2 mmol) in DMF (90 mL) and tetrabutylammonium acetate (3.69 g, 12.24 mmol) in DMF (90 mL) at a rate such that the internal reaction temperature remained below −20° C. (reaction becomes cloudy). After the addition was complete, the reaction mixture was warmed to room temperature with stirring until the ketone starting material was consumed (by TLC), then poured into saturated aqueous NH$_4$Cl and extracted with EtOAc (3×100 mL). The combined organic layers were washed successively with saturated aqueous NH$_4$Cl and saturated aqueous NaCl (2×80 mL), dried over MgSO$_4$, filtered and concentrated.

While under nitrogen, the crude TMS protected intermediate was dissolved in dry THF (300 mL), cooled to 0° C. and carefully treated with acetic acid (7.5 mL, 130.9 mmol) and TBAF (1 M in THF, 133.2 mL, 133.2 mmol) dropwise. After the addition was complete, the reaction was stirred an additional 10 min at 0° C. then poured into saturated aqueous NaHCO$_3$ and extracted with EtOAc (3×100 mL). The combined organic layers were washed with saturated aqueous NaCl, dried over MgSO$_4$, filtered and concentrated to afford the crude alcohol intermediate.

The crude alcohol was dissolved in dioxane (200 mL), cooled to 0° C., and treated with a pre-cooled (0° C.) solution of sodium azide (14.04 g, 399.5 mmol) and NaOH (15.98 g, 399.5 mmol) in water (200 mL) dropwise. The resulting reaction mixture was allowed to warm to room temperature with stirring overnight then quenched with of saturated aqueous NH$_4$Cl and was extracted with EtOAc (500 mL). The aqueous layer was separated and extracted with EtOAc (2×300 mL). The combined organic layers were washed with water and saturated aqueous NaCl, dried over MgSO$_4$, filtered and concentrated to give crude trans-4-allyl-3-azido-1-(tert-butoxycarbonyl)pyrrolidine-3-carboxylic acid (4, crude 45 g) which was used without further purification. $^1$H-NMR (CDCl$_3$, 400 MHz): δ$_H$: 5.80 (1H, m), 5.06 (2H, m), 4.05 (1H, dd, J=9.9, 4.9 Hz), 3.59 (2H, m), 3.22 (1H, dd, J=11.6, 4.4 Hz), 3.08 (1H, dd, J=11.0, 5.2 Hz), 2.24-2.04 (2H, m), 1.65 (1H, br s, OH) and 1.45 (9H, s).

trans-3-Benzyl-1-(tert-butyl)-4-allyl-3-azidopyrrolidine-1,3-dicarboxylate

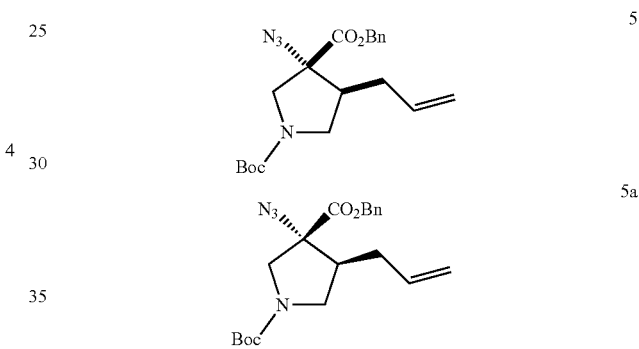

A solution of crude trans-4-allyl-3-azido-1-(tert-butoxycarbonyl)pyrrolidine-3-carboxylic acid (4, 39.5 g, 133 mmol—calculated quantity assuming 100% yield from previous steps) and K$_2$CO$_3$ (92.04 g, 666 mmol) in acetonitrile (317 mL) was cooled to 0° C. and treated with benzyl bromide (17.52 mL, 146.5 mmol). After stirring overnight at room temperature the solution was concentrated, dissolved in EtOAc (600 mL), washed with saturated aqueous NaCl, dried over MgSO$_4$, filtered and concentrated. Purification via silica gel chromatography (10 to 30% EtOAc in hexane) gave trans-3-benzyl-1-(tert-butyl)-4-allyl-3-azidopyrrolidine-1,3-dicarboxylate as yellow liquid (5, 40 g, 78% yield).

The product was separated into its enantiomers using a Chiral Technologies Chiralpak ADH column with isopropyl alcohol and hexanes (2:98) as an eluent. Analysis of the separated enantiomers using an analytical Chiralpak ADH column (4.6×250 mm) with the same eluent and a flow rate of 1.0 mL/min and UV detection (210 nm) gave the desired enantiomer (3-benzyl-1-(tert-butyl) (3R,4S)-4-allyl-3-azidopyrrolidine-1,3-dicarboxylate, 5a) with a retention time of 13.5 min and the undesired enantiomer (3-benzyl-1-(tert-butyl) (3S,4R)-4-allyl-3-azidopyrrolidine-1,3-dicarboxylate, 5b) at 10.3 min, each with an enantiomeric excess of approximately 98%. $^1$H-NMR (CDCl$_3$, 400 MHz): δ$_H$: 7.37 (5H, s), 5.62 (1H, m), 5.25 (2H, m), 5.00 (2H, m), 3.88 (1H, dd, J=37.2, 12.0 Hz), 3.58 (1H, ddd, J=37.2, 11.0, 7.0 Hz), 3.42 (1H, dd, J=21.4, 12.0 Hz), 3.28 (1H, ddd, J=28.3, 11.0, 5.4 Hz), 2.41 (1H, m), 2.11 (1H, m), 1.80 (1H, m) and 1.44 (9H, s).

(3R,4S)-3-Benzyl 1-tert-butyl 3-azido-4-(3-(4,4,5,5-tetramethyl-1,3,2-dioxaborolan-2-yl)propyl)pyrrolidine-1,3-dicarboxylate (6)

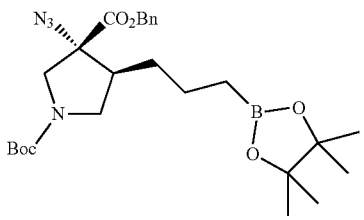

A stirred solution of 3-benzyl-1-(tert-butyl) (3R,4S)-4-allyl-3-azidopyrrolidine-1,3-dicarboxylate (5a, 16.4 g, 42.4 mmol) in anhydrous methylene chloride (130 mL), under an atmosphere of nitrogen, was treated with bis(1,5-cyclooctadiene)diiridium(I) dichloride (0.75 g, 1.12 mmol) and 1,2-bis(diphenylphosphino)ethane (0.894 g, 2.24 mmol) and the reaction was stirred for 30 minutes at room temperature and then cooled to −25° C. 4,4,5,5-tetramethyl[1,3,2]dioxaborolane (9.83 mL, 67.75 mmol) was added dropwise and then the reaction was allowed to slowly warm to room temperature and stirred for 20 hrs. Water (60 mL) was added and the reaction was stirred for 10 minutes, and then the methylene chloride was removed under reduced pressure. The remaining aqueous phase was extracted with ethyl acetate (3×100 mL). The combined organic phase was washed with brine, dried over anhydrous magnesium sulfate, filtered and concentrated in vacuo. The residual solid was passed through a short pad of silica gel, eluting with 15% to 30% ethyl acetate in hexane, to give (3R,4S)-3-benzyl 1-tert-butyl 3-azido-4-(3-(4,4,5,5-tetramethyl-1,3,2-dioxaborolan-2-yl)propyl)pyrrolidine-1,3-dicarboxylate (6, 12.5 g, 57%). $^1$H-NMR (CDCl$_3$, 400 MHz): $\delta_H$: 7.35 (5H, m), 5.23 (2H, m), 3.85 (1H, dd, J=39.3, 11.8 Hz), 3.60 (1H, m), 3.37 (1H, dd, J=24.3, 11.8 Hz), 3.25 (1H, ddd, J=40, 10.6, 6.6 Hz), 2.33 (1H, m), 1.43 (9H, s), 1.39-1.26 (3H, m), 1.21 (12H, s), 1.07 (1H, m) and 0.68 (2H, m).

(3R,4S)-3-Benzyl-3-azido-4-(3-(4,4,5,5-tetramethyl-1,3,2-dioxaborolan-2-yl)propyl)pyrrolidine-3-carboxylate, trifluoroacetic Acid Salt (7)

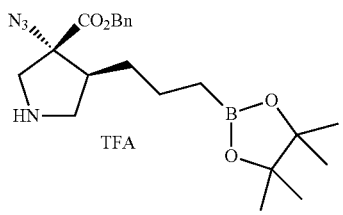

A solution of (3R,4S)-3-benzyl 1-tert-butyl 3-azido-4-(3-(4,4,5,5-tetramethyl-1,3,2-dioxaborolan-2-yl)propyl)pyrrolidine-1,3-dicarboxylate (6, 10.2 g, 19.8 mmol) was dissolved in anhydrous methylene chloride (160 mL), cooled to 0° C. and treated with trifluoroacetic acid (40 mL). The reaction mixture was then allowed to warm, stirred at room temperature for 4 hr and then concentrated under reduced pressure to give a viscous oil. The resultant oil was azeotroped with dry toluene (3×100 mL) to remove residual trifluoroacetic acid and then dried under high vacuum to give (3R,4S)-3-benzyl-3-azido-4-(3-(4,4,5,5-tetramethyl-1,3,2-dioxaborolan-2-yl)propyl)pyrrolidine-3-carboxylate, trifluoroacetic acid salt (7) as a very viscous oil (10.56 g), which slowly turns to a glass. $^1$H-NMR (CDCl$_3$, 400 MHz): $\delta_H$: 9.7 (1H, br m (exch), NH), 7.55 (1H, br s (exch), NH), 7.38 (5H, m), 5.31 (1H, d, J=11.7 Hz), 5.26 (1H, d, J=11.7 Hz), 3.77 (1H, d, J=12.5 Hz), 3.65 (1H, dd, J=11.8, 7.8 Hz), 3.32 (1H, d, J=12.4 Hz), 3.18 (1H, m), 2.54 (1H, m), 1.45-1.26 (3H, m), 1.22 (12H, s), 1.02 (1H, m) and 0.63 (2H, t, J=7.4 Hz).

(3R, 4S)-benzyl-3-azido-1-((S)-2-((tert-butoxycarbonyl)amino)propanoyl)-4-(3-(4,4,5,5-tetramethyl-1,3,2-dioxaborolan-2-yl)propyl)pyrrolidine-3-carboxylate (8)

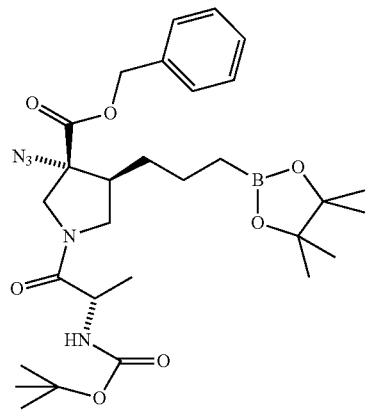

A solution of the TFA salt of (3R, 4S)-benzyl-3-azido-4-(3-(4,4,5,5-tetramethyl-1,3,2-dioxaborolan-2-yl)propyl)pyrrolidine-3-carboxylate (7) (31.43 g, 59.48 mmol) in anhydrous dichloromethane (400 mL) was stirred at room temperature under an atmosphere of dry nitrogen. Triethylamine (33.1 mL, 237.9 mmol), DMAP (200 mg, 1.64 mmol) and HOBt (200 mg, 1.49 mmol) were added and then the reaction mixture was cooled to 0° C. Boc-L-Alanine (16.88 g, 89.22 mmol) was added as a solid in one portion, and then EDCI (17.1 g, 89.22 mmol) was added in 3 portions at 0° C. The reaction mixture was stirred at 0° C. for 1 hour and then allowed to warm to room temperature and stirred overnight at this temperature.

The reaction mixture was poured into 300 mL saturated ammonium chloride solution, separated and then the aqueous phase was extracted (3×100 mL) with dichloromethane. The combined organic phase was washed with water (200 mL), brine (2×200 mL), dried over magnesium sulfate, filtered and concentrated in vacuo to give a pale yellow oil. The reaction was purified on silica gel, eluting with a gradient of ethyl acetate (20-50%) in hexane, to afford the title compound (8) as a colorless oil (30.10 g, 51.41 mmol, 86%) as a mixture of rotamers. $^1$H-NMR (400 MHz, CDCl3) δ: 7.30 (5H, s), 5.35 (1H, dd, J=13.5, 8 Hz, NH), 5.25 (2H, m), 4.35 (1H, m), 4.12-3.30 (4H, m), 2.42 (1H, m), 1.45 (9H, s), 1.37-1.18 (18H, including (3H, d, J=6.5 Hz) and 1.22 (12H, s)), 1.07 (1H, m) and 0.68 (2H, m). LCMS (ESI+ve): C$_{29}$H$_{44}$BN$_5$O$_7$ m/z calculated 585.33, found 586.5 (WO, 530.5 (MH$^+$-iBu), 486.5 (MH$^+$-Boc).

(3R, 4S)-benzyl-1-((S)-2-aminopropanoyl)-3-azido-4-(3-(4,4,5,5-tetramethyl-1,3,2-dioxaborolan-2-yl)propyl)pyrrolidine-3-carboxylate, TFA Salt (9)

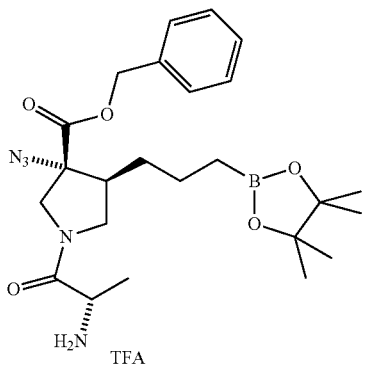

A solution of (3R, 4S)-benzyl-3-azido-1-((S)-2-((tert-butoxycarbonyl)amino)propanoyl)-4-(3-(4,4,5,5-tetramethyl-1,3,2-dioxaborolan-2-yl)propyl)pyrrolidine-3-carboxylate (8) (30.04 g, 51.31 mmol) in anhydrous dichloromethane (250 mL) was cooled to 0° C. and then a solution of TFA (50 mL) in dichloromethane (50 mL) was added drop wise over 10 minutes. The solution was allowed to warm to room temperature and then stirred at this temperature for 3 hours, until TLC showed complete consumption of the starting material. The reaction mixture was concentrated in vacuo to give a pale yellow oil. This oil was dissolved in toluene (100 mL) and concentrated. The azeotropic procedure was repeated three times, to give the product, as the TFA salt, (30.85 g) as a pale yellow oil. (400 MHz, D4-MeOH) δ: 7.39 (4H, m), 7.15 (1H, m), 5.29 (2H, dd, J=14, 12 Hz), 4.25-3.20 (5H, m), 2.51 (1H, m), 1.50-1.25 (6H, including 1.47 (1.5H, d, J=7.0 Hz) and 1.31 (1.5H, d, J=6.9 Hz (alanine rotamers))), 1.20 (12H, s)), 1.07 (1H, m) and 0.65 (2H, m). LCMS (ESI+ve): $C_{24}H_{36}BN_5O_5$ m/z calculated 485.3, found 486.2 (MH$^+$).

(3-((3S, 4R)-1-((S)-2-aminopropanoyl)-4-azido-4-((benxyloxy)carbonyl)pyrrolodin-3-yl)propyl)boronic acid, hydrochloride Salt (11 HCl)

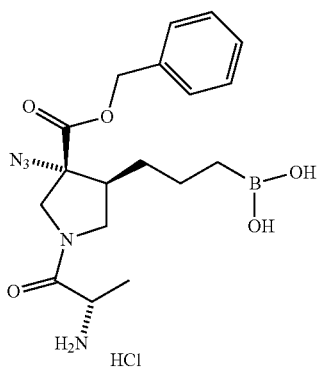

The TFA salt of (3R, 4S)-benzyl-1-((S)-2-aminopropanoyl)-3-azido-4-(3-(4,4,5,5-tetramethyl-1,3,2-dioxaborolan-2-yl)propyl)pyrrolidine-3-carboxylate (9) (30.76 g, 51.31 mmol), was dissolved in a biphasic mixture of methanol (200 mL) and hexane (400 mL). Isobutylboronic acid (18.31 g, 179.6 mmol) and then 2N Hydrochloric acid (50.85 mL, 101.7 mmol) was added. The reaction mixture was stirred vigorously at room temperature for 16 hours. The methanol phase was separated and washed with hexane (5×100 mL) and then concentrated in vacuo to give the boronic acid (11 HCl), as the hydrochloride salt, as an off-white foam. $^1$H-NMR (400 MHz, D$_2$O) δ: 7.48-7.42 (5H, m), 5.31 (2H, m), 4.22 (1H, dd, J=13, 6.5 Hz), 3.95-3.10 (4H, m), 2.71-2.51 (1H, m), 1.40-1.25 (3H, m), 1.25-0.98 (4H, m including 1.20 (1.5H, d, J=6.9 Hz) and 1.07 (1.5H, d, J=6.9 Hz (alanine rotamers))) and 0.69 (2H, m). LCMS (ESI+ve): $C_{18}H_{26}BN_5O_5$ m/z calculated 403.2, found 404.2 (MH$^+$).

(3-((3S, 4R)-1-((S)-2-aminopropanoyl)-4-azido-4-((benxyloxy)carbonyl)pyrrolodin-3-yl)propyl)boronic Acid (11)

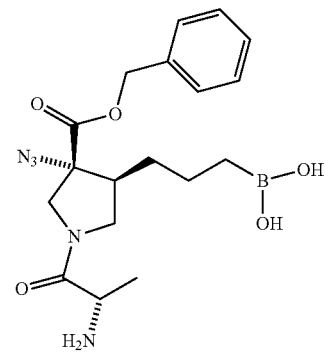

The hydrochloride salt of (3-((3S, 4R)-1-((S)-2-aminopropanoyl)-4-azido-4-((benxyloxy)carbonyl)pyrrolodin-3-yl)propyl)boronic acid (11 HCl), from the previous step, was dissolved in 30 mL water and then the pH of the solution was adjusted to pH 9 by the careful addition of solid potassium carbonate. The resultant solution was saturated with the addition of solid sodium chloride and then was extracted with dichloromethane (5×100 mL). The combined dichloromethane phase was dried over magnesium sulfate, filtered and concentrated in vacuo to give the product 11, as its free base, as a white foamy solid (19.4 g, 48.11 mmol, 94%). $^1$H-NMR (400 MHz, D4-MeOH) δ: 7.44-7.36 (5H, m), 5.31 (1H, d, J=1.8 Hz), 5.27 (1H, d, J=1.8 Hz) 4.05 (1H, dd, J=12, 5 Hz), 3.80 (1H, m), 3.69-3.55 (2H, m), 3.45-3.30 (1H, m), 2.51 (1H, m), 1.40-1.05 (7H, m, including 1.22 (1.5H, d, J=6.8 Hz) and 1.07 (1.5H, d, J=6.8 Hz (alanine rotamers))) and 0.63 (2H, m). LCMS (ESI+ve): $C_{18}H_{26}BN_5O_5$ m/z calculated 403.2, found 404.7 (MH$^+$).

(3R, 4S)-3-amino-1-((S)-2-aminopropanoyl)-4-(3-boronopropyl)-yl)pyrrolidine-3-carboxylate (10)

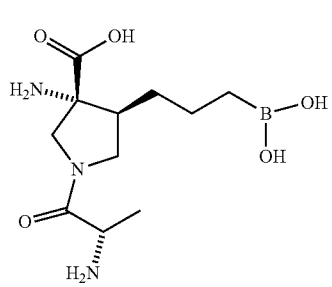

The azido benzyl ester, (3-((3S,4R)-1-((S)-2-aminopropanoyl)-4-azido-4-((benxyloxy)carbonyl)pyrrolodin-3-yl)propyl)boronic acid 11 (9.70 g, 24.06 mmol) was suspended in a mixture of water (300 mL) and ethyl acetate (30 mL) and stirred vigorously. 10% Palladium on charcoal (2.6 g, 0.1 eq) was added and then the stirred mixture was evacuated under mild vacuum, and flushed with hydrogen. The evacuation/flushing procedure was repeated 3× to remove air and exchange it with hydrogen and then the reaction was stirred vigorously overnight at room temperature under a hydrogen balloon, at which time, LCMS analysis of a filtered aliquot showed the complete reduction of the azide and benzyl ester groups. The reaction mixture was put under vacuum to remove hydrogen and then flushed with nitrogen, filtered through a pad of celite (with 3 water washes) and then the solution was concentrated to approx 50 mL in vacuo. The resultant aqueous solution was filtered through a 4 micron filter (to remove trace Pd) and then concentrated in vacuo to give the title compound 10 as a white powder (6.45 g, 93%). $^1$H-NMR (400 MHz, D$_2$O) δ: 4.12 (1H, m), 4.05 (1H, m), 3.92 (1H, m), 3.60-3.22 (2H, m), 2.47-2.18 (1H, m), 1.58-1.31 (6H, m including 1.46 (3H, d, J=6.9 Hz)), 1.24-1.19 (1H, m) and 0.79 (2H, m). LCMS (ESI+ve): C$_{11}$H$_{20}$BN$_3$O$_5$ m/z calculated 287.2, found 269.9 (MH$^+$—H$_2$O), 251.9 (MH$^+$-2H$_2$O) and (ESI−ve): C$_{11}$H$_{20}$BN$_3$O$_5$ m/z calculated 287.2, found 267.7 (M-H—H$_2$O).

Conversion of 10 to ethanolate 10e is as described in Example 1, above.

(3R, 4S)-3-amino-1-((S)-2-aminoacetyl)-4-(3-boronopropyl)-yl)pyrrolidine-3-carboxylate (12) and (6aS,9aR)-8-(2-aminoacetyl)-9a-amino-3-ethoxyoctahydro-[1,2]oxaborocino[6,7-c]pyrrol-1(3H)-one 12e

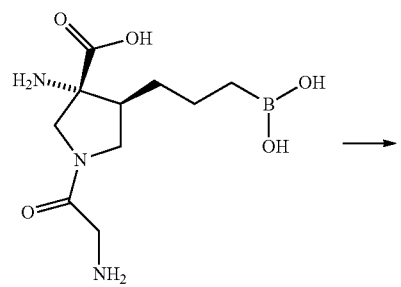

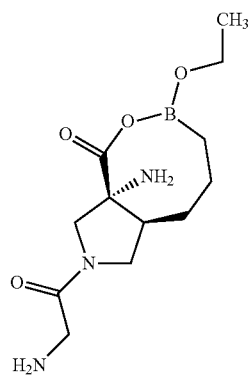

Compound 12 was prepared as described for 10 in Example 2, using Boc glycine as the coupling partner with 7. Compound 12 (1.0 g, 3.7 mmol) was suspended in sufficient anhydrous ethanol (~40 mL) to fully dissolve the material at 80° C. This solution was heated at 80° C. for 2 hrs under an atmosphere of dry nitrogen. The reflux condenser was changed to a small still head and the reaction was distilled (at atmospheric pressure, with an attached DRIERITE® drying tube to exclude moisture) until the hot solution had started to become cloudy (approximately 20 mL of ethanol had been collected during the distillation). Anhydrous ethanol (20 mL) was added and then the reaction was heated to 80° C. and stirred at 80° C. for a further 4 hrs. The distillation process was repeated until the solution became cloudy (~20 mL distillate collected). This was repeated once more and the suspension was allowed to cool to RT. The solid was filtered and quickly suction dried, and then further dried under high vacuum (38 mTor) at RT for 2 hrs to give the product as an off-white powder (986 mg) as a 2:1 mix of rotamers. $^1$H-NMR (400 MHz, d6-DMSO (2:1 rotamer population)) δ: 6.73-7.31 (4H, exch), 3.84 (1H, m), 3.57-3.71 (3H, m), 3.48-3.21 (3H, m), 3.05 (0.67 H, dd, J=11.8, 9.7 Hz), 2.88 (0.33H, t, J=11.5 Hz), 2.48-2.35 (1H, m), 1.67-1.83 (2H, m), 1.52-1.41 (1H, m), 1.09-1.03 (3H, m), 0.97 (1H, m), 0.67 (1H, dd, J=14.9, 5.6 Hz, BCHH) and 0.42 (1H, m, BCHH). $^{11}$B-NMR (400 MHz, DMSO) δ: 7.78 ppm. FTIR (powder diffraction) (cm$^{-1}$): 2912 (w), 1720 (s), 1645 (s), 1463 (s), 1269 (s), 1102 (s), 1063 (m), 1037 (m), 660 (s) and 573 (s).

Example 4: Exemplary Cyclic Alcoholates

The following compounds were prepared as in Example 1 (i.e., the conversion of 10 to 10e) by heating with the corresponding anhydrous alcohol under conditions that removed water, such as azeotropic distillation:

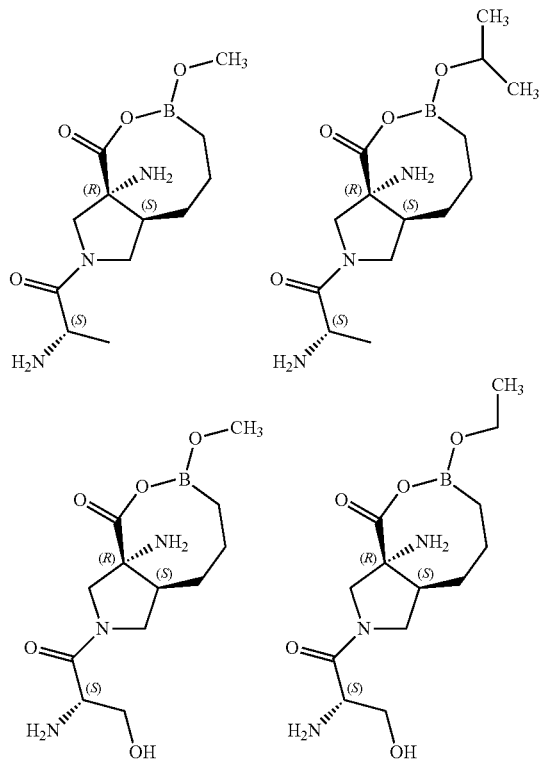

Example 5: Synthesis of Select Compounds of the Disclosure

6aS, 9aR)-9a-amino-8-((S)-2-amino-3-hydroxypropanoyl)-3-ethoxyoctahydro-[1,2]oxaboro-cino{6,7-c}pyrrol-1{3H}one ($R_1$=CH$_2$OH, $R_2$=Et)

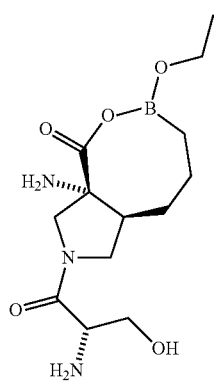 [SMILES: CCOB1CCC[C@H]2CN(C(=O)[C@@H](N)CO)C[C@@]2(N)C(=O)O1]

(6aS, 9aR)-9a-Amino-8-((S)-2-amino-hydroxypropanoyl)-3-ethoxyoctahydro-[1,2]oxaborocino{6,7-c}pyrrol-1{3H}one ($R_1$=CH$_2$OH, $R_2$=Et) was prepared according to the general procedure using the serinamide (3R, 4S)-3-amino-1-((S)-2-amino-3-hydroxypropanoyl)-4-(3-boronopropyl)-yl)pyrrolidine-3-carboxylate as the starting material and ethanol as the alcohol solvent, and was isolated as a pale yellow powder, $^1$H-NMR (400 MHz, d6-DMSO (3:2 rotamer population)) δ: 6.86-6.97 (2H, exch), 3.84 (2H, m), 3.60-3.68 (1H, m), 3.48-3.35 (4H, m), 3.22 (1H, m), 3.11 (0.6H, dd, J=11.2, 10.4 Hz) and 2.80 (0.4H, t, J=11.6 Hz), 2.36 (0.6H, m) and 2.31 (0.4H, m), 1.83-1.65 (2H, m), 1.48-1.36 (1H, m), 1.08-1.03 (3H, m, CH3CH2O), 0.96 (1H, m), 0.64 (1H, dd, J=14.0, 4.5 Hz, BCHH) and 0.41 (1H, m, BCHH). $^{11}$B-NMR (400 MHz, DMSO) δ: 7.62 ppm. FTIR (powder diffraction) (cm$^{-1}$): 1627 (s), 1459 (m), 1365(m), 1063 (s), 589 (m).

(6aS, 9aR)-9a-amino-8-((S)-2-aminopropanoyl)-3-isopropoxyoctahydro-[1,2]oxaborocino{6,7-c}pyrrol-1{3H}one ($R_1$=Me, $R_2$=i-Pr)

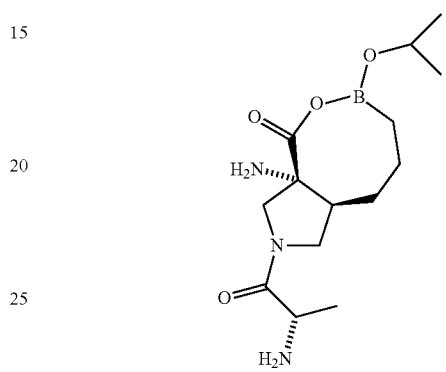

(6aS, 9aR)-9a-Amino-8-((S)-2-aminopropanoyl)-3-isopropoxyoctahydro-[1,2]oxaborocino{6,7-c}pyrrol-1{3H}one ($R_1$=Me, $R_2$=Et) was prepared according to the general procedure using the alaninamide (3R, 4S)-3-amino-1-((S)-2-aminopropanoyl)-4-(3-boronopropyl)-yl)pyrrolidine-3-carboxylate as the starting material and 2-propanol as the alcohol solvent, and was isolated as a pale yellow powder, $^1$H-NMR (400 MHz, d6-DMSO (3:2 rotamer population)) δ: 6.64-6.87 (2H, exch), 3.73-3.81 (1H, m), 3.56-3.66 (1H, m), 3.37-3.49 (2H, m), 3.16 (1H, d, J=12.9 Hz), 3.10 (0.6H, dd, J=10.8, 9.6 Hz) and 2.78 (0.4H, t, J=11.6 Hz), 2.43 (0.6H, m) and 2.31 (0.4H, m), 1.69 (2H, m), 1.40 (1H, m), 1.07 (3H, d, J=6.9 Hz, CH3CHO), 1.02 (3H, m), 1.00 (3H, d, J=6.1 Hz, CH3CHO), 0.95 (1H, m), 0.55 (1H, dd, J=14.7, 5.6 Hz, BCHH) and 0.38 (1H, m, BCHH). $^{11}$B-NMR (400 MHz, DMSO) δ: 8.24 ppm. FTIR (powder diffraction) (cm$^{-1}$): 1723 (s), 1618 (s), 1459 (s), 1269 (s), 1129 (s), 1074 (m), 653 (m) and 579 (m).

(6aS, 9aR)-9a-amino-8-((S)-2-aminopropanoyl)-3-propoxyoctahydro-[1,2]oxaborocino{6,7-c}pyrrol-1{3H}one ($R_1$=Me, $R_2$=n-Pr)

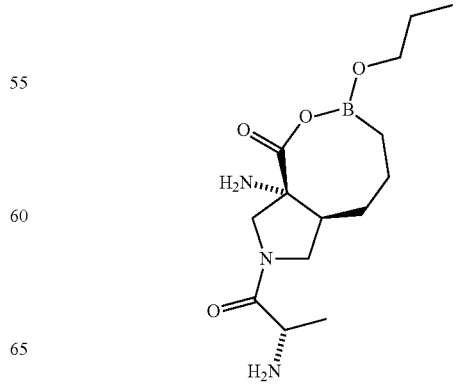

(6aS, 9aR)-9a-Amino-8-((S)-2-aminopropanoyl)-3-propoxyoctahydro-[1,2]oxaborocino{6,7-c}pyrrol-1{3H}one (R₁=Me, R₂=n-Pr) was prepared according to the general procedure using the alaninamide (3R, 4S)-3-amino-1-((S)-2-aminopropanoyl)-4-(3-boronopropyl)-yl)pyrrolidine-3-carboxylate as the starting material and 1-propanol as the alcohol solvent, and was isolated as a pale yellow powder, ¹H-NMR (400 MHz, d6-DMSO (3:2 rotamer population)) δ: 6.85-6.92 (2H, exch), 3.81 (1H, dd, J=11.5, 6.3 Hz), 3.67 (0.6H, dd, J=9.6, 6.3 Hz) and 3.61 (0.4H, dd, J=11.3, 7.8 Hz), 3.51 (1H, m), 3.42-3.32 (2H, m) 3.20 (1H, d, J=12.6 Hz), 3.12 (0.6H, dd, J=11.7, 9.8 Hz) and 2.79 (0.4H, t, J=11.6 Hz), 2.40 (0.6H, m) and 2.31 (0.4H, m), 1.82-1.69 (2H, m), 1.48-1.36 (3H, m), 1.08 (3H, m, CH 3CHN), 0.96 (1H, m), 0.85-0.80 (3H, m), 0.63 (1H, dd, J=14.6, 5.4 Hz, BCHH) and 0.41 (1H, m, BCHH).

Example 6: Oral Bioavailability Studies and Enzyme Potency

Compound dosing solutions were prepared at 2.5 and 5 mg/mL in water. Female C57BL/6 mice (16-20 g) from Charles River Laboratories (Hollister, Calif.) were housed in cages for at least 3 days prior to dosing. PicoLab 5053 irradiated rodent diet was provided ad libitum throughout the study. Compounds were administered once to the appropriate animals by oral gavage at either 25 or 50 mg/kg (10 mL/kg). Blood samples were collected (3 animals per time point) at 30 min and 1, 2, 4, 8 hr post-dose for the 25 mg/kg studies, and at 1 hour for the 50 mg/kg studies. The blood samples were maintained on wet ice and then centrifuged for 10 min in a refrigerated centrifuge. The resultant plasma was separated, transferred to labeled polypropylene tubes and stored frozen in a freezer set to maintain under −70° C. until analysis.

The plasma samples were analyzed by an LC-MS system. 50 μL of a plasma sample was mixed with 100 μL of acetonitrile/water (80:20) with 0.1% TFA containing 100 ng/mL of an internal standard. The mixture was vortexed and centrifuged. 30 μL of the supernatant was transferred to a 96-well plate containing 90 μL of water with 0.1% formic acid. 20 μL of the resulting solution was injected into a SCIEX QTRAP4000 LC/MS/MS equipped with an electrospray ionization source for quantification.

Oral PK parameters were calculated by noncompartmental analysis of the concentration-time data using Phoenix WinNonLin 6.3 software (Pharsight, Mountain View, Calif.). Area under the concentration-time curve (AUC) was estimated using a linear-up and log-down trapezoidal method, calculated from the dosing time to the last measurable concentration.

Inhibition of human arginase-1 was determined using the assay described in the publication Van Zandt et al., J Med. Chem. 2013, 56, 2586-2580, with the following modifications: human recombinant Arginase I was purchased from Enzo Life Sciences and assayed at a final concentration of 80 ng/mL in a total reaction volume of 25 μl. The reaction buffer was Phosphate Buffered Saline supplemented with 0.01% Tx-100, 0.5 mM DTT, 0.1 mM CaCl₂, and 0.49 mM MgCl₂. After diluted inhibitor compounds were added, reactions were initiated by adding L-arginine substrate to a final concentration of 20 mM followed by incubation at 37° C. for 30 minutes. Reactions were quenched and urea production was measured by addition of 150 μl urea developer solution from BioAssay Systems.

AUC and arginase-1inhibition IC₅₀ values for exemplary compounds are shown below:

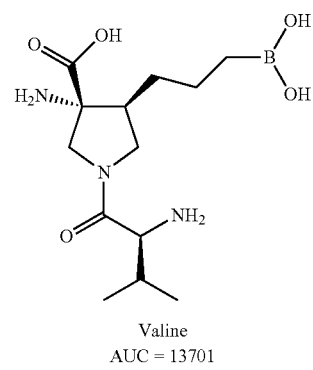

Valine
AUC = 13701
IC₅₀ = 70 nM

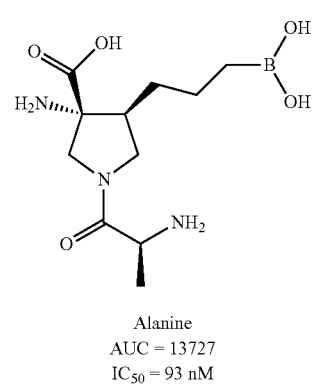

Alanine
AUC = 13727
IC₅₀ = 93 nM

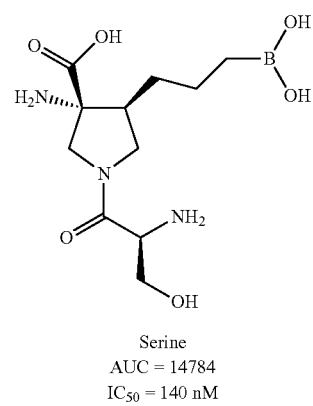

Serine
AUC = 14784
IC₅₀ = 140 nM

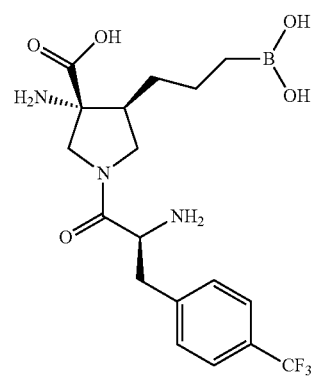

Trifluoromethyl phenylalanine
AUC = 5783

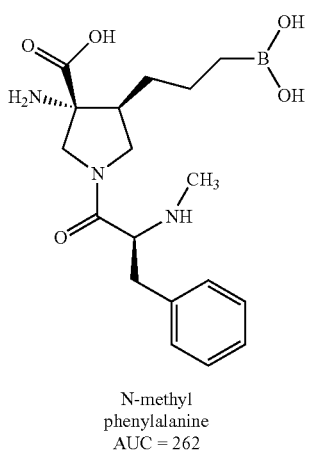

N-methyl
phenylalanine
AUC = 262

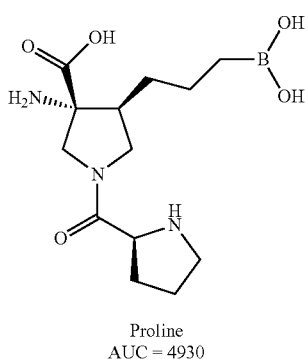

Proline
AUC = 4930

As compared to the proline, trifluoromethyl phenylalanine, and N-methylphenylalanine-derived compounds, the oral exposure for the alanine, valine, and serine derivatives are more favorable.

Example 7: Pharmacokinetic Studies

The pharmacokinetics of the compounds of the disclosure were studied after administration of a single dose (50 mg/kg) at a single time point (1 hour) in mice. Plasma concentrations were determined as described in Example 4. Results for exemplary compounds are shown below. Arginase-1 $IC_{50}$ are provided for selected compounds. For these cases, the active isomer was prepared, and used to determine the $IC_{50}$.

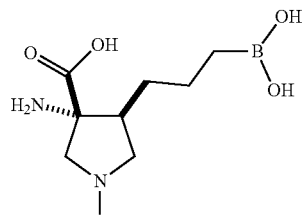

Plasma conc = 6.43 µM

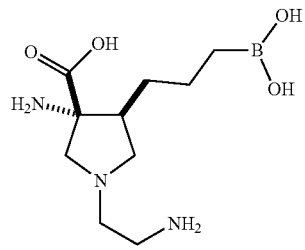

Plasma conc = 1.63 µM

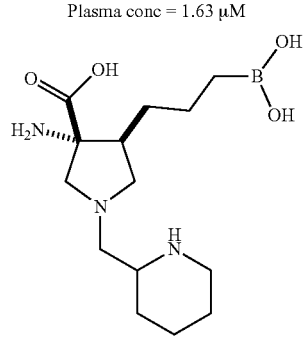

Plasma conc = 0.34 µM

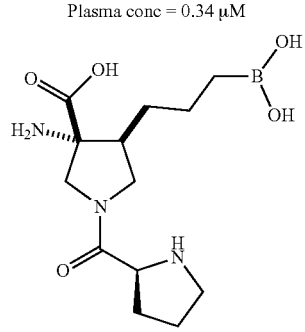

Plasma conc = 4.98 µM

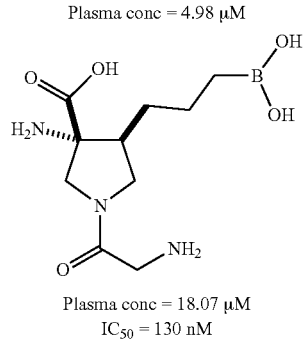

Plasma conc = 18.07 µM
$IC_{50}$ = 130 nM

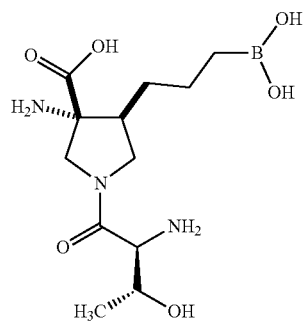

Plasma conc = 26.50 µM
$IC_{50}$ = 102 nM

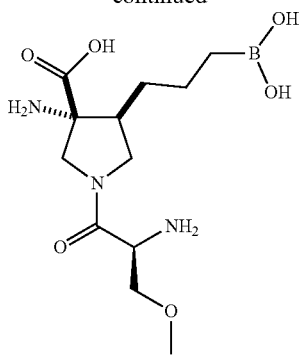
Plasma conc = 53.90 μM
IC₅₀ = 106 nM
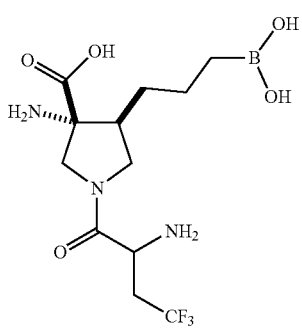
Plasma conc = 32.80 μM
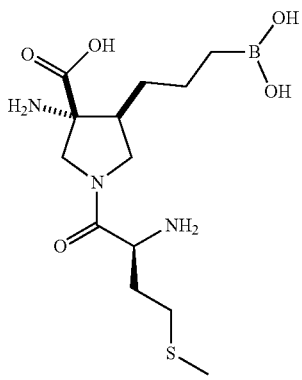
Plasma conc = 31.95
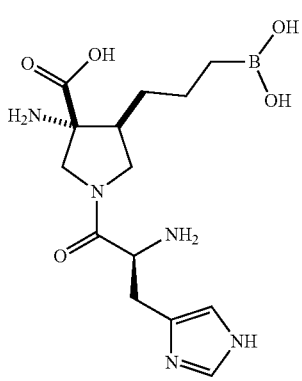
Plasma conc = 28.67 μM
IC₅₀ = 131 nM
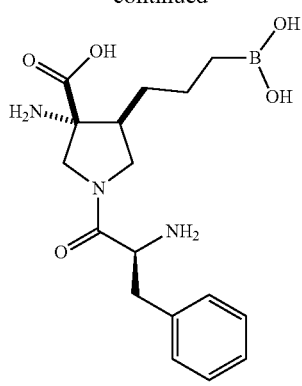
Plasma conc = 32.13 μM
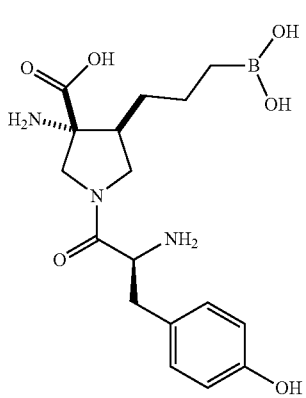
Plasma conc = 22.27 μM
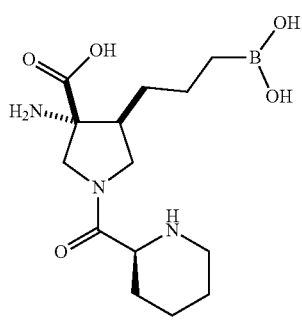
Plasma conc = 22.33 μM
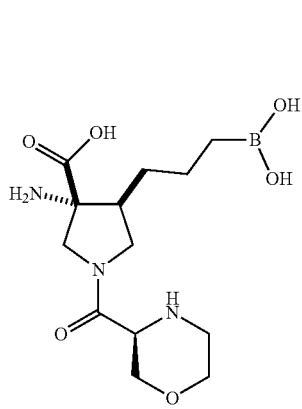
Plasma conc = 8.96 μM 147
-continued
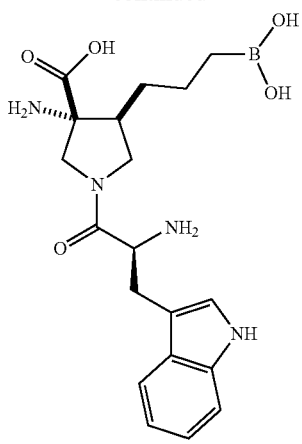
Plasma conc = 30.33 μM
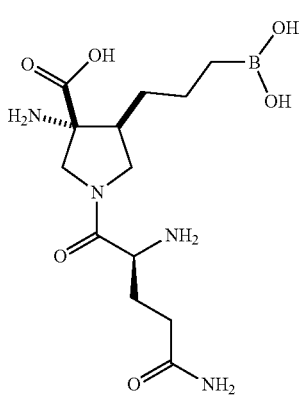
Plasma conc = 14.43 μM
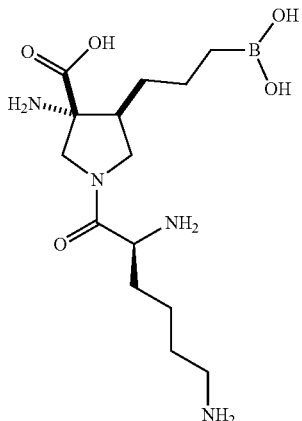
Plasma conc = 30.83 μM
$IC_{50}$ = 94 nM
148
-continued
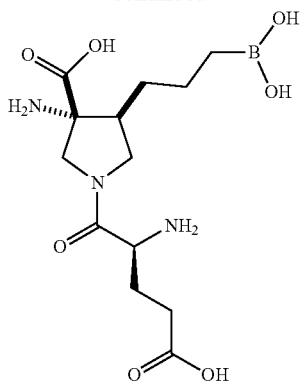
Plasma conc = 10.24 μM
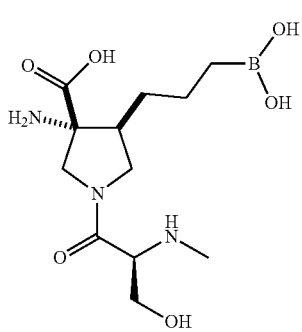
Plasma conc = 0.74 μM
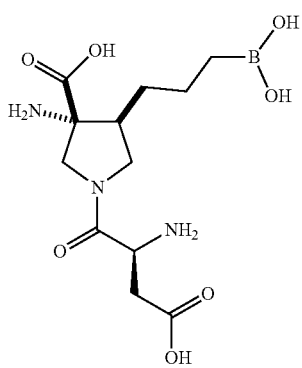
Plasma conc = 8.24 μM
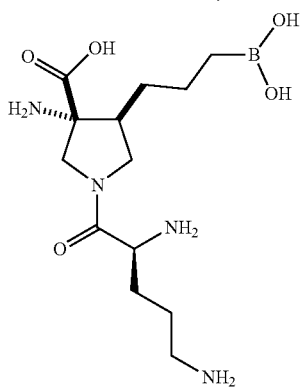
Plasma conc = 14.83 μM

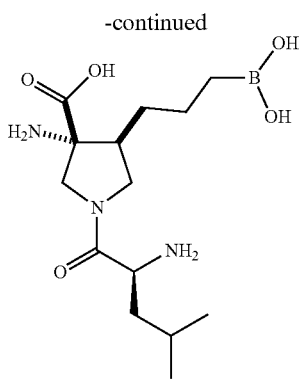

Plasma conc = 65.60 μM

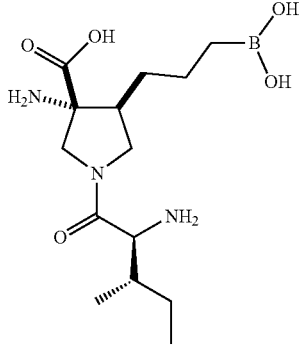

Plasma conc = 41.03 μM

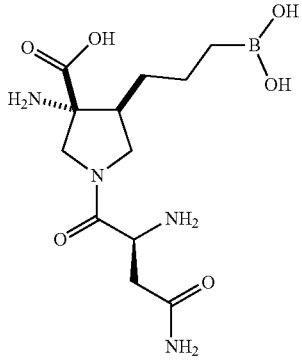

Plasma conc = 30.7 μM

Example 8: Single-Agent Anti-Tumor Activity of Compound 10

Lewis Lung Carcinoma Efficacy Study

Figure 3:
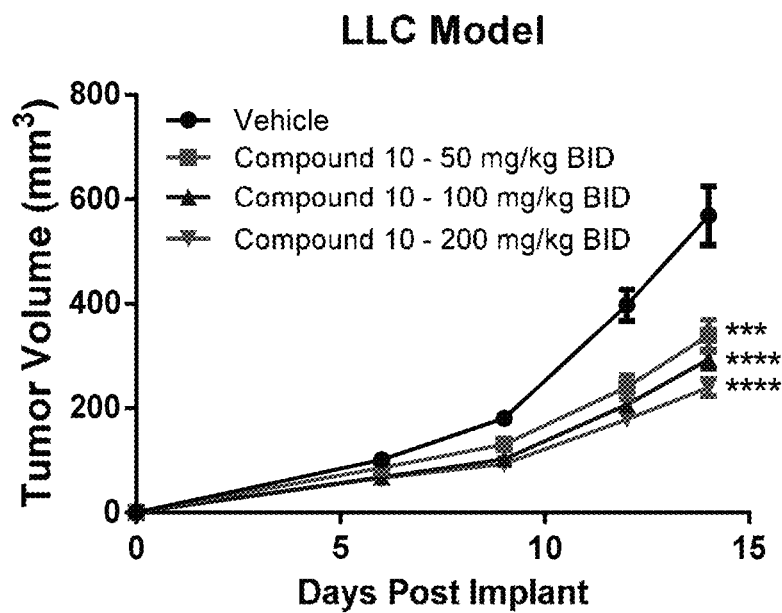
FIG. 3 is a graph depicting the tumor volume over time. Arginase inhibitor compound 10, administered as a single agent, slows tumor growth relative to control in C57BL/6 mice implanted with Lewis Lung Carcinoma cells.

Female C57.Bl/6 mice (n=40) were implanted subcutaneously with $1 \times 10^6$ Lewis Lung Carcinoma cells suspended in PBS. The day following implantation, mice were randomized into 4 groups of n=10 mice to receive the following treatments dosed orally twice daily until study end: 1) Vehicle (water); 2) Compound 10 at 50 mg/kg formulated in water; 3) Compound 10 at 100 mg/kg formulated in water; or 4) Compound 10 at 200 mg/kg formulated in water. Tumors were measured three times per week with digital calipers and tumor volumes calculated with the following formula: tumor volume $(mm^3)=(a \times b^2/2)$ where 'b' is the smallest diameter and 'a' is the largest perpendicular diameter. *P-value<0.001, **P-value<0.0001 (Two-sided T-test). Results are shown in FIG. 3.

Madison109 Efficacy Study

Figure 4:
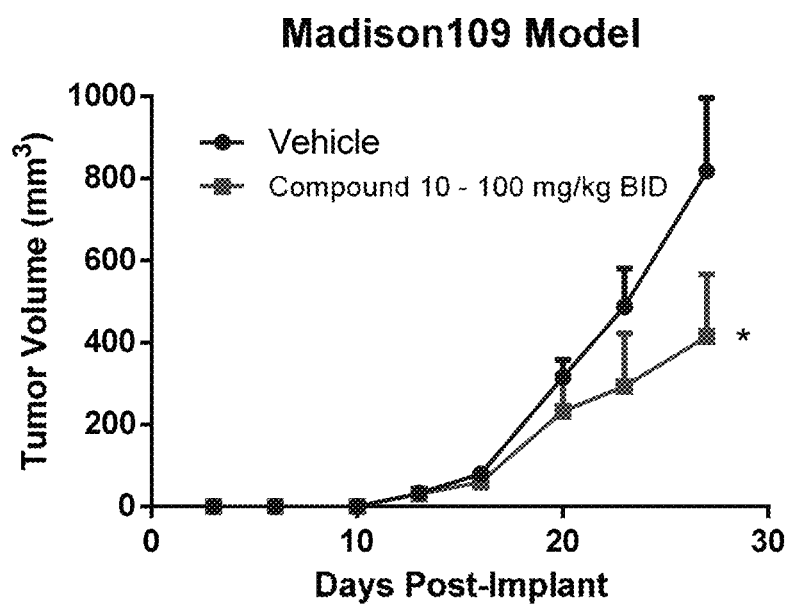
FIG. 4 is a graph depicting the tumor volume over time. Madison109 murine lung carcinoma cells were implanted in BALB/c mice and mice were dosed orally with vehicle or arginase inhibitor compound 10 BID (N=10 per group).

Female balb/c mice (n=20) were implanted subcutaneously with $5 \times 10^4$ Madison109 murine lung carcinoma cells suspended in PBS. The day following implantation, mice were randomized into 2 groups of n=10 mice to receive the following treatments dosed orally twice daily until study end: 1) Vehicle (water); or 2) Compound 10 at 100 mg/kg formulated in water. Tumors were measured three times per week with digital calipers and tumor volumes calculated with the following formula: tumor volume $(mm^3)=(a \times b^2/2)$ where 'b' is the smallest diameter and 'a' is the largest perpendicular diameter. *P-value<0.05 (Two-sided T-test). Results are shown in FIG. 4.

B16 Efficacy Study

Figure 5:
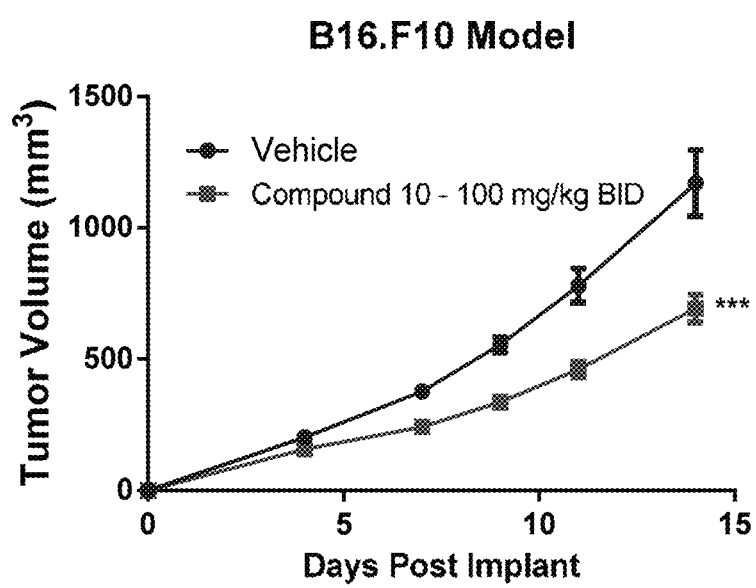
FIG. 5 is a graph depicting the tumor volume over time. B16F10 murine melanoma cells were implanted in C57BL/6 mice and mice were dosed orally with vehicle or arginase inhibitor compound 10 BID (N=10 per group).

Female C57.Bl/6 mice (n=20) were implanted subcutaneously with $2 \times 10^6$ B16F10 murine melanoma cells suspended in PBS. The day following implantation, mice were randomized into 2 groups of n=10 mice to receive the following treatments dosed orally twice daily until study end: 1) Vehicle (water); or 2) Compound 10 at 100 mg/kg formulated in water. Tumors were measured three times per week with digital calipers and tumor volumes calculated with the following formula: tumor volume $(mm^3)=(a \times b^2/2)$ where 'b' is the smallest diameter and 'a' is the largest perpendicular diameter. ***P-value<0.001 (Two-sided T-test). Results are shown in FIG. 5.

Example 9: 4T1 Combination Therapy Studies

Figure 6A:
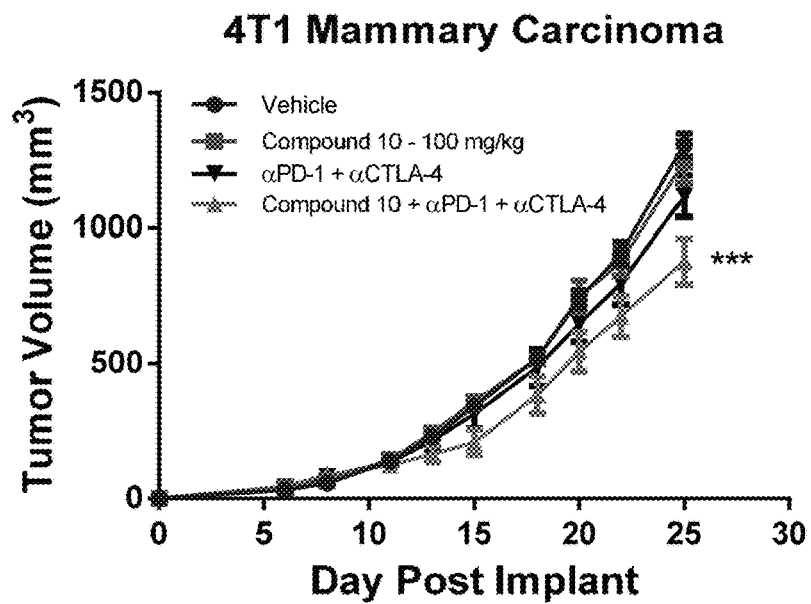
FIG. 6A and FIG. 6B depict the growth of 4T1 mammary carcinoma cells implanted orthotopically into female BALB/c mice and treated with either vehicle; compound 10
Figure 6B:
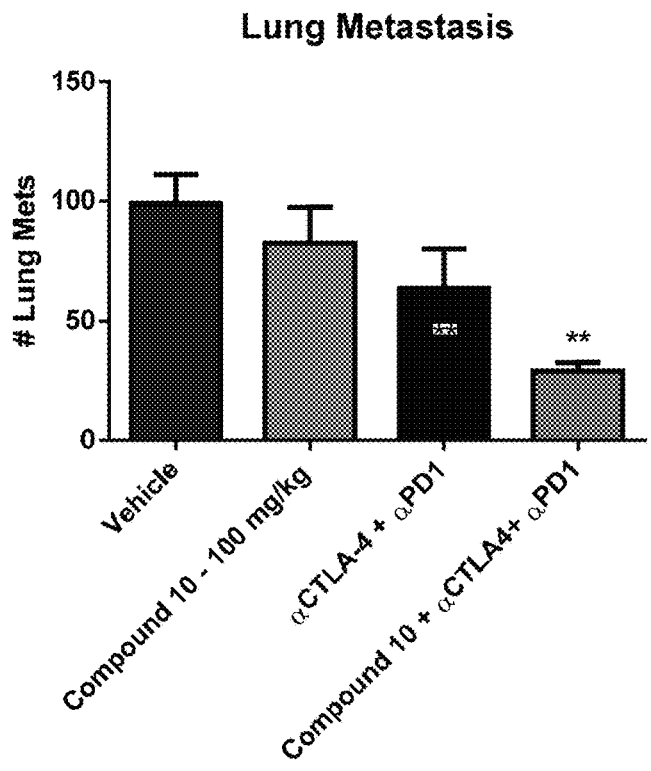

Female balb/c mice (n=40) were implanted in the mammary fat pad with $1 \times 10^5$ 4T1 murine mammary carcinoma cells suspended in PBS. The day following implantation, mice were randomized into 4 groups of n=10 mice each to receive the following treatments: 1) Vehicle (water) dosed orally twice daily until study end; 2) Compound 10 at 100 mg/kg formulated in water dosed orally twice daily until study end; 3) The combination of anti-PD-1 (clone RMPI-14) dosed IP at 5 mg/kg on days 3, 6, and 9 post-implant plus anti-CTLA-4 (clone 9H10) dosed IP at 5 mg/kg on days 2, 5, and 8 post-dose; or 4) the triple combination of compound 10 plus anti-PD-1 plus anti-CTLA-4 at their respective regimens. Tumors were measured three times per week with digital calipers and tumor volumes calculated with the following formula: tumor volume $(mm^3)=(a \times b^2/2)$ where 'b' is the smallest diameter and 'a' is the largest perpendicular diameter. ***P-value<0.001 (Two-sided T-test). On day 25, mice were sacrificed and lungs perfused with India Ink (25% in PBS) then harvested and fixed in 100% ethanol: 10% neutral buffered formalin: acetic acid mixture at 10:1: 0.5 ratio. The number of lung metastases was counted manually in a blinded manner. Results are shown in FIG. 6.

Example 10: Thermogravimetric Analysis (TGA) Study on Compound 10e

In the TGA study, a weighted amount of compound 10e was treated with increasing amounts of water vapor (increased humidity) and the impact of humidity on the weight of the sample was evaluated. FIG. 7 shows the adsorption isotherm (top line) and desorption isotherm (bottom line) for compound 10e. As shown in FIG. 7, a TGA plot of compound 10e shows that the compound resists water uptake up to about 60% relative humidity. The low moisture uptake of compound 10e significantly facilitates manufacturing of the compound and preparation of pharmaceutical compositions comprising the compound.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control. Particular applications that are incorporated by reference include U.S. provisional application Nos. 62/438,092 and 62/439,614 from which the present application claims benefit and priority.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. A compound having a structure of formula (I*):

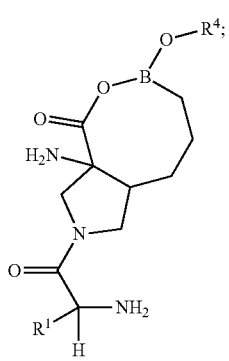

or a pharmaceutically acceptable salt thereof;
wherein:
$R^1$ is methyl; and
$R^4$ is H or $(C_1-C_6)$alkyl.

2. The compound of claim 1, having a structure of the following formula:

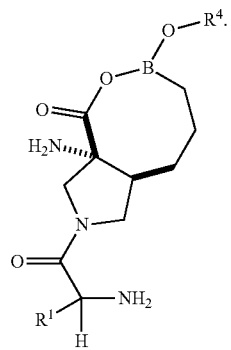

3. The compound of claim 1, having a structure of the following formula:

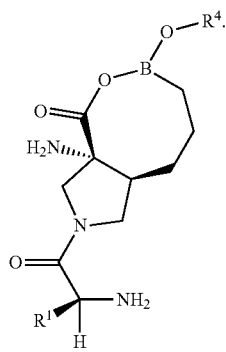

4. The compound of claim 1, wherein $R^4$ is $(C_1-C_6)$alkyl.

5. The compound of claim 4, wherein $R^4$ is methyl, ethyl, propyl, or isopropyl.

6. A compound having the following structure:

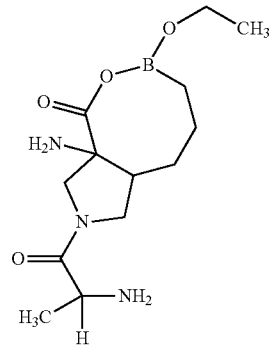 [SMILES: CCOB1CCCC2CN(C(=O)C(C)N)CC2(N)C(=O)O1]

or a pharmaceutically acceptable salt thereof.

7. A compound having the following structure:

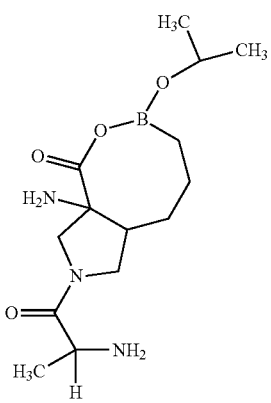 [SMILES: CC(C)OB1CCCC2CN(C(=O)C(C)N)CC2(N)C(=O)O1]

or a pharmaceutically acceptable salt thereof.

8. A solid pharmaceutical composition comprising a compound of claim 1 and a pharmaceutically acceptable carrier.

9. The compound of claim 6, having the following structure:

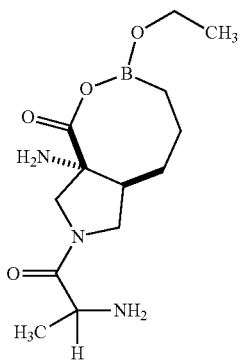

or a pharmaceutically acceptable salt thereof.

10. The compound of claim 6, having the following structure:

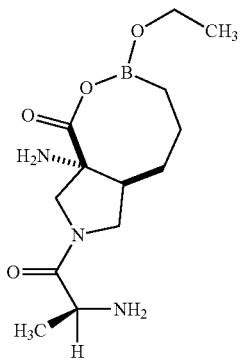

or a pharmaceutically acceptable salt thereof.

11. The compound of claim 7, having the following structure:

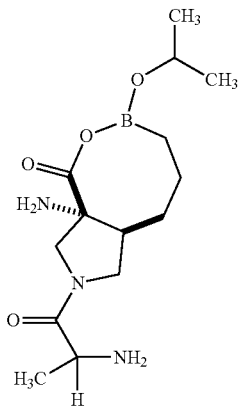

or a pharmaceutically acceptable salt thereof.

12. The compound of claim 7, having the following structure:

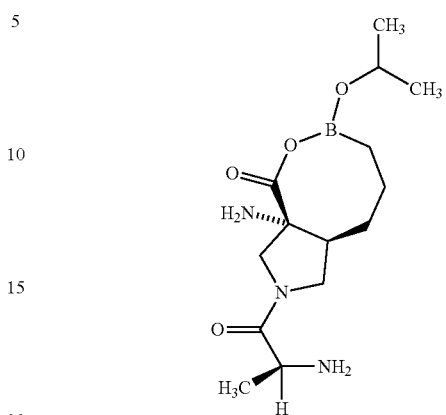

or a pharmaceutically acceptable salt thereof.

13. The compound of claim 1, wherein $R^4$ is H.

14. The compound of claim 2, wherein $R^4$ is H.

15. The compound of claim 2, wherein $R^4$ is $(C_1-C_6)$alkyl.

16. The compound of claim 15, wherein $R^4$ is methyl, ethyl, propyl, or isopropyl.

17. The compound of claim 3, wherein $R^4$ is H.

18. The compound of claim 3, wherein $R^4$ is $(C_1-C_6)$alkyl.

19. The compound of claim 18, wherein $R^4$ is methyl, ethyl, propyl, or isopropyl.

20. A solid pharmaceutical composition comprising a compound of claim 3 and a pharmaceutically acceptable carrier.

21. A solid pharmaceutical composition comprising a compound of claim 4 and a pharmaceutically acceptable carrier.

22. A solid pharmaceutical composition comprising a compound of claim 3 and a pharmaceutically acceptable carrier.

23. A solid pharmaceutical composition comprising a compound of claim 7 and a pharmaceutically acceptable carrier.

24. A solid pharmaceutical composition comprising a compound of claim 10 and a pharmaceutically acceptable carrier.

25. A solid pharmaceutical composition comprising a compound of claim 12 and a pharmaceutically acceptable carrier.

26. A solid pharmaceutical composition comprising a compound of claim 18 and a pharmaceutically acceptable carrier.

* * * * *

UNITED STATES PATENT AND TRADEMARK OFFICE
CERTIFICATE OF CORRECTION

PATENT NO. : 10,287,303 B2  
APPLICATION NO. : 15/853310  
DATED : May 14, 2019  
INVENTOR(S) : Eric B. Sjogren et al.

Page 1 of 1

It is certified that error appears in the above-identified patent and that said Letters Patent is hereby corrected as shown below:

In the Claims

In Column 153, Claim 10, Line 20, " 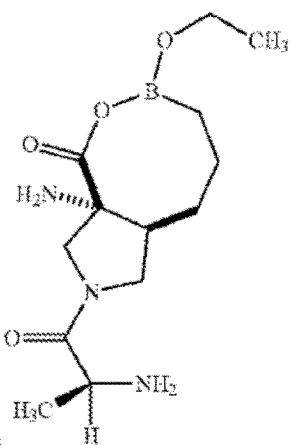 " should read

-- 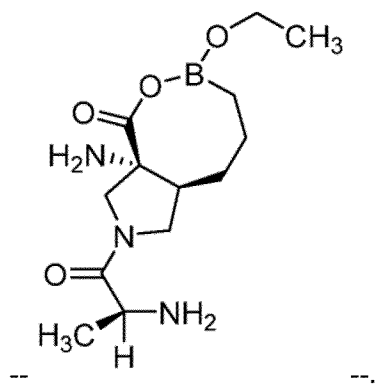 --.

Signed and Sealed this  
Nineteenth Day of November, 2019

Andrei Iancu  
*Director of the United States Patent and Trademark Office*

UNITED STATES PATENT AND TRADEMARK OFFICE
CERTIFICATE OF CORRECTION

PATENT NO. : 10,287,303 B2
APPLICATION NO. : 15/853310
DATED : May 14, 2019
INVENTOR(S) : Eric B. Sjogren et al.

It is certified that error appears in the above-identified patent and that said Letters Patent is hereby corrected as shown below:

In the Claims

At Column 154, Claim 22, Lines 43-45, please change:
"a compound of claim 3 and a pharmaceutically acceptable carrier."

To:
-- a compound of claim 6 and a pharmaceutically acceptable carrier. --

Signed and Sealed this
Thirty-first Day of May, 2022

Katherine Kelly Vidal
*Director of the United States Patent and Trademark Office*